United States Patent
Soto-Jara et al.

(10) Patent No.: US 11,249,092 B2
(45) Date of Patent: *Feb. 15, 2022

(54) DETECTION OF MISFOLDED TAU PROTEIN

(71) Applicants: Amprion, Inc., San Francisco, CA (US); BOARD OF REGENTS OF THE UNIVERSITY OF TEXAS SYSTEM, Austin, TX (US)

(72) Inventors: Claudio Soto-Jara, Friendswood, TX (US); Russell M. Lebovitz, Oakland, CA (US); Benedikt K. Vollrath, San Diego, CA (US); Mohammad Shahnawaz, Houston, TX (US); Nicolas Mendez Dinamarca, Houston, TX (US)

(73) Assignee: Amprion, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/981,449

(22) Filed: May 16, 2018

(65) Prior Publication Data

US 2018/0335438 A1 Nov. 22, 2018

Related U.S. Application Data

(60) Provisional application No. 62/507,166, filed on May 16, 2017.

(51) Int. Cl.
G01N 33/68 (2006.01)

(52) U.S. Cl.
CPC ..... *G01N 33/6896* (2013.01); *G01N 2333/47* (2013.01); *G01N 2333/4709* (2013.01); *G01N 2800/2821* (2013.01)

(58) Field of Classification Search
None
See application file for complete search history.

(56) References Cited

U.S. PATENT DOCUMENTS

| | | | |
|---|---|---|---|
| 7,351,526 B2 | 4/2008 | Soto | |
| 8,632,776 B2 | 1/2014 | Nordstroem et al. | |
| 9,910,049 B2 | 3/2018 | Soto et al. | |
| 2005/0064505 A1 | 3/2005 | Soto-Jara et al. | |
| 2005/0176078 A1 | 8/2005 | Allsop et al. | |
| 2006/0263767 A1 | 11/2006 | Castrillon et al. | |
| 2007/0218491 A1 | 9/2007 | Vasan et al. | |
| 2008/0118938 A1 | 5/2008 | Estrada et al. | |
| 2009/0163594 A1 | 6/2009 | Shapiro et al. | |
| 2011/0166035 A1 | 7/2011 | Kleinschmidt et al. | |
| 2013/0289022 A1 | 10/2013 | Ringe et al. | |
| 2015/0309054 A1 | 10/2015 | Diamond et al. | |
| 2016/0077111 A1 | 3/2016 | Soto et al. | |
| 2016/0077112 A1 | 3/2016 | Soto et al. | |
| 2017/0146556 A1 | 5/2017 | Luehrs | |

FOREIGN PATENT DOCUMENTS

| | | |
|---|---|---|
| WO | 2002004954 | 10/2002 |
| WO | 2014025905 | 2/2014 |
| WO | 2016040903 A1 | 3/2016 |

OTHER PUBLICATIONS

Meyer "amplification of tau fibrils from minute quantities of seeds" Biochem 53:5804-5809 (Year: 2014).*
Chen "Enhancement and destruction of antibody function by somatic mutation: unequal occurrence is controlled by V gene combinatorial associations" EMBO 14(12):2784-2794 (Year: 1995).*
Ramachandran "Understanding the Kinetic Roles of the Inducer Heparin and of Rod-like Protofibrils during Amyloid Fibril Formation by Tau Protein" Journal of Biological Chemistry vol. 286, No. 45, pp. 38948-38959 (Year: 2011).*
Sibille "Structural Impact of Heparin Binding to Full-Length Tau as Studied by NMR" Biochemistry 2006, 45, 12560-12572 (Year: 2006).*
Zhu "Quantitative Characterization of Heparin Binding to Tau Protein Implication for Inducer-Mediated Tau Filament Formation" Journal of Biological Chemistry vol. 285, No. 6, pp. 3592-3599, (Year: 2010).*
Garvey M et al. Phosphate and HEPES buffers potently affect the fibrillation and oligomerization mechanism of Alzheimer's Abeta peptide. Biochem Biophys Res Comm, 2011, 409: 385-388.
Jimenez S et al. Disruption of amyloid plaques integrity affects the soluble oligomers content from Alzheimer diseased brains. PLoS ONE, 2014, 9(12):e114041.
Padayachee ER et al. The novel effect of CFF and APOE4 on aggregation kinetics of Abeta42 in Alzheimer's disease. Alzheier's & Dementia, Jul. 10, 2014 (Suppl. 4):P511, Poster Abstract P2-108, Alzheimer's Association International Conference 2014.
Paravastu AK et al. Seeded growth of β-amyloid fibrils from Alzheimer's brain-derived fibrils produces a distinct fibril structure. Proc. Natl. Acad. Sci. USA, 2009, 106(18):7443-7448.
Schmidt M et al. Comparison of Alzheimer Abeta(1-40) and Abeta(1-42) amyloid fibrils reveals similar protofilament strucures. Proc Natl Acad Sci USA, 2009,106(47): 19813-19818.

(Continued)

*Primary Examiner* — Adam Weidner
(74) *Attorney, Agent, or Firm* — Kern Kendrick, LLC; Benjamen E. Kern

(57) ABSTRACT

Methods and kits are provided for amplifying and detecting misfolded tau protein from samples, for example, from patients having tauopathies such as Alzheimer's Disease, Progressive Supranuclear Palsy, and the like.

8 Claims, 27 Drawing Sheets

(56) References Cited

OTHER PUBLICATIONS

Castilla, et al. "Protein Misfolding Cyclic Amplification for Diagnosis and Prion Propagation Studies" Methods Enzymol, 2006, 412, 3-21.
Ghiso J. et al. Alzheimer's soluble amyloid beta is a normal component of human urine. FEBS Lett. 1997, 408:105-108.
Moreno-Gonzalez I et al. Misfolded protein aggregates: Mechanisms, structures and potential for disease transmission. Seminars Cell Dev. Biol. 2011, 22:482-487.
Salvadores N. et al. Detection of misfolded Abeta oligomers for sensitive biochemical diagnosis of Alzheimer's disease. Cell reports, Apr. 2014, 7: 261-268.
Windblad B et al. Active immunotherapy options for Alzheimer's disease. Alzheimer's Res. Therap. Jan. 2014, 6:7 (12 pages).
Zhou P et al. Immunoassays with protein misfolding cycle amplification; A platform for ultra sensitive detection of antigen. Analytical Chem. 2012, 84:7343-7349.
Roostaee A et al. Aggregation and Neurotoxicity of recombinant alpha-synuclein aggregates initiated by dimerization. Molecular Degeneration, 2013, 8:5.
Herva ME et al. Anti-amyloid compounds inhibit alpha-synuclein aggregation induced by protein misfolding cyclic amplification (PMCA). J. Biol. Chem. 289 (17): 11897-11905 (Apr. 2014).
International Preliminary Report on Patenability issued in PCT application No. PCT/US2015/049840 dated Mar. 14, 2017.
International Search Report and Written Opinion issued in PCT application No. PCT/US2015/049840 dated Feb. 2, 2016.
Atarashi et al. Simplified ultrasensitive prion detection by recombinant PRP conversion with shaking. Nature Methods Mar. 2005 vol 5. No. 3 pp. 211-212, Especially p. 211 fig 1.
International Preliminary Report on Patentability issued in PCT application No. PCT/US2015/049842 dated Mar. 14, 2017.
International Search Report and Written Opinion issued in PCT application No. PCT/US2015/049842 dated Feb. 2, 2016.
International Search Report and Written Opinion issued in PCT application No. PCT/US2015/049844 dated Feb. 5, 2016.
International Preliminary Report on Patentability issued in PCT application No. PCT/US2015/049844 dated Mar. 14, 2017.
International Search Report and Written Opinion issued in PCT application No. PCT/US18/32962, dated Sep. 26, 18.
M. Tolnay et al., "The Neuropathological Spectrum of Neurodegenerative Tauopathies", Taylor & Francis Health Sciences, 55(6), Jun. 2003, pp. 299-305.
J. Stöhr et al., "A 31-residue peptide induces aggregation of tau's microtubule-binding region in cells", Nature Chemistry, Apr. 3, 2017, 8 pgs.
G. Fairfoul et al., "Alpha-synuclein RT-QuIC in the CSF of patients with alpha-synucleinopathies". Annals of Clinical and Translational Neurology 2016; 3(10) pp. 812-818.
M. Shahnawaz et al., "Development of a Biochemical Diagnosis of Parkinson Disease by Detection of α-Synuclein Misfolded Aggregates in Cerebrospinal Fluid", JAMANeurology, 2017, 74(2): 163-172.
E. Saijo et al., "ultrasensitive and selective detection of 3-repeat tau seeding activity in Pick Disease brain and cerebrospinal fluid", Acta Neuropathol (2017) 113: 781-765.
C.M. Wischick et al., "Selective inhibition of Alzheimer disease-like tau aggregation by phenothiazlines". Proc. Natl., Acad. Sci. USA, vol. 93, Oct. 1996, pp. 11213-11218.
P. D. Dinkel, "Seeded Propagation of Tau Fibrils", University of Denver, Nov. 2013, 149 pgs.
A. L. Woerman, "Propagation of prions causing synucleinopathies in cultured cells", PNAS, Aug. 18, 2015, pp. E4949-E4958.
Office action issued in SOTO, U.S. Pat. No. 7,351,526; dated Apr. 13, 2007.
J. Narkiewics, et al., "In Vitro Aggregation Assays of α-Synuclein Prion-like Properties", Prion 8:1, 19-32; Jan./Feb. 2014.
M. E. van Raaij et al., "Concentration Dependence of α-Synuclein Fibril Length Assessed by Quantitative Atomic Force Microscopy and Statistical-Mechanical Theory", Biophysical Journal, vol. 95, Nov. 2008, pp. 4871-4878.
Chen et al., "Estimating prion concentration in fluids and tissues by quantitative PMCA", Nature Methods, vol. 7 No. 7, Epub May 30, 2010.
Saá et al.; "Ultra-efficient Replication of Infectious Prions by Automated Protein Misfolding Cyclic Amplification", J Biol Chemistry 281 (46): 35245-35252, Nov. 17, 2006, plus supplemental figure.
D'Castro, et al., "Isolation of Proteinase K-Sensitive Prions Using Pronase E and Phosphotungstic Acid" PLoS One, 2010, 5(12), e15679.
Onisko, et al., "Probing PrPSc Structure Using Chemical Cross-Linking and Mass Spectrometry: Evidence of the Proximity of Gly90 Amino Termini in the PrP 27-300 Aggregate" Biochemistry, 2005, 44, 10100-10109.
Deleault, et al. , "Formation of native prions from minimal components in vitro." Proc. Nat. Acad. Sci. 2007, 104, 9741-9746.
Atarashi, et al., "Real-time quaking-induced conversion—A highly sensitive assay for prion detection." Prion 2011, 5(3), 150-153.
Makeig, "Response: Event-related brain dynamics—unifying brain electrophysiology" TINS, vol. 25, 2002, pp. 390-394.
Saborio et al., "Sensitive detection of pathological prion protein by cyclic amplification of protein misfolding", Nature, vol. 411, 2001, pp. 810-813.
Written Opinion issued in PCT application No. PCT/US2018/032962 dated Aug. 21, 2019.
Non-Final Office Action issued in U.S. Appl. No. 14/852,475 dated Sep. 10, 2019.
Final Office Action issued in U.S. Appl. No. 14/852,475 dated Apr. 18, 2019.
Non-Final Office Action issued in U.S. Appl. No. 15/915,554 dated May 31, 2019.
Coalier KA et al. Stability of early-stage amyloid-beta (1-42) aggregation species. Biochimica et Biophysica Acta, 1834 (2013)65-70.
Klunk WE et al. Quantifying amyloid by Congo Red spectral shift assays. Methods Enzymology, 309 (1999), 285-286. (Year: 1999).
Non-Final Office Action issued in U.S. Appl. No. 16/414,749 dated Sep. 16, 2019.
Gill "acute plasma tau relates to prolonged return to play after concussion" neurology 88: 595-602 (Year: 2016).
Kanaan "Characterization of Early Pathological Tau Conformations and Phosphorylation in Chronic Traumatic Encephalopathy" J neuropath exp neurol 75(1): 19-34 (Year: 2016).
Buée et al., "Tau protein isoforms, phosphorylation and role in neurodegenerative disorders", Brain Res Brain Res Rev. 33(1), p. 95-130 (2000).
Schmitz, et al. "The real-time quaking-induced conversion assay for detection of human prion disease and study of other protein misfolding diseases", Nat Protoc. Nov. 2016; 11(11):2233-2242.
Examination Report issued in Canadian patent application No. 2,960,830, dated Jul. 16, 2019.
International Preliminary Report on Patentability issued in PCT Application No. PCT/US2018/032962, dated Nov. 22, 2019.
Final Office Action issued in U.S. Appl. No. 15/915,554 dated Nov. 22, 2019.
Non-Final Office Action issued in U.S. Appl. No. 16/233,848 dated Jan. 30, 2020.
Gonzalez-Montalban et al. "Highly Efficient Protein Misfolding Cyclic Amplification", PLoS Pathog. 2011 Fe; 7(2): e1001277 (Year: 2011).
International Search Report and Written Opinion Issued in PCT Application No. PCT/US2019/032749 dated Nov. 5, 2019.
Woerman et al. "Tau prions from Alzheimer's disease and chronic traumatic encephalopathy patients propagate in cultured cells," Proc Natl Acad Sci USA, Nov. 28, 2016 (Nov. 28, 2016), vol. 113, pp. E8187-E8196.
Saulle et al., "Chronic traumatic encephalopathy: a review," Rehabil Res Prac, Apr. 10, 2012, vol. 816069, pp. 1-10.

(56) References Cited

OTHER PUBLICATIONS

Edwards et al. "Amyloid-beta and tau pathology following repetitive mild traumatic brain injury,"Biochem Biophys Res Commun, Aug. 1, 2016, vol. 483, pp. 1137-1142.

* cited by examiner

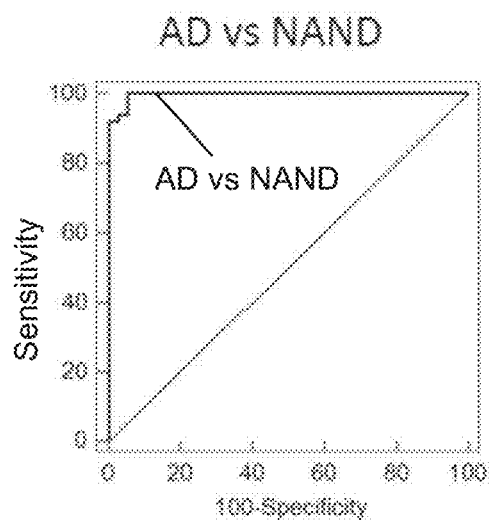
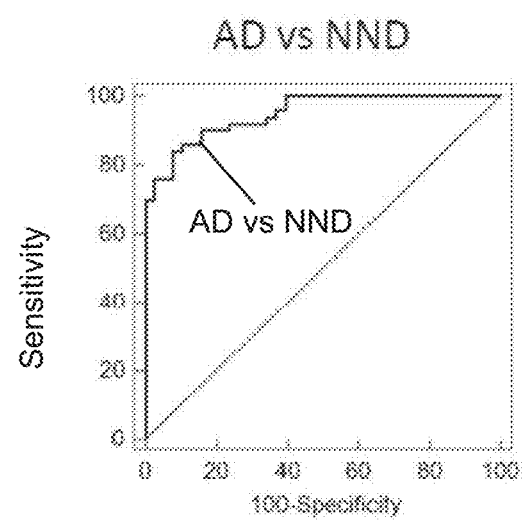
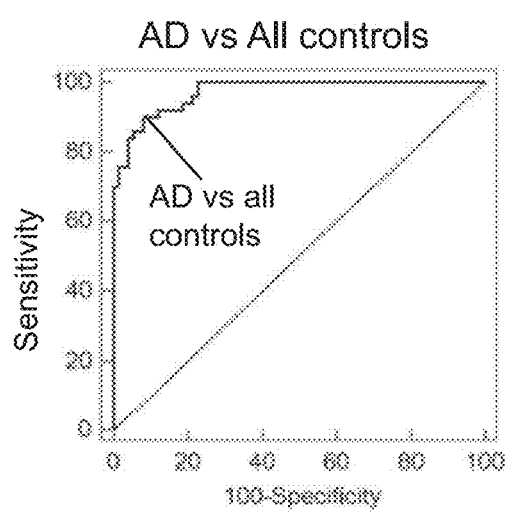
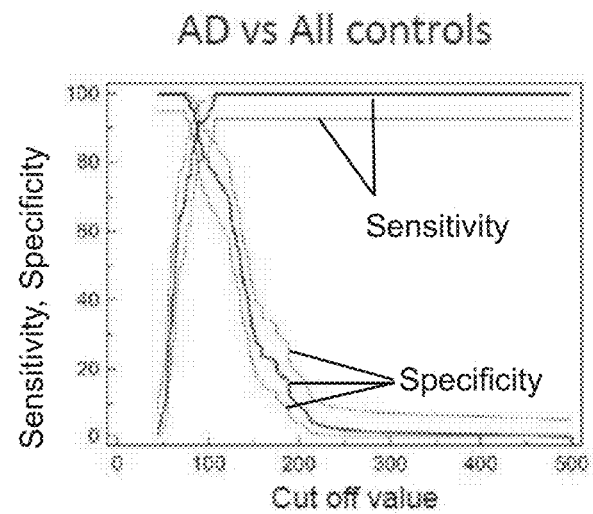
FIG. 4A
FIG. 4B
FIG. 4C
FIG. 4D
FIGS. 4A-D Table 1: Estimation of sensitivity, specificity, and predictive value for Aβ-PCMA in CSF[1]

| GROUPS | SENSITIVITY[2] | SPECIFICITY[2] | POSITIVE PREDICTIVE VALUE[2] | NEGATIVE PREDICTIVE VALUE[2] |
|---|---|---|---|---|
| AD vs NAND | 100.0% | 94.6% | 96.2% | 100.0% |
| AD vs NND | 90.0% | 84.2% | 88.2% | 86.5% |
| AD vs controls[3] | 90.0% | 92.0% | 88.2% | 93.2% |

1. For estimation of sensitivity, specificity and predictive value the results of the lag phase as shown in FIG. 9B were used. Cutoffs were estimated by Receiver Operating Characteristics (ROC) curve analysis using the MedCalc software.

2. Sensitivity was estimated by the formula: [True positives/(True positives + False negatives)] × 100; specificity was estimated by the formula: [True negatives/(False positives + True negatives)] × 100; positive predictive value was estimated by the formula: [True positives/(True positives + False positives)] × 100; negative predictive value was estimated by the formula: [True negatives/(True negatives + False negatives)] × 100

3. Controls refers to the samples from NND plus NAND.

FIG. 5

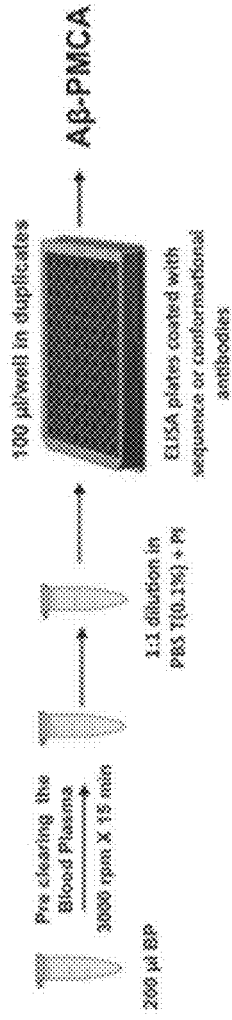
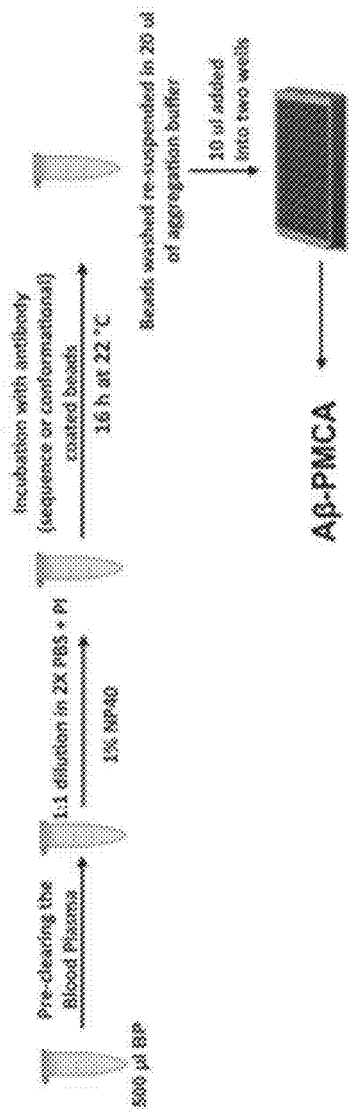
FIG. 8A
FIG. 8B

Table 2

| Antibody | Epitope | Commercial source | Aβ oligomer capturing capacity |
|---|---|---|---|
| 82E1 | 1-5 | IBL America | +++ |
| 4G8 | 18-22 | Covance | + |
| 6E10 | 3-8 | Covance | ++ |
| X-40/42 | C-terminal | Mybiosource | - |
| 16 ADV Mouse IgG1 | Conformational | Acumen | ++ |
| A11 | Conformational | Invitrogen | - |

+++ Best
++ very good
+ good
- no result

Table 3

| Antibodies (Company) | Epitope | Alpha-Synuclein oligomer capturing capacity |
|---|---|---|
| Alpha/beta-Synuclein Antibody N-19 (Santa Cruz Biotechnology) | N-terminal | +++ |
| Alpha-Synuclein Antibody C-20-R (Santa Cruz Biotechnology) | C-terminal | +++ |
| Alpha-Synuclein Antibody 211 (Santa Cruz Biotechnology) | Amino acids 121-125 | ++ |
| Alpha-synuclein Antibody Syn-204 (Santa Cruz Biotechnology) | Fragment 1-130 | + |
| 16 ADV Mouse IgG1 (Acumen) | Conformational | - |

+++     *Best*
++      *very good*
+       *good*
-       *no result*

FIG. 15

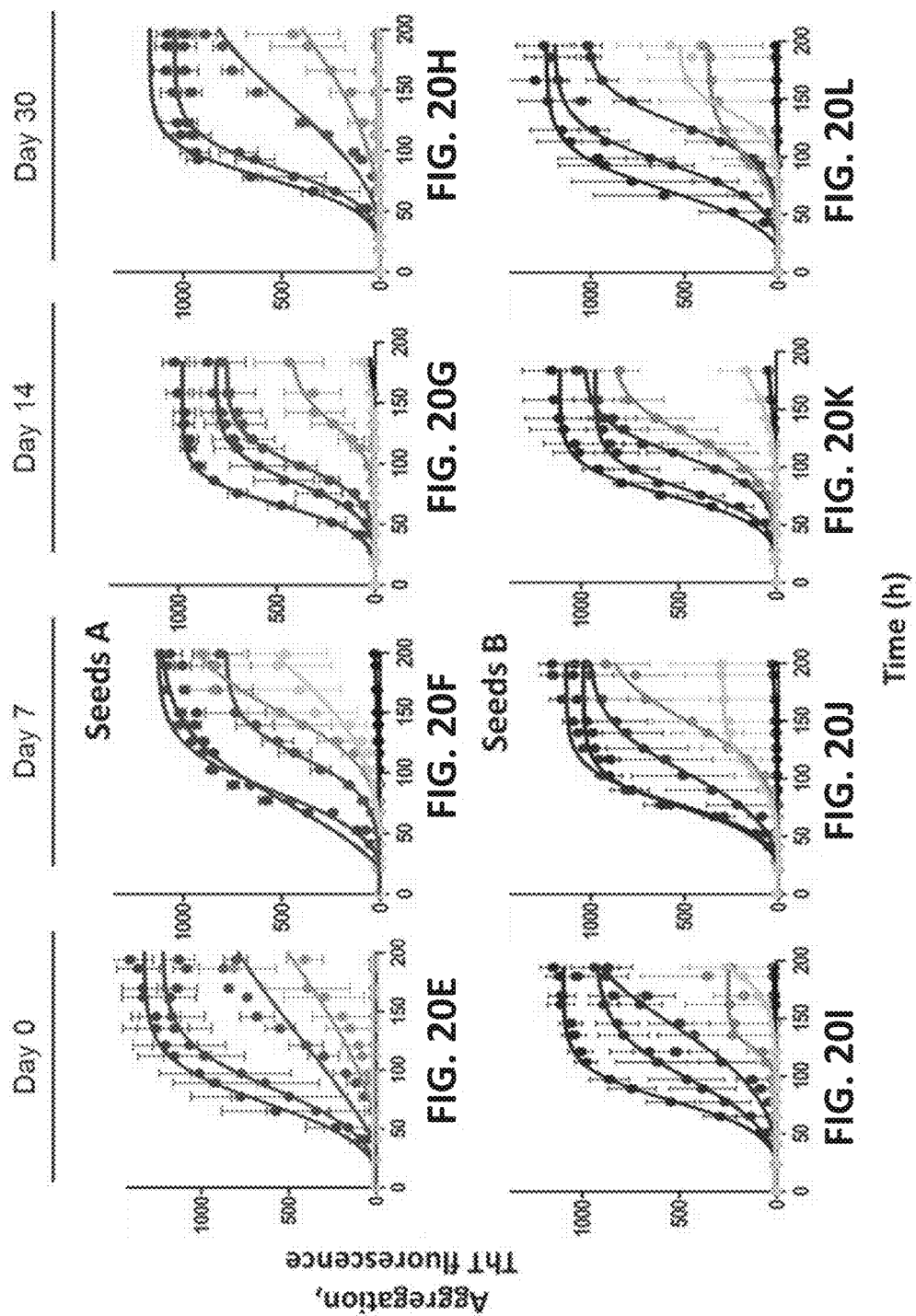

| Days | $T_{50} \pm$ s.e.m. (h) | | | | Average | P Value (ns) |
|---|---|---|---|---|---|---|
| | Seeds A | | Seeds B | | | |
| | Undiluted standard | Diluted standard | Undiluted standard | Diluted standard | | |
| Day 0 | 65 ± 5 | 78 ± 3 | 72 ± 6 | 65 ± 3 | 70 ± 3.1 | 0.19 |
| Day 7 | 69 ± 3 | 74 ± 2 | 74 ± 4 | 74 ± 8 | 72 ± 1.2 | 0.84 |
| Day 14 | 63 ± 4 | 75 ± 3 | 69 ± 3 | 63 ± 1 | 68 ± 2.9 | 0.06 |
| Day 30 | 74 ± 2 | 70 ± 7 | 88 ± 4 | 77 ± 3 | 77 ± 3.9 | 0.09 |
| Average | 67 ± 2.6 | 74 ± 1.6 | 75 ± 4.2 | 70 ± 3.4 | 71.5 ± 1.8 | |
| P value (ns) | 0.14 | 0.62 | 0.08 | 0.16 | | 0.26 |

FIG. 20M

DETECTION OF MISFOLDED TAU PROTEIN

CROSS-REFERENCE TO RELATED APPLICATIONS

This application claims priority from U.S. Provisional Patent Application No. 62/507,166, filed on May 16, 2017, the entire contents of which are incorporated herein by reference.

STATEMENT AS TO FEDERALLY SPONSORED RESEARCH

This invention was made with government support under AG049562 awarded by the National Institutes of Health. The government has certain rights in the invention.

BACKGROUND

Tauopathies may include, for example, Alzheimer's disease (AD), Parkinson's Disease (PD), Progressive Supranuclear Palsy (PSP), FrontoTemporal Dementia (FTD), Corticobasal degeneration (CBD), Mild cognitive impairment (MCI), Argyrophilic grain disease (AgD) Traumatic Brain Injury (TBI), Chronic Traumatic Encephalopathy (CTE), and Dementia Pugilistica (DP), and the like. Misfolded tau aggregates and fibrils may be formed and accumulate via nucleation and growth. The misfolded tau aggregates may induce cellular dysfunction and tissue damage, among other effects.

Real time quaking-induced conversion (RT-QuiC) has been shown to cause replication of 3-repeat (3R) tau isoforms from brain homogenate and cerebrospinal fluid samples drawn from Pick disease subjects, allowing sensitive detection of this rare disease and discrimination from other tauopathies. Surprisingly, however, for more common tauopathies of clinical importance that include misfolding of 4R tau, the efficacy of RT-QuiC was reduced by 3 to 5 orders of magnitude, rendering it ineffective and impractical for clinical and laboratory use. Such adverse results were obtained by seeding with brain samples containing predominant 4-repeat (4R) tau aggregates from cases of CBD, AgD, and FTDP-17, and PSP, as well as AD, a 4R+3R tauopathy. Some AD and PSP samples gave signals above the detection limit, but the signals were outliers and much weaker compared to Pick disease brain samples. Additionally, the AD and PSP samples which generated weak responses were not analyzed for contamination. The RT-QuiC analyses of 4R or 4R+3R tauopathies in general do not appear to be significantly different from controls using diseased subjects with no immunohistologically detected tau pathology. Such controls included diagnoses of senile change (SC), cerebrovascular disease (CVD), diffuse Lewy body disease (DLBD), frontotemporal dementia with TDP-43 (FTD-TDP), and amyotrophic lateral sclerosis (ALS). In sum, RT-QuiC analyses were shown to be generally ineffective and impractical for 4R tauopathies including 4R predominant and 4R+3R mixed tauopathies.

The present application appreciates that detection of misfolded tau protein, e.g., for diagnosis of related diseases, may be a challenging endeavor.

SUMMARY

In one embodiment, a method is provided for determining a presence or absence in a sample of a first misfolded protein aggregate. The method may include performing a first protein misfolding cyclic amplification (PMCA) procedure. The first PMCA procedure may include forming a first incubation mixture by contacting a first portion of the sample with a first substrate protein. The first substrate protein may include 4R tau protein. The first PMCA procedure may include conducting an incubation cycle two or more times under conditions effective to form as first amplified, misfolded protein aggregate. Each incubation cycle may include incubating the first incubation mixture effective to cause misfolding and/or aggregation of the first substrate protein in the presence of the first misfolded protein aggregate. Each incubation cycle may include disrupting the first incubation mixture effective to form the first amplified, misfolded protein aggregate. The first PMCA procedure may include determining the presence or absence in the sample of the first misfolded protein aggregate by analyzing the first incubation mixture for the presence or absence of the first amplified, misfolded protein aggregate. The first misfolded protein aggregate may include the first substrate protein. The first amplified, misfolded protein aggregate may include the first substrate protein.

In another embodiment, a method is provided for determining a presence or absence in a subject of a tauopathy corresponding to a first misfolded protein aggregate. The method may include providing a sample from the subject. The method may include performing at least a first PMCA procedure. The first PMCA procedure may include forming a first incubation mixture by contacting a first portion of the sample with a first substrate protein. The first substrate protein may include a tau isoform. The first substrate protein may be subject to pathological misfolding and/or aggregation in vivo to form the first misfolded protein aggregate. The first PMCA procedure may include conducting an incubation cycle two or more times under conditions effective to form a first amplified, misfolded protein aggregate. Each incubation cycle may include incubating the first incubation mixture effective to cause misfolding and/or aggregation of the first substrate protein in the presence of the first misfolded protein aggregate. Each incubation cycle may include disrupting the first incubation mixture effective to form the first amplified, misfolded protein aggregate. The first PMCA procedure may include determining the presence or absence in the sample of the first misfolded protein aggregate by analyzing the first incubation mixture for the presence or absence of the first amplified, misfolded protein aggregate. The first PMCA procedure may include determining the presence or absence of the tauopathy in the subject according the presence or absence of the first misfolded protein aggregate in the sample. The first misfolded protein aggregate may include the first substrate protein. The first amplified, misfolded protein aggregate may include the first substrate protein. The method may provide that the tauopathy excludes Pick's disease when the first substrate protein consists of monomeric 3R tau.

In one embodiment, a method is provided using capturing for determining a presence or absence in a sample of a first misfolded protein aggregate. The method may include capturing the first misfolded protein aggregate from the sample to form a captured first misfolded protein aggregate. The method may include performing at least a first PMCA procedure. The first PMCA procedure may include forming a first incubation mixture by contacting the captured first misfolded protein aggregate with a molar excess of a first substrate protein. The first substrate protein may be subject to pathological misfolding and/or aggregation in vivo to form the first misfolded protein aggregate. The molar excess may be greater than an amount of protein monomer included in the captured first misfolded protein aggregate. The method may include conducting an incubation cycle two or more times effective to form a first amplified, misfolded protein aggregate. Each incubation cycle may include incubating the first incubation mixture effective to cause misfolding and/or aggregation of the first substrate protein in the presence of the captured first misfolded protein aggregate. Each incubation cycle may include disrupting the first incubation mixture effective to form the first amplified, misfolded protein aggregate. The first PMCA procedure may include determining the presence or absence of the first misfolded protein aggregate in the sample by detecting the first amplified, misfolded protein aggregate. The first misfolded protein aggregate may include the first substrate protein. The first amplified, misfolded protein aggregate may include the first substrate protein.

In another embodiment, a method is provided for determining a presence or absence of a tauopathy in a subject, the tauopathy including Alzheimer's disease (AD). The method may include providing the subject. The method may include obtaining a sample from the subject. The sample may include one or more of: a bio-fluid, a biomaterial, a homogenized tissue, and a cell lysate. The method may include performing at least a first PMCA procedure. The first PMCA procedure may include forming a first incubation mixture by contacting the sample with a first substrate protein. The first substrate protein may include 4R tau. The first PMCA procedure may include conducting an incubation cycle two or more times effective to form a first amplified, misfolded protein aggregate. Each incubation cycle may include incubating the first incubation mixture effective to cause misfolding and/or aggregation of the first substrate protein in the presence of the first misfolded protein aggregate. Each incubation cycle may include disrupting the incubation mixture effective to form the first amplified, misfolded protein aggregate. The first PMCA procedure may include determining the presence or absence in the sample of the first misfolded protein aggregate by detecting in the first incubation mixture the presence or absence of the first amplified, misfolded protein aggregate. The method may include determining the presence or absence in the subject of AD according to the presence or absence of the first misfolded protein aggregate in the sample.

In one embodiment, a method is provided for determining a presence or absence of a tauopathy in a subject, the tauopathy including Parkinson's disease (PD). The method may include providing the subject. The method may include obtaining a sample from the subject. The sample may include one or more of: a bio-fluid, a biomaterial, a homogenized tissue, and a cell lysate. The method may include performing at least a first PMCA procedure. The first PMCA procedure may include forming a first incubation mixture by contacting the sample with a first substrate protein. The first substrate protein may include 4R tau. The first PMCA procedure may include conducting an incubation cycle two or more times effective to form a first amplified, misfolded protein aggregate. Each incubation cycle may include incubating the first incubation mixture effective to cause misfolding and/or aggregation of the first substrate protein in the presence of the first misfolded protein aggregate. Each incubation cycle may include disrupting the incubation mixture effective to form the first amplified, misfolded protein aggregate. The first PMCA procedure may include determining the presence or absence in the sample of the first misfolded protein aggregate by detecting in the first incubation mixture the presence or absence of the first amplified, misfolded protein aggregate. The method may include determining the presence or absence in the subject of PD according to the presence or absence of the first misfolded protein aggregate in the sample.

In another embodiment, a method is provided for determining a presence or absence of a tauopathy in a subject, the tauopathy including Progressive Supranuclear Palsy (PSP). The method may include providing the subject. The method may include obtaining a sample from the subject. The sample may include one or more of: a bio-fluid, a biomaterial, a homogenized tissue, and a cell lysate. The method may include performing at least a first PMCA procedure. The first PMCA procedure may include forming a first incubation mixture by contacting the sample with a first substrate protein. The first substrate protein may include 4R tau. The first PMCA procedure may include conducting an incubation cycle two or more times effective to form a first amplified, misfolded protein aggregate. Each incubation cycle may include incubating the first incubation mixture effective to cause misfolding and/or aggregation of the first substrate protein in the presence of the first misfolded protein aggregate. Each incubation cycle may include disrupting the incubation mixture effective to form the first amplified, misfolded protein aggregate. The first PMCA procedure may include determining the presence or absence in the sample of the first misfolded protein aggregate by detecting in the first incubation mixture the presence or absence of the first amplified, misfolded protein aggregate. The method may include determining the presence or absence in the subject of PSP according to the presence or absence of the first misfolded protein aggregate in the sample.

In one embodiment, a method is provided for determining a presence or absence of a tauopathy in a subject, the tauopathy including FrontoTemporal Dementia (FTD). The method may include providing the subject. The method may include obtaining a sample from the subject. The sample may include one or more of: a bio-fluid, a biomaterial, a homogenized tissue, and a cell lysate. The method may include performing at least a first PMCA procedure. The first PMCA procedure may include forming a first incubation mixture by contacting the sample with a first substrate protein. The first substrate protein may include 4R tau. The first PMCA procedure may include conducting an incubation cycle two or more times effective to form a first amplified, misfolded protein aggregate. Each incubation cycle may include incubating the first incubation mixture effective to cause misfolding and/or aggregation of the first substrate protein in the presence of the first misfolded protein aggregate. Each incubation cycle may include disrupting the incubation mixture effective to form the first amplified, misfolded protein aggregate. The first PMCA procedure may include determining the presence or absence in the sample of the first misfolded protein aggregate by detecting in the first incubation mixture the presence or absence of the first amplified, misfolded protein aggregate. The method may include determining the presence or absence in the subject of FTD according to the presence or absence of the first misfolded protein aggregate in the sample.

In another embodiment, a method is provided for determining a presence or absence of a tauopathy in a subject, the tauopathy including Corticobasal degeneration (CBD). The method may include providing the subject. The method may include obtaining a sample from the subject. The sample may include one or more of: a bio-fluid, a biomaterial, a homogenized tissue, and a cell lysate. The method may include performing at least a first PMCA procedure. The first PMCA procedure may include forming a first incubation mixture by contacting the sample with a first substrate protein. The first substrate protein may include 4R tau. The first PMCA procedure may include conducting an incubation cycle two or more times effective to form a first amplified, misfolded protein aggregate. Each incubation cycle may include incubating the first incubation mixture effective to cause misfolding and/or aggregation of the first substrate protein in the presence of the first misfolded protein aggregate. Each incubation cycle may include disrupting the incubation mixture effective to form the first amplified, misfolded protein aggregate. The first PMCA procedure may include determining the presence or absence in the sample of the first misfolded protein aggregate by detecting in the first incubation mixture the presence or absence of the first amplified, misfolded protein aggregate. The method may include determining the presence or absence in the subject of CBD according to the presence or absence of the first misfolded protein aggregate in the sample.

In one embodiment, a kit is provided for determining a presence or absence in a sample of a first misfolded protein aggregate. The kit may include a first substrate protein that may include 4R tau. The kit may include an indicator of the first misfolded protein aggregate. The first misfolded protein aggregate may include the first substrate protein. The first misfolded protein aggregate may correspond to a tauopathy. The kit may include a buffer. The kit may include heparin. The kit may include a salt. The kit may include instructions. The instructions may direct a user to obtain the sample. The instructions may direct the user to perform at least a first PMCA procedure. The first PMCA procedure may include forming a first incubation mixture by contacting a first portion of the sample with the first substrate protein, the indicator of the first misfolded protein aggregate, the buffer, the heparin, and the salt. The first incubation mixture may be formed with a concentration of one or more of: the first substrate protein of less than about 20 µM; the heparin of less than about 75 µM; the salt as NaCl of less than about 190 mM; and the indicator of the first misfolded protein aggregate as Thioflavin T of less than about 9.5 µM. The first PMCA procedure may include conducting an incubation cycle two or more times effective to form a first amplified, misfolded protein aggregate. Each incubation cycle may include incubating the first incubation mixture effective to cause misfolding and/or aggregation of the first substrate protein in the presence of the first misfolded protein aggregate. Each incubation cycle may include disrupting the incubation mixture effective to form the first amplified, misfolded protein aggregate. The instructions may direct the user to determine the presence or absence in the sample of the first misfolded protein aggregate by analyzing the first incubation mixture for the presence or absence of the first amplified, misfolded protein aggregate according to the indicator of the first misfolded protein aggregate.

BRIEF DESCRIPTION OF THE DRAWINGS

The accompanying figures, which are incorporated in and constitute a part of the specification, illustrate example methods and results, and are used merely to illustrate example embodiments.

FIGS. 4A-D are plots of the true positive rate (sensitivity) as a function of the false positive rate (specificity) for different cut-off points using the lag phase values showed in FIG. 3B for AD vs NAND (FIG. 4A), AD vs NND (FIG. 4B) and AD vs All control samples (FIG. 4C). FIG. 4D estimates the most reliable cut-off point for the different set of group comparisons.

FIG. 5, Table 1 shows estimations of the sensitivity, specificity and predictive value of the Aβ-PMCA test, calculated using the lag phase numbers.

FIG. 8A is a schematic representation of an ELISA solid phase method employed to capture Aβ oligomers from complex biological samples.

FIG. 8B is a schematic representation of a magnetic bead solid phase method employed to capture Aβ oligomers from complex biological samples.

FIG. 15, Table 3 demonstrates the ability of different sequence or conformational antibodies to capture αS oligomers.

FIG. 17A shows results with antibody N-19. FIG. 17B shows results with antibody 211. FIG. 17C shows results with antibody C-20.

FIG. 18A shows results in control samples. FIG. 18B shows results in PD patients. FIG. 18C shows results in patients with Multiple System Atrophy (MSA).

FIGS. 20E-20L are a series of graphs that display the aggregation results based on ThT fluorescence of 8 of the conditions tested, including 4 different time points (0, 7, 14 and 30 days) with samples subjected to freezing and thawing or not and in the presence of buffer or CSF.

FIG. 20E is a graph of aggregation based on ThT fluorescence of a first seed preparation at 0 days.

FIG. 20F is a graph of aggregation based on ThT fluorescence of a first seed preparation at 7 days.

FIG. 20G is a graph of aggregation based on ThT fluorescence of a first seed preparation at 14 days.

FIG. 20H is a graph of aggregation based on ThT fluorescence of a first seed preparation at 30 days.

FIG. 20I is a graph of aggregation based on ThT fluorescence of a second seed preparation at 0 days.

FIG. 20J is a graph of aggregation based on ThT fluorescence of a second seed preparation at 7 days.

FIG. 20K is a graph of aggregation based on ThT fluorescence of a second seed preparation at 14 days.

FIG. 20L is a graph of aggregation based on ThT fluorescence of a second seed preparation at 30 days.

FIG. 20M is a table of Tso values showing reproducibility across 16 different conditions.

DETAILED DESCRIPTION

Figure 1A:
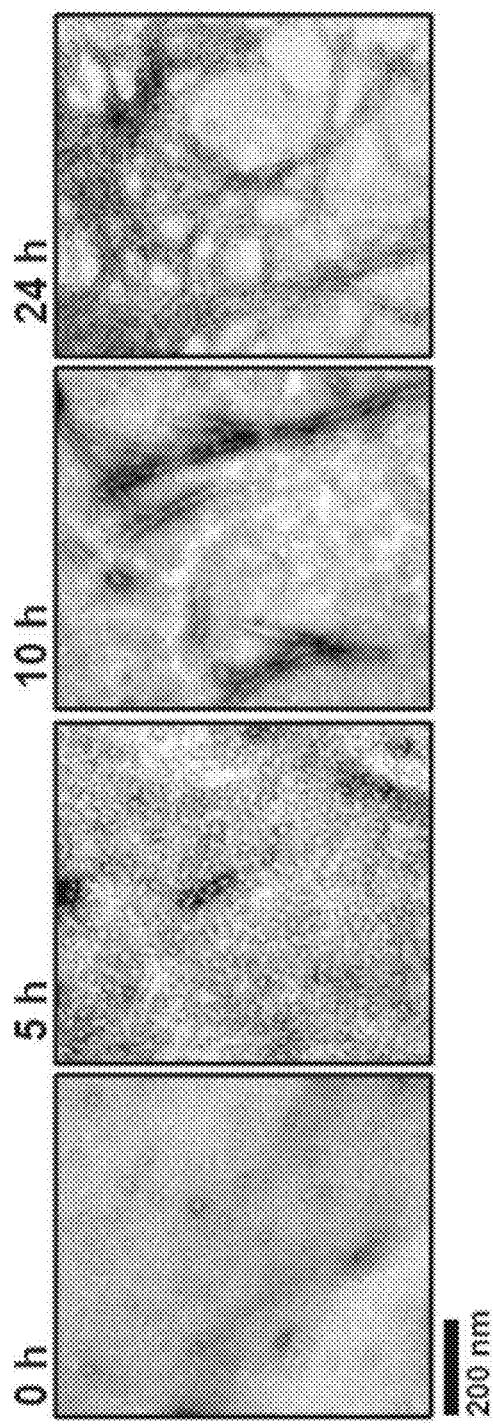
FIG. 1A shows electron micrographs taken at 1 h, 5 h, 10 h, and 24 h of incubation.

Methods and kits are provided for the detection or characterization of misfolded tau protein in a sample, including for the determination or diagnosis of tauopathies in a subject from which the sample is taken. Misfolded aggregates of tau proteins may be formed and accumulate. The misfolded aggregates may induce cellular dysfunction and tissue damage among other effects. For example, tauopathies may include those that predominantly regard misfolding of 4R, or misfolding of mixtures of 4R and 3R: Alzheimer's disease (AD), Parkinson's Disease (PD), Progressive Supranuclear Palsy (PSP), FrontoTemporal Dementia (FTD), Corticobasal degeneration (CBD), Mild cognitive impairment (MCI), Argyrophilic grain disease (AgD) Traumatic Brain Injury (TBI), Chronic Traumatic Encephalopathy (CTE), Dementia Pugilistica (DP), and the like.

In some embodiments, tauopathies herein may exclude Pick's disease. In some embodiments, the tauopathies described herein may exclude those that predominantly regard 3R tau misfolding, e.g., Pick's disease.

The methods may include protein misfolding cyclic amplification (PMCA), which may provide ultra-sensitive detection of misfolded protein aggregates such as tau through artificial acceleration and amplification of the misfolding and aggregation process in vitro. The basic concept of PMCA has been previously demonstrated experimentally for prions (Soto et al, WO 2002/04954; Estrada, et al., U.S. Pat. App. Pub. No. 20080118938, each of which is entirely incorporated herein by reference) and for other protein misfolding, such as of "Aβ" or "beta amyloid" in Alzheimer's disease and alpha synuclein in Parkinson's disease (Soto et al, WO 2016/040907, which is entirely incorporated herein by reference). However, prior to the filing date of the present document, no reference has described PCMA for the amplification and detection of misfolded tau protein corresponding to any tauopathy that predominantly regards misfolding of 4R, or that regards misfolding of 3R tau in the presence of 4R tau, or for any tauopathy other than Pick's disease. This document discloses specific examples and details which enable PMCA technology for the detecting the presence or absence of misfolded tau aggregates, and, in various embodiments, one or more additional PMCA procedures for the detection of other misfolded proteins such as misfolded Aβ in Alzheimer's disease and alpha synuclein in Parkinson's disease. Such one or more additional PMCA procedures may provide discrimination among the various tauopathies, for example, to distinguish AD and PD from each other and from PSP, FTD, CBD, MCI, AgD, TBI, CTE, DP, and the like.

As used herein, "Aβ" or "beta amyloid" refers to a peptide formed via sequential cleavage of the amyloid precursor protein (APP). Various Aβ isoforms may include 38-43 amino acid residues. The Aβ protein may be formed when APP is processed by β- and/or γ-secretases in any combination. The Aβ may be a constituent of amyloid plaques in brains of individuals suffering from or suspected of having AD. Various Aβ isoforms may include and are not limited to Abeta40 and Abeta42. Various Aβ peptides may be associated with neuronal damage associated with AD.

As used herein, "αS" or "alpha-synuclein" refers to full-length, 140 amino acid α-synuclein protein, e.g., "αS-140." Other isoforms or fragments may include "αS-126," alpha-synuclein-126, which lacks residues 41-54, e.g., due to loss of exon 3; and "αS-112" alpha-synuclein-112, which lacks residue 103-130, e.g., due to loss of exon 5. The αS may be present in brains of individuals suffering from PD or suspected of having PD. Various αS isoforms may include and are not limited to αS-140, αS-126, and αS-112. Various αS peptides may be associated with neuronal damage associated with PD.

As used herein, "tau" refers to proteins are the product of alternative splicing from a single gene, e.g., MAPT (microtubule-associated protein tau) in humans. Tau proteins include up to full-length and truncated forms of any of tau's isoforms. Various isoforms include, but are not limited to, the six tau isoforms known to exist in human brain tissue, which correspond to alternative splicing in exons 2, 3, and 10 of the tau gene. Three isoforms have three binding domains and the other three have four binding domains. Misfolded tau may be present in brains of individuals suffering from AD or suspected of having AD, or other tauopathies that, like AD, regard misfolding in the presence of both 4R and 3R tau isoforms. Misfolded tau may also be present in diseases that regard misfolding of primarily 4R tau isoforms, such as progressive supranuclear palsy (PSP), tau-dependent frontotemporal dementia (FTD), corticobasal degeneration (CBD), mild cognitive impairment (MCI), argyrophilic grain disease (AgD), and the like.

As used herein, a "misfolded protein aggregate" is a protein that contains in part or in full a structural conformation of the protein that differs from the structural conformation that exists when involved in its typical, non-pathogenic normal function within a biological system. A misfolded protein may aggregate. A misfolded protein may localize in a protein aggregate. A misfolded protein may be a non-functional protein. A misfolded protein may be a pathogenic conformer of the protein. Monomeric protein compositions may be provided in native, nonpathogenic conformations without the catalytic activity for misfolding, oligomerization, and aggregation associated with seeds (a misfolded protein oligomer capable of catalyzing misfolding under PMCA conditions). Monomeric protein compositions may be provided in seed-free form.

As used herein, "monomeric protein" refers to single protein molecules. "Soluble, aggregated misfolded protein" refers to oligomers or aggregations of monomeric protein that remain in solution. Examples of soluble, misfolded protein may include any number of protein monomers so long as the misfolded protein remains soluble. For example, soluble, misfolded protein may include monomers or aggregates of between 2 and about 50 units of monomeric protein.

Monomeric and/or soluble, misfolded protein may aggregate to form insoluble aggregates, higher oligomers, and/or tau fibrils. For example, aggregation of Aβ or tau protein may lead to protofibrils, fibrils, and eventually misfolded plaques or tangles that may be observed in AD or tauopathy subjects. "Seeds" or "nuclei" refer to misfolded protein or short fragmented fibrils, particularly soluble, misfolded protein with catalytic activity for further misfolding, oligomerization, and aggregation. Such nucleation-dependent aggregation may be characterized by a slow lag phase wherein aggregate nuclei may form, which may then catalyze rapid formation of further aggregates and larger oligomers and polymers. The lag phase may be minimized or removed by addition of pre-formed nuclei or seeds. Monomeric protein compositions may be provided without the catalytic activity for misfolding and aggregation associated with misfolded seeds. Monomeric protein compositions may be provided in seed-free form.

As used herein, "soluble" species may form a solution in biological fluids under physiological conditions, whereas "insoluble" species may be present as precipitates, fibrils, deposits, tangles, or other non-dissolved forms in such biological fluids under physiological conditions. Such biological fluids may include, for example, fluids, or fluids expressed from one or more of: amniotic fluid; bile; blood; cerebrospinal fluid; cerumen; skin; exudate; feces; gastric fluid; lymph; milk; mucus, e.g. nasal secretions; mucosal membrane, e.g., nasal mucosal membrane; peritoneal fluid; plasma; pleural fluid; pus; saliva; sebum; semen; sweat; synovial fluid; tears; urine; and the like. Insoluble species may include, for example, fibrils of Aβ, αS, 4R tau, 3R tau, combinations thereof such as 3R tau+4R tau, and the like. A species that dissolves in a non-biological fluid but not one of the aforementioned biological fluids under physiological conditions may be considered insoluble. For example, fibrils of Aβ, αS, 4R tau, 3R tau, combinations thereof such as 3R tau+4R tau, and the like may be dissolved in a solution of, e.g., a surfactant such as sodium dodecyl sulfate (SDS) in water, but may still be insoluble in one or more of the mentioned biological fluids under physiological conditions.

In some embodiments, the sample may exclude insoluble species of the misfolded proteins such as Aβ, αS, 4R tau, 3R tau, combinations thereof such as 3R tau+4R tau and the like as a precipitate, fibril, deposit, tangle, plaque, or other form that may be insoluble in one or more of the described biological fluids under physiological conditions.

For example, in some embodiments, the sample may exclude tau in fibril form. The sample may exclude misfolded tau proteins in insoluble form, e.g., the sample may exclude the misfolded tau proteins as precipitates, fibrils, deposits, tangles, plaques, or other insoluble forms, e.g., in fibril form. The methods described herein may include preparing the sample by excluding the misfolded protein in insoluble form, e.g., by excluding from the sample the misfolded tau protein as precipitates, fibrils, deposits, tangles, plaques, or other insoluble forms, e.g., in fibril form. The kits described herein may include instructions directing a user to prepare the sample by excluding from the sample the misfolded tau protein as precipitates, fibrils, deposits, tangles, plaques, or other insoluble forms, e.g., in fibril form. The exclusion of such insoluble forms of the described misfolded proteins from the sample may be substantial or complete.

As used herein, aggregates of misfolded protein refer to non-covalent associations of protein including soluble, misfolded protein. Aggregates of misfolded protein may be "de-aggregated", or disrupted to break up or release soluble, misfolded protein. The catalytic activity of a collection of soluble, misfolded protein seeds may scale, at least in part with the number of such seeds in a mixture. Accordingly, disruption of aggregates of misfolded protein in a mixture to release misfolded protein seeds may lead to an increase in catalytic activity for oligomerization or aggregation of monomeric protein.

In various embodiments, a method is provided for determining a presence or absence in a sample of a first misfolded protein aggregate. The method may include performing a first protein misfolding cyclic amplification (PMCA) procedure. The first PMCA procedure may include forming a first incubation mixture by contacting a first portion of the sample with a first substrate protein. The first substrate protein may include 4R tau protein. The first PMCA procedure may include conducting an incubation cycle two or more times under conditions effective to form as first amplified, misfolded protein aggregate. Each incubation cycle may include incubating the first incubation mixture effective to cause misfolding and/or aggregation of the first substrate protein in the presence of the first misfolded protein aggregate. Each incubation cycle may include disrupting the first incubation mixture effective to form the first amplified, misfolded protein aggregate. The first PMCA procedure may include determining the presence or absence in the sample of the first misfolded protein aggregate by analyzing the first incubation mixture for the presence or absence of the first amplified, misfolded protein aggregate. The first misfolded protein aggregate may include the first substrate protein. The first amplified, misfolded protein aggregate may include the first substrate protein.

In various embodiments, a method is provided for determining a presence or absence in a subject of a tauopathy corresponding to a first misfolded protein aggregate. The method may include providing a sample from the subject. The method may include performing at least a first PMCA procedure. The first PMCA procedure may include forming a first incubation mixture by contacting a first portion of the sample with a first substrate protein. The first substrate protein may include a tau isoform. The first substrate protein may be subject to pathological misfolding and/or aggregation in vivo to form the first misfolded protein aggregate. The first PMCA procedure may include conducting an incubation cycle two or more times under conditions effective to form a first amplified, misfolded protein aggregate. Each incubation cycle may include incubating the first incubation mixture effective to cause misfolding and/or aggregation of the first substrate protein in the presence of the first misfolded protein aggregate. Each incubation cycle may include disrupting the first incubation mixture effective to form the first amplified, misfolded protein aggregate. The first PMCA procedure may include determining the presence or absence in the sample of the first misfolded protein aggregate by analyzing the first incubation mixture for the presence or absence of the first amplified, misfolded protein aggregate. The first PMCA procedure may include determining the presence or absence of the tauopathy in the subject according the presence or absence of the first misfolded protein aggregate in the sample. The first misfolded protein aggregate may include the first substrate protein. The first amplified, misfolded protein aggregate may include the first substrate protein. The method may provide that the tauopathy excludes Pick's disease when the first substrate protein consists of monomeric 3R tau.

In various embodiments, a method is provided using capturing for determining a presence or absence in a sample of a first misfolded protein aggregate. The method may include capturing the first misfolded protein aggregate from the sample to form a captured first misfolded protein aggregate. The method may include performing at least a first PMCA procedure. The first PMCA procedure may include forming a first incubation mixture by contacting the captured first misfolded protein aggregate with a molar excess of a first substrate protein. The first substrate protein may be subject to pathological misfolding and/or aggregation in vivo to form the first misfolded protein aggregate. The molar excess may be greater than an amount of protein monomer included in the captured first misfolded protein aggregate. The method may include conducting an incubation cycle two or more times effective to form a first amplified, misfolded protein aggregate. Each incubation cycle may include incubating the first incubation mixture effective to cause misfolding and/or aggregation of the first substrate protein in the presence of the captured first misfolded protein aggregate. Each incubation cycle may include disrupting the first incubation mixture effective to form the first amplified, misfolded protein aggregate. The first PMCA procedure may include determining the presence or absence of the first misfolded protein aggregate in the sample by detecting the first amplified, misfolded protein aggregate. The first misfolded protein aggregate may include the first substrate protein. The first amplified, misfolded protein aggregate may include the first substrate protein.

In various embodiments, a method is provided for determining a presence or absence of a tauopathy in a subject, the tauopathy including Alzheimer's disease (AD). The method may include providing the subject. The method may include obtaining a sample from the subject. The sample may include one or more of: a bio-fluid, a biomaterial, a homogenized tissue, and a cell lysate. The method may include performing at least a first PMCA procedure. The first PMCA procedure may include forming a first incubation mixture by contacting the sample with a first substrate protein. The first substrate protein may include 4R tau. The first PMCA procedure may include conducting an incubation cycle two or more times effective to form a first amplified, misfolded protein aggregate. Each incubation cycle may include incubating the first incubation mixture effective to cause misfolding and/or aggregation of the first substrate protein in the presence of the first misfolded protein aggregate. Each incubation cycle may include disrupting the incubation mixture effective to form the first amplified, misfolded protein aggregate. The first PMCA procedure may include determining the presence or absence in the sample of the first misfolded protein aggregate by detecting in the first incubation mixture the presence or absence of the first amplified, misfolded protein aggregate. The method may include determining the presence or absence in the subject of AD according to the presence or absence of the first misfolded protein aggregate in the sample.

In some embodiments, determining the presence or absence in the subject of AD may include distinguishing AD from one or more additional tauopathies by determining a signature of AD tau protein aggregate. The signature AD tau protein aggregate may include one or more of: one or more AD-specific corresponding PMCA kinetic parameters of: lag phase, $T_{50}$, amplification rate, and amplification extent; an assay using an antibody selective for a conformational epitope of AD tau protein aggregate; an indicator selective for AD tau protein aggregate; and a spectrum characteristic of AD tau protein aggregate.

In various embodiments, a method is provided for determining a presence or absence of a tauopathy in a subject, the tauopathy including Parkinson's disease (PD). The method may include providing the subject. The method may include obtaining a sample from the subject. The sample may include one or more of: a bio-fluid, a biomaterial, a homogenized tissue, and a cell lysate. The method may include performing at least a first PMCA procedure. The first PMCA procedure may include forming a first incubation mixture by contacting the sample with a first substrate protein. The first substrate protein may include 4R tau. The first PMCA procedure may include conducting an incubation cycle two or more times effective to form a first amplified, misfolded protein aggregate. Each incubation cycle may include incubating the first incubation mixture effective to cause misfolding and/or aggregation of the first substrate protein in the presence of the first misfolded protein aggregate. Each incubation cycle may include disrupting the incubation mixture effective to form the first amplified, misfolded protein aggregate. The first PMCA procedure may include determining the presence or absence in the sample of the first misfolded protein aggregate by detecting in the first incubation mixture the presence or absence of the first amplified, misfolded protein aggregate. The method may include determining the presence or absence in the subject of PD according to the presence or absence of the first misfolded protein aggregate in the sample.

In some embodiments, determining the presence or absence in the subject of PD may include distinguishing PD from one or more additional tauopathies by determining a signature of PD tau protein aggregate. The signature PD tau protein aggregate may include one or more of: one or more PD-specific corresponding PMCA kinetic parameters of: lag phase, Tso, amplification rate, and amplification extent; an assay using an antibody selective for a conformational epitope of PD tau protein aggregate; an indicator selective for PD tau protein aggregate; and a spectrum characteristic of PD tau protein aggregate.

In various embodiments, a method is provided for determining a presence or absence of a tauopathy in a subject, the tauopathy including Progressive Supranuclear Palsy (PSP). The method may include providing the subject. The method may include obtaining a sample from the subject. The sample may include one or more of: a bio-fluid, a biomaterial, a homogenized tissue, and a cell lysate. The method may include performing at least a first PMCA procedure. The first PMCA procedure may include forming a first incubation mixture by contacting the sample with a first substrate protein. The first substrate protein may include 4R tau. The first PMCA procedure may include conducting an incubation cycle two or more times effective to form a first amplified, misfolded protein aggregate. Each incubation cycle may include incubating the first incubation mixture effective to cause misfolding and/or aggregation of the first substrate protein in the presence of the first misfolded protein aggregate. Each incubation cycle may include disrupting the incubation mixture effective to form the first amplified, misfolded protein aggregate. The first PMCA procedure may include determining the presence or absence in the sample of the first misfolded protein aggregate by detecting in the first incubation mixture the presence or absence of the first amplified, misfolded protein aggregate. The method may include determining the presence or absence in the subject of PSP according to the presence or absence of the first misfolded protein aggregate in the sample.

In some embodiments, determining the presence or absence in the subject of PSP may include distinguishing PSP from one or more additional tauopathies by determining a signature of PSP tau protein aggregate. The signature PSP tau protein aggregate may include one or more of: one or more PSP-specific corresponding PMCA kinetic parameters of: lag phase, $T_{50}$, amplification rate, and amplification extent; an assay using an antibody selective for a conformational epitope of PSP tau protein aggregate; an indicator selective for PSP tau protein aggregate; and a spectrum characteristic of PSP tau protein aggregate.

In various embodiments, a method is provided for determining a presence or absence of a tauopathy in a subject, the tauopathy including FrontoTemporal Dementia (FTD). The method may include providing the subject. The method may include obtaining a sample from the subject. The sample may include one or more of: a bio-fluid, a biomaterial, a homogenized tissue, and a cell lysate. The method may include performing at least a first PMCA procedure. The first PMCA procedure may include forming a first incubation mixture by contacting the sample with a first substrate protein. The first substrate protein may include 4R tau. The first PMCA procedure may include conducting an incubation cycle two or more times effective to form a first amplified, misfolded protein aggregate. Each incubation cycle may include incubating the first incubation mixture effective to cause misfolding and/or aggregation of the first substrate protein in the presence of the first misfolded protein aggregate. Each incubation cycle may include disrupting the incubation mixture effective to form the first amplified, misfolded protein aggregate. The first PMCA procedure may include determining the presence or absence in the sample of the first misfolded protein aggregate by detecting in the first incubation mixture the presence or absence of the first amplified, misfolded protein aggregate. The method may include determining the presence or absence in the subject of FTD according to the presence or absence of the first misfolded protein aggregate in the sample.

In some embodiments, determining the presence or absence in the subject of FTD may include distinguishing FTD from one or more additional tauopathies by determining a signature of FTD tau protein aggregate. The signature FTD tau protein aggregate may include one or more of: one or more FTD-specific corresponding PMCA kinetic parameters of: lag phase, $T_{50}$, amplification rate, and amplification extent; an assay using an antibody selective for a conformational epitope of FTD tau protein aggregate; an indicator selective for FTD tau protein aggregate; and a spectrum characteristic of FTD tau protein aggregate.

In various embodiments, a method is provided for determining a presence or absence of a tauopathy in a subject, the tauopathy including Corticobasal degeneration (CBD). The method may include providing the subject. The method may include obtaining a sample from the subject. The sample may include one or more of: a bio-fluid, a biomaterial, a homogenized tissue, and a cell lysate. The method may include performing at least a first PMCA procedure. The first PMCA procedure may include forming a first incubation mixture by contacting the sample with a first substrate protein. The first substrate protein may include 4R tau. The first PMCA procedure may include conducting an incubation cycle two or more times effective to form a first amplified, misfolded protein aggregate. Each incubation cycle may include incubating the first incubation mixture effective to cause misfolding and/or aggregation of the first substrate protein in the presence of the first misfolded protein aggregate. Each incubation cycle may include disrupting the incubation mixture effective to form the first amplified, misfolded protein aggregate. The first PMCA procedure may include determining the presence or absence in the sample of the first misfolded protein aggregate by detecting in the first incubation mixture the presence or absence of the first amplified, misfolded protein aggregate. The method may include determining the presence or absence in the subject of CBD according to the presence or absence of the first misfolded protein aggregate in the sample.

In some embodiments, determining the presence or absence in the subject of CBD may include distinguishing CBD from one or more additional tauopathies by determining a signature of CBD tau protein aggregate. The signature CBD tau protein aggregate may include one or more of: one or more CBD-specific corresponding PMCA kinetic parameters of: lag phase, $T_{50}$, amplification rate, and amplification extent; an assay using an antibody selective for a conformational epitope of CBD tau protein aggregate; an indicator selective for CBD tau protein aggregate; and a spectrum characteristic of CBD tau protein aggregate.

In further embodiments, each of the methods described herein above may incorporate one or more of the following features. In particular, each feature described with reference to any protein substrate, misfolded protein aggregate, amplified misfolded protein aggregate, incubation mixture, PMCA procedure, portion of the sample, and the like, should be understood to describe, independently selected in various other embodiments, any other protein substrate, misfolded protein aggregate, amplified misfolded protein aggregate, incubation mixture, PMCA procedure, portion of the sample, and the like. For example, features described for a "first" protein substrate may, in some embodiments, also be independently selected to describe a "second" protein substrate; features described for a "first" misfolded protein aggregate may also be independently selected to describe a "second" misfolded protein aggregate; features described for a "first" incubation mixture may also be independently selected to describe a "second" incubation mixture; features described for a "first" PMCA procedure may also be independently selected to describe a "second" PMCA procedure; and the like. Further, for example, features described with reference to "each" protein substrate, misfolded protein aggregate, amplified misfolded protein aggregate, incubation mixture, PMCA procedure, portion of the sample, and the like, should be understood to describe, independently selected in various other embodiments, any other enumerated element, e.g., "first," "second," "third," and the like, as applied to the protein substrate, misfolded protein aggregate, amplified misfolded protein aggregate, incubation mixture, PMCA procedure, portion of the sample, and the like. For example, a description with reference to "each substrate protein" may be independently selected to describe and support recitations of a "first substrate protein," a "second substrate protein," a "third substrate protein," and the like.

In several embodiments, features described generally for enumerated or specified elements, e.g., "first," "second," "each," and the like, may be independently selected to be the same or distinct. For example, in some embodiments, a first substrate protein may include a 4R tau and a second substrate protein may include Aβ; a condition such as a temperature may be selected independently for a first and second PMCA procedure, and the like. In several embodiments, some features described generally for such first and second elements may be selected to be the same, or to overlap, while other features described generally for such first and second elements may be independently selected to be distinct. For example, in some embodiments, first and second portions of the sample may be the same or combined, and first and second incubation mixtures may be the same or combined, while corresponding first and second PMCA procedures may be conducted in parallel or in series in the combined incubation mixture using different first and second substrate proteins, e.g., 4R tau and Aβ.

In several embodiments, one, two, or more instances may be independently selected for each protein substrate, misfolded protein aggregate, amplified misfolded protein aggregate, incubation mixture, PMCA procedure, portion of the sample, and the like. For example, various method embodiments may include a first PMCA procedure using 4R tau as a first substrate protein, a second PMCA procedure using Aβ as a second substrate protein, a third PMCA procedure using alpha synuclein as a third substrate protein, a fourth PMCA procedure using 3R tau as a fourth substrate protein, and the like. Such multiple PMCA procedures may be performed for a sample, e.g., a laboratory sample, or a sample drawn from a subject, such as a subject having a tauopathy. Such multiple PMCA procedures may be performed in parallel for each protein substrate, misfolded protein aggregate, amplified misfolded protein aggregate, incubation mixture, PMCA procedure, portion of the sample, and the like, for example as follows.

In various embodiments, the method may include determining the presence in the sample of the first misfolded protein aggregate. The method may include performing at least a second PMCA procedure to determine the presence or absence in the sample of at least a second misfolded protein aggregate. The second PMCA procedure may include forming a second incubation mixture by contacting a second portion of the sample with a second substrate protein. The second substrate protein may be subject to pathological misfolding and/or aggregation in vivo to form the second misfolded protein aggregate. The second PMCA procedure may include conducting an incubation cycle two or more times under conditions effective to form a second amplified, misfolded protein aggregate. Each incubation cycle may include incubating the second incubation mixture effective to cause misfolding and/or aggregation of the second substrate protein in the presence of the second misfolded protein aggregate. Each incubation cycle may include disrupting the second incubation mixture effective to form the second amplified, misfolded protein aggregate. The second PMCA procedure may include determining the presence or absence in the sample of the second misfolded protein aggregate by analyzing the second incubation mixture for the presence or absence of the second amplified, misfolded protein aggregate. The second misfolded protein aggregate may include the second substrate protein. The second amplified, misfolded protein aggregate may include the second substrate protein.

In some embodiments, the method may include determining the presence in the sample of the first misfolded protein aggregate and the second misfolded protein aggregate. The method may include performing at least a third PMCA procedure to determine the presence or absence in the sample of at least a third misfolded protein aggregate. The third PMCA procedure may include forming a third incubation mixture by contacting a third portion of the sample with a third substrate protein. The third substrate protein may be subject to pathological misfolding and/or aggregation in vivo to form the third misfolded protein aggregate. The third PMCA procedure may include conducting an incubation cycle two or more times under conditions effective to form a third amplified, misfolded protein aggregate. Each incubation cycle may include incubating the third incubation mixture effective to cause misfolding and/or aggregation of the third substrate protein in the presence of the third misfolded protein aggregate. Each incubation cycle may include disrupting the third incubation mixture effective to form the third amplified, misfolded protein aggregate. The third PMCA procedure may include determining the presence or absence in the sample of the third misfolded protein aggregate by analyzing the third incubation mixture for the presence or absence of the third amplified, misfolded protein aggregate. The third misfolded protein aggregate may include the third substrate protein. The third amplified, misfolded protein aggregate may include the third substrate protein.

In several embodiments, the method may include determining the presence in the sample of the first misfolded protein aggregate, the second misfolded protein aggregate, and the fourth misfolded protein aggregate. The method may include performing at least a fourth PMCA procedure to determine the presence or absence in the sample of a fourth misfolded protein aggregate. The fourth PMCA procedure may include forming a fourth incubation mixture by contacting a fourth portion of the sample with a fourth substrate protein. The fourth substrate protein may be subject to pathological misfolding and/or aggregation in vivo to form the fourth misfolded protein aggregate. The fourth PMCA procedure may include conducting an incubation cycle two or more times under conditions effective to form a fourth amplified, misfolded protein aggregate. Each incubation cycle may include incubating the fourth incubation mixture effective to cause misfolding and/or aggregation of the fourth substrate protein in the presence of the fourth misfolded protein aggregate. Each incubation cycle may include disrupting the fourth incubation mixture effective to form the fourth amplified, misfolded protein aggregate. The fourth PMCA procedure may include determining the presence or absence in the sample of the fourth misfolded protein aggregate by analyzing the fourth incubation mixture for the presence or absence of the fourth amplified, misfolded protein aggregate. The fourth misfolded protein aggregate may include the fourth substrate protein. The fourth amplified, misfolded protein aggregate may include the fourth substrate protein.

In various embodiments, the first substrate protein may independently include a tau isoform, e.g., 3R tau, 4R tau, and the like. In several embodiments, the first substrate protein may include 4R tau. The first substrate protein may include 3R tau. The first substrate protein may exclude 3R tau, for example, when the sample corresponds to Pick's disease or is drawn from a subject having Pick's disease. The first substrate protein may be soluble. The first substrate protein may be monomeric. The first substrate protein may be in a native in vivo conformation, e.g., folded. The first substrate protein may be distinct from each other substrate protein.

In various embodiments, the second substrate protein may independently include one of: a tau isoform, e.g., 3R tau, 4R tau, and the like; Aβ, alpha synuclein, and the like. The second substrate protein may include one of: 3R tau, Aβ, alpha synuclein, and the like. The second substrate protein may include 3R tau. The second substrate protein may include Aβ. The second substrate protein may include alpha synuclein. The second substrate protein may consist essentially of, or consist of, one of: 3R tau, 4R tau, Aβ, or alpha synuclein. The second substrate protein may be soluble. The second substrate protein may be monomeric. The second substrate protein may be in a native in vivo conformation, e.g., folded. The second substrate protein may be distinct from each other substrate protein.

In various embodiments, the third substrate protein may independently include one of: a tau isoform, e.g., 3R tau, 4R tau, and the like; Aβ, alpha synuclein, and the like. The third substrate protein may include one of: 3R tau, Aβ, alpha synuclein, and the like. The third substrate protein may include 3R tau. The third substrate protein may include Aβ. The third substrate protein may include alpha synuclein. The third substrate protein may consist essentially of, or consist of, one of: 3R tau, 4R tau, Aβ, or alpha synuclein. The third substrate protein may be soluble. The third substrate protein may be monomeric. The third substrate protein may be in a native in vivo conformation, e.g., folded. The third substrate protein may be distinct from each other substrate protein.

In various embodiments, the fourth substrate protein may independently include one of: a tau isoform, e.g., 3R tau, 4R tau, and the like; Aβ, alpha synuclein, and the like. The fourth substrate protein may include one of: 3R tau, Aβ, alpha synuclein, and the like. The fourth substrate protein may include 3R tau. The fourth substrate protein may include Aβ. The fourth substrate protein may include alpha synuclein. The fourth substrate protein may consist essentially of, or consist of, one of: 3R tau, 4R tau, Aβ, or alpha synuclein. The fourth substrate protein may be soluble. The fourth substrate protein may be monomeric. The fourth substrate protein may be in a native in vivo conformation, e.g., folded. The fourth substrate protein may be distinct from each other substrate protein.

In some embodiments the sample may be taken from a subject. The method may include determining or diagnosing the presence or absence of a tauopathy in the subject according to the presence or absence of the first misfolded protein aggregate in the sample.

In several embodiments, the method may include performing at least a second PMCA procedure to determine the presence or absence in the sample of second misfolded protein aggregate, e.g., a misfolded protein aggregate that includes a second substrate protein. The second PMCA procedure may include forming a second incubation mixture by contacting a second portion of the sample with a second substrate protein. The second substrate protein may be subject to pathological misfolding and/or aggregation in vivo to form the second misfolded protein aggregate. The methods may include determining the presence or absence in the sample of the second misfolded protein aggregate by analyzing the second incubation mixture for the presence or absence of the second amplified, misfolded protein aggregate. The second misfolded protein aggregate may include the second substrate protein. The second amplified, misfolded protein aggregate may include the second substrate protein. The second substrate protein may include one of: amyloid-beta (Aβ), alpha synuclein, and 3R tau.

In some embodiments, the sample may be taken from a subject. The methods may include determining or diagnosing the presence or absence of a tauopathy in the subject according to the presence or absence of the first misfolded protein aggregate in the sample. The methods may include performing at least a second PMCA procedure to determine the presence or absence in the sample of a second misfolded protein aggregate. The second PMCA procedure may include forming a second incubation mixture by contacting a second portion of the sample with a second substrate protein. The second substrate protein may be subject to pathological misfolding and/or aggregation in vivo to form the second misfolded protein aggregate. The second PMCA procedure may include conducting an incubation cycle two or more times under conditions effective to form a second amplified, misfolded protein aggregate. Each incubation cycle may include incubating the second incubation mixture effective to cause misfolding and/or aggregation of the second substrate protein in the presence of the second misfolded protein aggregate. Each incubation cycle may include disrupting the second incubation mixture effective to form the second amplified, misfolded protein aggregate. The second PMCA procedure may include determining the presence or absence in the sample of the second misfolded protein aggregate by analyzing the second incubation mixture for the presence or absence of the second amplified, misfolded protein aggregate. The second misfolded protein aggregate may include the second substrate protein. The second amplified, misfolded protein aggregate may include the second substrate protein.

In various embodiments, the subject may have the tauopathy. The methods may include characterizing an identity of the tauopathy in the subject according to: the presence in the sample of the first misfolded protein aggregate; and the presence or absence in the sample of the second misfolded protein aggregate. The second substrate protein may include one of: amyloid-beta (Aβ), alpha synuclein, and 3R tau. For example, the presence of misfolded 4R tau aggregate as the first misfolded protein aggregate and Aβ as the second misfolded protein aggregate may indicate the tauopathy in the subject is AD; the presence of misfolded 4R tau aggregate as the first misfolded protein aggregate and alpha synuclein as the second misfolded protein aggregate may indicate the tauopathy in the subject is PD; the presence of misfolded 4R tau aggregate as the first misfolded protein aggregate and the absence of the second misfolded protein aggregate including Aβ, alpha synuclein, or 3R may indicate a 4R tauopathy, such as PSP, CBD, AGD, and the like.

In various embodiments, the tauopathy may include a primary tauopathy or a secondary tauopathy. The tauopathy may be characterized at least in part by misfolding and/or aggregation of 4R tau protein. The tauopathy may be characterized at least in part by misfolding and/or aggregation of 4R tau protein and 3R tau protein. The tauopathy may be characterized at least in part by misfolded and/or aggregated 4R tau protein, in a ratio to misfolded and/or aggregated 3R tau protein, of one of about: 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, and 99:1, or a range between any two of the preceding ratios, for example, between 1:99 and 99:1.

In several embodiments, the methods may include characterizing an identity of the tauopathy by analyzing the first amplified, misfolded protein aggregate or one or more corresponding PMCA kinetic parameters thereof for a signature of at least one of: Alzheimer's disease (AD), Parkinson's Disease (PD), Progressive Supranuclear Palsy (PSP), FrontoTemporal Dementia (FTD), Corticobasal degeneration (CBD), Mild cognitive impairment (MCI), Argyrophilic grain disease (AgD) Traumatic Brain Injury (TBI), Chronic Traumatic Encephalopathy (CTE), and Dementia Pugilistica (DP). For example, characterizing the identity of the tauopathy may include determining the one or more corresponding PMCA kinetic parameters, including one or more of: lag phase, $T_{50}$, amplification rate, and amplification extent. Characterizing the identity of the tauopathy may include comparing the one or more corresponding PMCA kinetic parameters to one or more corresponding predetermined corresponding PMCA kinetic parameters that are characteristic of the identity of the tauopathy to determine a similarity or difference effective to characterize the identity of the tauopathy.

In some embodiments, the methods may include characterizing the identity of the tauopathy using an antibody selective for a conformational epitope of a tauopathy-specific misfolded tau protein aggregate. The methods may include characterizing the identity of the tauopathy using an indicator selective for each tauopathy-specific misfolded tau protein aggregate. The indicator selective for each tauopathy-specific misfolded tau protein aggregate may include a small molecule, a peptide, or a DNA or RNA aptamer; and the like. The methods may include characterizing the identity of the tauopathy using a spectrum characteristic of each tauopathy-specific misfolded tau protein aggregate.

In some embodiments, the methods may include, for example, characterizing the identity of the tauopathy by analyzing the proteolytic resistance of each tauopathy-specific misfolded tau protein aggregate. For example, each tauopathy-specific misfolded tau protein aggregate may be contacted with a proteinase, e.g., proteinase K, trypsin, chymotrypsin, and the like, at a proteinase concentration of from 0.1 to 5000 μg/mL, at various temperatures from 20° C. to 120° C. and for various times, e.g., from 1 min to 4 h. The proteolytic resistance of each tauopathy-specific misfolded tau protein aggregate may be characterized and used to distinguish the various tauopathy-specific misfolded tau protein aggregates.

In several embodiments, the methods may include characterizing the identity of the tauopathy by analyzing the stability to denaturation of each tauopathy-specific misfolded tau protein aggregate. For example, each tauopathy-specific misfolded tau protein aggregate may be treated with guanidinium or urea at a sufficiently elevated temperature to induce protein denaturation of each tauopathy-specific misfolded tau protein aggregate. The concentration of guanidinium or urea may range from 0.1 M to 8 M. The temperature may range between 20° C. to 120° C. The stability of each tauopathy-specific misfolded tau protein aggregate may be characterized and used to distinguish the various tauopathy-specific misfolded tau protein aggregates.

The methods may include sedimentation of each tauopathy-specific misfolded tau protein aggregate. The methods may include gel chromatography to characterize the size of each tauopathy-specific misfolded tau protein aggregate. The methods may include circular dichroism spectroscopy of each tauopathy-specific misfolded tau protein aggregate. The methods may include Fourier transform infrared spectroscopy to analyze secondary structure of each tauopathy-specific misfolded tau protein aggregate. The methods may include nuclear magnetic resonance spectroscopy to analyze structure of each tauopathy-specific misfolded tau protein aggregate. The methods may include mass spectrometry, e.g., fragmentation and collision induced dissociation to analyze secondary and tertiary structure of each tauopathy-specific misfolded tau protein aggregate. The methods may include microscopy, e.g., atomic force microscopy, cryo-electron microscopy, and the like to analyze morphology of each tauopathy-specific misfolded tau protein aggregate. Each of these methods may be coupled with substitution using atomic isotopes of different mass, magnetic properties, and/or isotopic stability to complement the methods; for example, nuclear magnetic resonance spectroscopy may be coupled with deuterium exchange in each tauopathy-specific misfolded tau protein aggregate to obtain structural information.

In various embodiments, the methods are provided such that the tauopathy specifically excludes Pick's disease. In various embodiments, the exclusion of Pick's disease does not encompass the remainder of Pick's complex of diseases.

In several embodiments, the methods may include determining or diagnosing the presence or absence of a tauopathy in the subject including comparing the presence or absence of the first misfolded protein aggregate in the sample to a control sample taken from a control subject. The detecting may include detecting an amount of the first misfolded protein aggregate in the sample. The sample may be taken from a subject. The methods may include determining or diagnosing the presence or absence of a tauopathy in the subject by comparing the amount of the first misfolded protein aggregate in the sample to a predetermined threshold amount. The sample may be taken from a subject exhibiting no clinical signs of dementia according to cognitive testing. The methods may include determining or diagnosing the presence or absence of a tauopathy in the subject according to the presence or absence of the first misfolded protein aggregate in the sample. The sample may be taken from a subject exhibiting no cortex plaques or tangles according to contrast imaging. The methods may include determining or diagnosing the presence or absence of a tauopathy in the subject according to the presence or absence of the first misfolded protein aggregate in the sample. The sample may be taken from a subject exhibiting clinical signs of dementia according to cognitive testing. The methods may include determining or diagnosing the presence or absence of a tauopathy as a contributing factor to the clinical signs of dementia in the subject according to the presence or absence of the first misfolded protein aggregate in the sample. The sample may be taken from a subject exhibiting no clinical signs of dementia according to cognitive testing. The subject may exhibit a predisposition to dementia according to genetic testing. The genetic testing may indicate, for example, an increased risk of tauopathy according to one or two copies of the ApoE4 allele, variants of the brain derived neurotrophic factor (BDNF) gene, such as the val66met allele, in which valine at AA position 66 is replaced by methionine, and the like. The methods may include determining or diagnosing the presence or absence of a tauopathy in the subject according to the presence or absence of the first misfolded protein aggregate in the sample.

In some embodiments, the methods may include preparing the first incubation mixture characterized by at least one concentration of: the first substrate protein of less than about 20 µM; heparin of less than about 75 µM; NaCl of less than about 190 mM; and Thioflavin T of less than about 9.5 µM.

In various embodiments, the methods may include preparing the first incubation mixture including the first substrate protein at a concentration in µM of one or more of about: 0.001, 0.01, 0.1, 0.25, 0.5, 0.75, 1, 1.25, 1.5, 1.75, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 25, 50, 70, 100, 150, 200, 250, 500, 750, 1000, 1500, or 2000, or a range between any two of the preceding values, for example, between about 0.001 µM and about 2000 µM. The methods may include preparing the first incubation mixture characterized by heparin at a concentration in µM of one or more of about: 0.001, 0.01, 0.1, 0.25, 0.5, 0.75, 1, 1.25, 1.5, 1.75, 2, 2.5, 3, 3.5, 4, 4.5, 5, 6, 7, 8, 9, 10 11, 12, 12.5, 15, 17.5, 20, 25, 30, 35, 40, 45, 50, 55, 60, 65, 70, and 75, or a range between any two of the preceding values, for example, between about 0.001 µM and about 75 µM. The methods may include preparing the first incubation mixture including a buffer composition of one or more of: Tris-HCL, PBS, MES, PIPES, MOPS, BES, TES, and HEPES. The methods may include preparing the first incubation mixture including the buffer composition at a total concentration of one or more of about: 1 µM, 10 µM, 100 µM, 250 µM, 500 µM, 750 µM, 1 mM, 10 mM, 100 mM, 250 mM, 500 mM, 750 mM, and 1M, or a range between any two of the preceding values, for example, between about 1 µM and about 1 M. The methods may include preparing the first incubation mixture including a salt composition at a total concentration of one or more of: 1 µM, 10 µM, 100 µM, 250 µM, 500 µM, 750 µM, 1 mM, 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, 200 mM, 250 mM, 500 mM, 750 mM, and 1M, or a range between any two of the preceding values, for example, between about 1 µM and about 1 M. The salt composition may include one or more of: NaCl and KCl.

In various embodiments, the methods may include preparing or maintaining the first incubation mixture at a pH of one or more of about: 5, 5.5, 6, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, or 9, or a range between any two of the preceding values, e.g., from about pH 5 to about pH 9.

In some embodiments, the methods may include preparing the first incubation mixture including an indicator at a total concentration of one or more of: 1 nM, 10 nM, 100 nM, 250 nM, 500 nM, 750 nM, 1 µM, 2 µM, 3 µM, 4 µM, 5 µM, 6 µM, 7 µM, 8 µM, 9 µM, 9.5 µM, 10 µM, 25 µM, 50 µM, 100 µM, 250 µM, 500 µM, 750 µM, 1 mM, or a range between any two of the preceding values, for example, between about 1 nM and about 1 mM.

In some embodiments of the methods, the incubating may include heating or maintaining the first incubation mixture at a temperature in °C. of one of: 5, 10, 15, 20, 22.5, 25, 27.5, 30, 31, 32, 33, 34, 35, 36, 37, 38, 39, 40, 41, 42, 43, 44, 45, 46, 47, 50, 55, 60, or a range between any two of the preceding values, for example, between about 5° C. and about 60° C.

In several embodiments, the methods may include contacting an indicator of the first misfolded protein aggregate to the first incubation mixture. The indicator of the first misfolded protein aggregate may be characterized by an indicating state in the presence of the first misfolded protein aggregate and a non-indicating state in the absence of the first misfolded protein aggregate. Determining the presence of the first misfolded protein aggregate in the sample may include detecting the indicating state of the indicator of the first misfolded protein aggregate. The indicating state of the indicator and the non-indicating state of the indicator may be characterized by a difference in fluorescence. Determining the presence of the first misfolded protein aggregate in the sample may include detecting the difference in fluorescence. The methods may include contacting a molar excess of the indicator of the first misfolded protein aggregate to the first incubation mixture. The molar excess may be greater than a total molar amount of protein monomer included in the first substrate protein and the first misfolded protein aggregate in the first incubation mixture. The indicator of the first misfolded protein aggregate may include one or more of: a thioflavin, e.g., thioflavin T or thioflavin S; Congo Red, m-I-Stilbene, Chrysamine G, PIB, BF-227, X-34, TZDM, FDDNP, MeO-X-04, IMPY, NIAD-4, luminescent conjugated polythiophenes, a fusion with a fluorescent protein such as green fluorescent protein and yellow fluorescent protein, derivatives thereof, and the like.

In various embodiments, the method may include determining an amount of the first misfolded protein aggregate in the sample. For example, known amounts of in vitro, synthetic misfolded protein aggregate seeds may be added to various portions of a biological fluid of a healthy patient, e.g., CSF. Subsequently, PMCA may be performed on the various portions. In each of the various portions, a fluorescent indicator of the misfolded protein aggregate may be added, and fluorescence may be measured as a function of, e.g., number of PMCA cycles, to determine various PMCA kinetics parameters, e.g., number of PMCA cycles to maximum fluorescence signal, number of PMCA cycles to 50% of maximum fluorescence signal, lag phase in increase of fluorescence signal, rate of increase in fluorescence signal versus PMCA cycles, and the like. A calibration curve showing the relationship between the concentration of synthetic seeds added and the PMCA kinetic parameters. The kinetic parameters may be measured for unknown samples and compared to the calibration curve to determine the expected amount of seeds present in a particular sample. Alternatively, the amount of the first misfolded protein aggregate in the sample may be determined by a series of known dilutions of the sample, and PMCA of each serial dilution to determine whether the first misfolded protein aggregate can be detected or not in a particular dilution. The amount of the first misfolded protein aggregate in the undiluted sample can be estimated based on the known dilution that results in no detection of the first misfolded protein aggregate by PMCA. In another example, the amount of the first misfolded protein aggregate in the sample may be determined by a series of known dilutions of the sample, and PMCA to determine a detection signal in each serial dilution. The collected detection signals in the serial dilutions can be fit, e.g., via least squares analysis, to determine whether the first misfolded protein aggregate can be detected or not in a particular dilution. In another example, the amount of the first misfolded protein aggregate in the sample may be determined by known amounts of antibodies to the first misfolded protein aggregate.

In some embodiments, the methods may include detecting the amount of the first misfolded protein aggregate in the sample at a sensitivity of at least about one or more of: 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100%, e.g., at least about 70%. The methods may include detecting the amount of the first misfolded protein aggregate in the sample at less than about one or more of: 625, 62.5, 6.25, 630 μg, 63 μg, 6.3 μg, 630 ng, 63 ng, 6.3 ng, 630 pg, 200 pg, 63 pg, 6.3 pg, 630 fg, 300 fg, 200 fg, 125 fg, 63 fg, 50 fg, 30 fg, 15 fg, 12.5 fg, 10 fg, 5 fg, or 2.5 fg, The methods may include detecting the amount of the first misfolded protein aggregate in the sample at less than about one or more of: 100 nmol, 10 nmol, 1 nmol, 100 pmol, 10 pmol, 1 pmol, 100 fmol, 10 fmol, 3 fmol, 1 fmol, 100 attomol, 10 attomol, 5 attomol, 2 attomol, 1 attomol, 0.75 attomol, 0.5 attomol, 0.25 attomol, 0.2 attomol, 0.15 attomol, 0.1 attomol, and 0.05 attomol, e.g., less than about 100 nmol. The methods may include detecting the amount of the first misfolded protein aggregate in the sample in a molar ratio to the first substrate protein included by the sample. The molar ratio may be less than about one or more of: 1:100, 1:10,000, 1:100,000, and 1:1,000,000, e.g., less than about 1:100. The methods may include determining the amount of the first misfolded protein aggregate in the sample compared to a control sample.

In several embodiments, the methods may include detecting the first misfolded protein aggregate in the sample with a specificity of at least about one or more of: 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100%, e.g. at least about 70%. The methods may include detecting the first misfolded protein aggregate including one or more of: a Western Blot assay, a dot blot assay, an enzyme-linked immunosorbent assay (ELISA), a fluorescent protein/peptide binding assay, a thioflavin binding assay, a Congo Red binding assay, a sedimentation assay, electron microscopy, atomic force microscopy, surface plasmon resonance, and spectroscopy. The ELISA may include a two-sided sandwich ELISA. The spectroscopy may include one or more of: quasi-light scattering spectroscopy, multispectral ultraviolet spectroscopy, confocal dual-color fluorescence correlation spectroscopy, Fourier-transform infrared spectroscopy, capillary electrophoresis with spectroscopic detection, electron spin resonance spectroscopy, nuclear magnetic resonance spectroscopy, and Fluorescence Resonance Energy Transfer (FRET) spectroscopy. Detecting the first misfolded protein aggregate may include contacting the first incubation mixture with a protease; and detecting the first misfolded protein aggregate using anti-misfolded protein antibodies or antibodies specific for a misfolded tau aggregate in one or more of: a Western Blot assay, a dot blot assay, and an ELISA.

In various embodiments, the methods may include providing the first substrate protein in labeled form. The first substrate protein in labeled form may include one or more of: a covalently incorporated radioactive amino acid, a covalently incorporated, isotopically labeled amino acid, and a covalently incorporated fluorophore. The methods may include detecting the first substrate protein in labeled form as incorporated into the first amplified, misfolded protein aggregate.

In some embodiments, the sample may include one or more of a bio-fluid, e.g., blood, a biomaterial, e.g., cerumen, a homogenized tissue, and a cell lysate. The sample may include one or more of: amniotic fluid; bile; blood; cerebrospinal fluid; cerumen; skin; exudate; feces; gastric fluid; lymph; milk; mucus; mucosal membrane; peritoneal fluid; plasma; pleural fluid; pus; saliva; sebum; semen; sweat; synovial fluid; tears; and urine. The sample may be derived from cells or tissue of one or more of: skin, brain, heart, liver, pancreas, lung, kidney, gastro-intestine, nerve, mucous membrane, blood cell, gland, and muscle. The methods may include obtaining the sample from a subject, such as by drawing a bio-fluid or biomaterial, performing a tissue biopsy, and the like. The volume of each portion of the sample added to a particular PMCA reaction, e.g., in fluid or homogenized form, may be a volume in μL of one of about 5,000, 4,000, 3,000, 2,000, 1000, 900, 800, 750, 700, 650, 600, 550, 500, 450, 400, 350, 300, 250, 200, 150, 125, 100, 90, 80, 70, 60, 50, 40, 30, 25, 20, 15, 10, 5, or 1, or a range between any two of the preceding values, e.g., from about 1 μL to about 1000 μL. In some embodiments, when the sample is CSF, the amount of each portion added to a particular PMCA reaction may be a volume in μt of any of the preceding, for example, one of about 80, 70, 60, 50, 40, 30, 25, 20, 15, or 10, or a range between any two of the preceding values, e.g., e.g., from about 10 μL to about 80 μL, e.g., about 40 μL. In some embodiments, when the sample is plasma, the amount of each portion added to a particular PMCA reaction may be a volume in μL of any of the preceding, for example, one of about 750, 700, 650, 600, 550, 500, 450, 400, 350, 300, 250, or a range between any two of the preceding values, e.g., e.g., from about 250 μL to about 750 μL, e.g., about 500 μL. In some embodiments, when the sample is blood, the amount of each portion added to a particular PMCA reaction may be a volume in μL of any of the preceding, for example, one of about 5,000, 4,000, 3,000, 2,000, 1000, 900, 800, 750, 700, 650, 600, 550, 500, 450, 400, 350, 300, 250, or 200, or a range between any two of the preceding values, e.g., from about 200 μL to about 1000 μL.

In several embodiments, the subject may be one of a: human, mouse, rat, dog, cat, cattle, horse, deer, elk, sheep, goat, pig, and non-human primate. The subject may be one or more of: at risk of a tauopathy, having the tauopathy, and under treatment for the tauopathy. The methods may include determining a progression or homeostasis of a tauopathy in the subject by comparing the amount of the first misfolded protein aggregate in the sample to an amount of the first misfolded protein aggregate in a comparison sample taken from the subject at a different time compared to the sample. The subject may be treated with a tauopathy modulating therapy. The methods may include comparing the amount of the first misfolded protein aggregate in the sample to an amount of the first misfolded protein aggregate in a comparison sample. The sample and the comparison sample may be taken from the subject at different times over a period of time under the tauopathy modulating therapy. The methods may include determining the subject is one of: responsive to the tauopathy modulating therapy according to a change in the first misfolded protein aggregate over the period of time, or non-responsive to the tauopathy modulating therapy according to homeostasis of the first misfolded protein aggregate over the period of time. The methods may include treating the subject determined to be responsive to the tauopathy modulating therapy with the tauopathy modulating therapy. The methods may include treating the subject with a tauopathy modulating therapy to inhibit production of the first substrate protein or to inhibit aggregation of the first misfolded protein aggregate.

In some embodiments, the subject may be treated with a protein misfolding disorder (PMD) modulating therapy. The method may include comparing the amount of the each misfolded protein aggregate in the sample to an amount of the each misfolded protein aggregate in a comparison sample. The sample and the comparison sample may be taken from the subject at different times over a period of time under the each misfolded protein aggregate modulating therapy. The method may include determining or diagnosing the subject is one of: responsive to the each misfolded protein aggregate modulating therapy according to a change in the each misfolded protein aggregate over the period of time, or non-responsive to the each misfolded protein aggregate modulating therapy according to homeostasis of the each misfolded protein aggregate over the period of time. The method may include treating the subject determined to be responsive to the each misfolded protein aggregate modulating therapy with the each misfolded protein aggregate modulating therapy. For AD, for example, the PMD modulating therapy may include administration of one or more of: an inhibitor of BACE1 (beta-secretase 1); an inhibitor of γ-secretase; and a modulator of Aβ homeostasis, e.g., an immunotherapeutic modulator of Aβ homeostasis. The Aβ modulating therapy may include administration of one or more of: E2609; MK-8931; LY2886721; AZD3293; semagacestat (LY-450139); avagacestat (BMS-708163); solanezumab; crenezumab; bapineuzumab; BIIB037; CAD106; 8F5 or 5598 or other antibodies raised against Aβ globulomers, e.g., as described by Barghorn et al, "Globular amyloid β-peptide$_{1-42}$ oligomer—a homogenous and stable neuropathological protein in Alzheimer's disease" *J. Neurochem.*, 2005, 95, 834-847, the entire teachings of which are incorporated herein by reference; ACC-001; V950; Affitrope AD02; and the like.

For PD, for example, the PMD modulating therapy may include active immunization, such as PD01A+ or PD03A+, passive immunization such as PRX002, and the like. The PMD modulating therapy may also include treatment with GDNF (Glia cell-line derived neurotrophic factor), inosine, Calcium-channel blockers, specifically Cav1.3 channel blockers such as isradipine, nicotine and nicotine-receptor agonists, GM-CSF, glutathione, PPAR-gamma agonists such as pioglitazone, and dopamine receptor agonists, including D2/D3 dopamine receptor agonists and LRRK2 (leucine-rich repeat kinase 2) inhibitors.

In several embodiments, the amount of misfolded protein may be measured in samples from patients using PMCA. Patients with elevated misfolded protein measurements may be treated with disease modifying therapies for a PMD. Patients with normal misfolded protein measurements may not be treated. A response of a patient to disease-modifying therapies may be followed. For example, misfolded protein levels may be measured in a patient sample at the beginning of a therapeutic intervention. Following treatment of the patient for a clinical meaningful period of time, another patient sample may be obtained and misfolded protein levels may be measured. Patients who show a change in misfolded protein levels following therapeutic intervention may be considered to respond to the treatment. Patients who show unchanged misfolded protein levels may be considered non-responding. The methods may include detection of misfolded protein aggregates in patient samples containing components that may interfere with the PMCA reaction.

In various embodiments, the methods may include selectively concentrating the first misfolded protein aggregate in one or more of the sample and the first incubation mixture. The selectively concentrating the first misfolded protein aggregate may include pre-treating the sample prior to forming the first incubation mixture. The selectively concentrating the first misfolded protein aggregate may include pre-treating the first incubation mixture prior to incubating the first incubation mixture. The selectively concentrating the first misfolded protein aggregate may include contacting one or more antibodies capable of binding the first misfolded protein aggregate to form a captured first misfolded protein aggregate. The one or more antibodies capable of binding the first misfolded protein aggregate may include one or more of: an antibody specific for an amino acid epitope sequence of the first misfolded protein aggregate, and an antibody specific for a conformation of the first misfolded protein aggregate. The antibody specific for a conformation of the first misfolded protein aggregate may be selective for a conformational epitope of a tauopathy-specific misfolded tau aggregate. The one or more one or more antibodies capable of binding the first misfolded protein aggregate may be coupled to a solid phase. The solid phase may include one or more of a magnetic bead and a multiwell plate.

For example, ELISA plates may be coated with the antibodies used to capture first misfolded protein aggregate from the patient sample. The antibody-coated ELISA plates may be incubated with a patient sample, unbound materials may be washed off, and the PMCA reaction may be performed. Antibodies may also be coupled to beads. The beads may be incubated with the patient sample and used to separate first misfolded protein aggregate-antibody complexes from the remainder of the patient sample.

In some embodiments, contacting the sample with the first substrate protein to form the first incubation mixture may include contacting a molar excess of the first substrate protein to the sample including the captured first misfolded protein aggregate. The molar excess of the first substrate protein may be greater than a total molar amount of protein monomer included in the captured first misfolded protein aggregate. Incubating the first incubation mixture may be effective to cause misfolding and/or aggregation of the first substrate protein in the presence of the captured first misfolded protein aggregate to form the first amplified, misfolded protein aggregate.

In several embodiments, disrupting the first incubation mixture may include physically disrupting and/or thermally disrupting. For example, the disrupting may include one or more of: sonication, stirring, shaking, freezing/thawing, laser irradiation, autoclave incubation, high pressure, and homogenization. Disrupting the first incubation mixture may include cyclic agitation. The cyclic agitation may be conducted for one or more of: between about 50 rotations per minute (RPM) and 10,000 RPM, between about 200 RPM and about 2000 RPM, and at about 500 RPM. Disrupting the first incubation mixture may be conducted in each incubation cycle for one or more of: between about 5 seconds and about 10 minutes, between about 30 sec and about 1 minute, between about 45 sec and about 1 minute, and about 1 minute. Incubating the first incubation mixture may be independently conducted, in each incubation cycle for one or more of: between about 1 minute and about 5 hours, between about 5 minutes and about 5 hours, between about 10 minutes and about 2 hours, between about 15 minutes and about 1 hour, and between about 25 minutes and about 45 minutes. Each incubation cycle may include independently incubating and disrupting the first incubation mixture for one or more of: incubating between about 1 minute and about 5 hours and disrupting between about 5 seconds and about 10 minutes; incubating between about 5 minutes and about 5 hours and disrupting between about 5 seconds and about 10 minutes; incubating between about 10 minutes and about 2 hours and disrupting between about 30 sec and about 1 minute; incubating between about 15 minutes and about 1 hour and disrupting between about 45 sec and about 1 minute; incubating between about 25 minutes and about 45 minutes and disrupting between about 45 sec and about 90 seconds; incubating for about 29 minutes and for about 1 minute; and incubating about 1 minute and disrupting about 1 minute. Conducting the incubation cycle may be repeated for one or more of: between about 2 times and about 1000 times, between about 5 times and about 500 times, between about 50 times and about 500 times, and between about 150 times and about 250 times.

In various embodiments, contacting the sample with the first substrate protein to form the first incubation mixture may be conducted under physiological conditions. the methods may include contacting the sample with a molar excess of the first substrate protein to form the first incubation mixture. The molar excess may be greater than a total molar amount of protein monomer included in the first misfolded protein aggregate in the sample.

In some embodiments, the methods may include contacting the sample with a thioflavin, e.g., thioflavin T or thioflavin S, and a molar excess of the first substrate protein to form the first incubation mixture. The molar excess may be greater than an amount of the first substrate protein included in the first misfolded protein aggregate in the sample. The method may include conducting the incubation cycle two or more times effective to form the first amplified, misfolded protein aggregate. Each incubation cycle may include incubating the first incubation mixture effective to cause misfolding and/or aggregation of at least the portion of the first substrate protein in the presence of the first misfolded protein aggregate. Each incubation cycle may include shaking the first incubation mixture effective to form the first amplified, misfolded protein aggregate. The methods may include determining the presence of the first misfolded protein aggregate in the sample by detecting a fluorescence of the thioflavin corresponding to the first misfolded protein aggregate.

In several embodiments, the first substrate protein may be produced by one of: chemical synthesis, recombinant production, and extraction from non-recombinant biological samples. The first misfolded protein aggregate may include one or more of a soluble first misfolded protein aggregate and an insoluble first misfolded protein aggregate. The first amplified, misfolded protein aggregate may include one or more of: a soluble portion and an insoluble portion, The first misfolded protein aggregate may be substantially be a soluble first misfolded protein aggregate. In some embodiments, the methods may provide that the sample excludes tau fibrils. For example, the sample may be filtered or centrifuged to remove tau fibrils.

In various embodiments, the second substrate protein may be distinct from the first substrate protein. The second substrate protein may include one of: amyloid-beta (Aβ), alpha synuclein, 3R tau, and 4R tau. The first substrate protein may include 4R tau.

In some embodiments, the methods may include performing at least a second PMCA procedure to determine the presence or absence in the sample of a second misfolded protein aggregate. The second PMCA procedure may include forming a second incubation mixture by contacting a second portion of the sample with a second substrate protein. The second substrate protein may be subject to pathological misfolding and/or aggregation in vivo to form the second misfolded protein aggregate. The second PMCA procedure may include conducting an incubation cycle two or more times under conditions effective to form a second amplified, misfolded protein aggregate. Each incubation cycle may include incubating the second incubation mixture effective to cause misfolding and/or aggregation of the second substrate protein in the presence of the second misfolded protein aggregate. Each incubation cycle may include disrupting the second incubation mixture effective to form the second amplified, misfolded protein aggregate. The second PMCA procedure may include determining the presence or absence in the sample of the second misfolded protein aggregate by analyzing the second incubation mixture for the presence or absence of the second amplified, misfolded protein aggregate. The second misfolded protein aggregate may include the second substrate protein. The second amplified, misfolded protein aggregate may include the second substrate protein.

In several embodiments, the tauopathy may be present in the subject. The methods may include characterizing an identity of the tauopathy in the subject according to the presence in the sample of the first misfolded protein aggregate. The methods may include characterizing an identity of the tauopathy in the subject according to the presence or absence in the sample of the second misfolded protein aggregate.

In some embodiments, the methods may provide that that the tauopathy is not primarily characterized by misfolding and/or aggregation of 3R tau protein. For example, the tauopathy may be characterized at least in part by misfolded and/or aggregated 4R tau protein, in a ratio to misfolded and/or aggregated 3R tau protein, of one of about: 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, and 99:1, or a range between any two of the preceding ratios, for example, between 1:99 and 99:1.

In various embodiments, the methods may include contacting the sample with a thioflavin, e.g., thioflavin S or thioflavin T, and a molar excess of the first substrate protein to form the first incubation mixture. The molar excess may be greater than an amount of protein monomer included in the first misfolded protein aggregate in the sample. The methods may include conducting the incubation cycle two or more times effective to form the first amplified, misfolded protein aggregate. Each incubation cycle may include incubating the first incubation mixture effective to cause misfolding and/or aggregation of at least the portion of the first substrate protein in the presence of the first misfolded protein aggregate. Each incubation cycle may include shaking the first incubation mixture effective to form the first amplified, misfolded protein aggregate. The methods may include determining the presence or absence of the first misfolded protein aggregate in the sample by detecting a fluorescence of the thioflavin corresponding to the first misfolded protein aggregate.

In some embodiments of the methods, the capturing the first misfolded protein aggregate from the sample to form a captured first misfolded protein aggregate may be conducted using one or more antibodies specific for the first misfolded protein aggregate. The one or more antibodies specific for the first misfolded protein aggregate may include one or more of: an antibody specific for an amino acid epitope sequence of the first misfolded protein aggregate and an antibody specific for a conformation of the first misfolded protein aggregate. The antibody specific for a conformation of the first misfolded protein aggregate may be selective for a conformational epitope of a tauopathy-specific first misfolded protein aggregate. The antibody specific for the conformation of the first misfolded protein aggregate may correspond to one of: Alzheimer's disease (AD), Parkinson's Disease (PD), Progressive Supranuclear Palsy (PSP), FrontoTemporal Dementia (FTD), Corticobasal degeneration (CBD), Mild cognitive impairment (MCI), Argyrophilic grain disease (AgD) Traumatic Brain Injury (TBI), Chronic Traumatic Encephalopathy (CTE), and Dementia Pugilistica (DP). The one or more antibodies specific for the first misfolded protein aggregate may be coupled to a solid phase. The solid phase may include one or more of a magnetic bead and a multiwell plate. Contacting the sample with the first substrate protein to form the first incubation mixture may include contacting a molar excess of the first substrate protein to the sample. The molar excess of the first substrate protein may be greater than a total molar amount of protein monomer included in the captured first misfolded protein aggregate. Incubating the first incubation mixture may be effective to cause misfolding and/or aggregation of the first substrate protein in the presence of the captured first misfolded protein aggregate to form the first amplified, misfolded protein aggregate. The first substrate protein may include 4R tau protein.

In various embodiments, the methods may include performing at least a second PMCA procedure to determine the presence or absence in the sample of a second misfolded protein aggregate. The second PMCA procedure may include forming a second incubation mixture by contacting a second portion of the sample with a second substrate protein, the second substrate protein may be subject to pathological misfolding and/or aggregation. The second PMCA procedure may include conducting an incubation cycle two or more times under conditions effective to form a second amplified, misfolded protein aggregate. Each incubation cycle may include incubating the second incubation mixture effective to cause misfolding and/or aggregation of the second substrate protein in the presence of the second misfolded protein aggregate. Each incubation cycle may include disrupting the second incubation mixture effective to form the second amplified, misfolded protein aggregate The second PMCA procedure may include determining the presence or absence in the sample of the second misfolded protein aggregate by analyzing the second incubation mixture for the presence or absence of the second amplified, misfolded protein aggregate. The tauopathy may be present in the subject. The methods may include characterizing an identity of the tauopathy in the subject according to: the presence in the sample of the first misfolded protein aggregate; and the presence or absence in the sample of the second misfolded protein aggregate. The second misfolded protein aggregate may include the second substrate protein. The second amplified, misfolded protein aggregate may include the second substrate protein. The second substrate protein may be distinct from the first substrate protein. The second substrate protein may include one of: amyloid-beta (Aβ), alpha synuclein, and 3R tau.

In some embodiments, the methods may include distinguishing each tauopathy from one or more additional tauopathies by analyzing for at least one signature of one or more misfolded aggregates each corresponding to one of Aβ, alpha synuclein, and 3R tau. Each signature may correspond to one or more of: an assay using an antibody selective for a conformational epitope of any of the one or more misfolded aggregates; an assay using an antibody selective for a conformational epitope of any of the one or more misfolded aggregates; one or more PMCA kinetic parameters of the one or more misfolded aggregates, including one or more of: lag phase, $T_{50}$, amplification rate, and amplification extent; an indicator selective for any of the one or more misfolded aggregates; and a spectrum characteristic of any of the one or more misfolded aggregates.

Further, for example, specific antibodies may be employed for second misfolded protein aggregates. For example, for AD, amyloid antibodies may include one or more of: 6E10, 4G8, 82E1, A11, X-40/42, 16ADV; and the like. Such antibodies may be obtained as follows: 6E10 and 4G8 (Covance, Princeton, N.J.); 82E1 (IBL America, Minneapolis, Minn.); A11 (Invitrogen, Carlsbad, Calif.); X-40/42 (MyBioSource, Inc., San Diego, Calif.); and 16ADV (Acumen Pharmaceuticals, Livermore, Calif.).

Further, for PD, for example, the one or more synuclein specific antibodies may include PD specific antibodies including one or more of: α/β-synuclein N-19; α-synuclein C-20-R; α-synuclein 211; α-synuclein Syn 204; α-synuclein 2B2D1; α-synuclein LB 509; α-synuclein SPM451; α-synuclein 3G282; α-synuclein 3H2897; α/β-synuclein Syn 202; α/β-synuclein 3B6; α/β/γ-synuclein FL-140; and the like. In some examples, the one or more specific antibodies may include one or more of: α/β-synuclein N-19; α-synuclein C-20-R; α-synuclein 211; α-synuclein Syn 204; and the like. Such antibodies may be obtained as follows: α/β-synuclein N-19 (cat. No. SC-7012, Santa Cruz Biotech, Dallas, Tex.); α-synuclein C-20-R (SC-7011-R); α-synuclein 211 (SC-12767); α-synuclein Syn 204 (SC-32280); α-synuclein 2B2D1 (SC-53955); α-synuclein LB 509 (SC-58480); α-synuclein SPM451 (SC-52979); α-synuclein 3G282 (SC-69978); α-synuclein 3H2897 (SC-69977); α/β-synuclein Syn 202 (SC-32281); α/β-synuclein 3B6 (SC-69699); or α/0/γ-synuclein FL-140 (SC-10717).

In various embodiments, a kit is provided for determining a presence or absence in a sample of a first misfolded protein aggregate. The kit may include a first substrate protein that may include 4R tau. The kit may include an indicator of the first misfolded protein aggregate. The first misfolded protein aggregate may include the first substrate protein. The first misfolded protein aggregate may correspond to a tauopathy. The kit may include a buffer. The kit may include heparin. The kit may include a salt. The kit may include instructions. The instructions may direct a user to obtain the sample. The instructions may direct the user to perform at least a first PMCA procedure. The first PMCA procedure may include forming a first incubation mixture by contacting a first portion of the sample with the first substrate protein, the indicator of the first misfolded protein aggregate, the buffer, the heparin, and the salt. The first incubation mixture may be formed with a concentration of one or more of: the first substrate protein of less than about 20 μM; the heparin of less than about 75 µM; the salt as NaCl of less than about 190 mM; and the indicator of the first misfolded protein aggregate as Thioflavin T of less than about 9.5 µM. The first PMCA procedure may include conducting an incubation cycle two or more times effective to form a first amplified, misfolded protein aggregate. Each incubation cycle may include incubating the first incubation mixture effective to cause misfolding and/or aggregation of the first substrate protein in the presence of the first misfolded protein aggregate. Each incubation cycle may include disrupting the incubation mixture effective to form the first amplified, misfolded protein aggregate. The instructions may direct the user to determine the presence or absence in the sample of the first misfolded protein aggregate by analyzing the first incubation mixture for the presence or absence of the first amplified, misfolded protein aggregate according to the indicator of the first misfolded protein aggregate.

In several embodiments, the kit may include any element of the methods described herein. Moreover, the kit may include instructions directing the user to conduct any of the steps of the methods described herein.

In some embodiments, for example, the instructions may include directing the user to obtain the sample from a subject. The sample may include one or more of: a bio-fluid, a biomaterial, a homogenized tissue, and a cell lysate. The instructions directing the user to determine or diagnose a tauopathy in the subject according to the presence or absence in the sample of the first misfolded protein aggregate.

In various embodiments, the kit may include a second substrate protein and an indicator of a second misfolded protein aggregate. The second misfolded protein aggregate may include the second substrate protein. The second substrate protein may be distinct from the first substrate protein. The second substrate protein may include one of: amyloid-beta (Aβ), alpha synuclein, 3R tau, and 4R tau. The instructions may direct the user to perform at least a second PMCA procedure. The second PMCA procedure may include forming a second incubation mixture by contacting a second portion of the sample with the second substrate protein and the indicator of the second misfolded protein aggregate. The second PMCA procedure may include conducting an incubation cycle two or more times effective to form a second amplified, misfolded protein aggregate. Each incubation cycle may include incubating the second incubation mixture effective to cause misfolding and/or aggregation of the second substrate protein in the presence of the second misfolded protein aggregate. Each incubation cycle may include disrupting the incubation mixture effective to form the second amplified, misfolded protein aggregate. The second PMCA procedure may include determining the presence or absence in the sample of the second misfolded protein aggregate by analyzing the second incubation mixture for the presence or absence of the second amplified, misfolded protein aggregate. The instructions may also direct the user to characterize the sample for an identity of a tauopathy according to: the presence in the sample of the first misfolded protein aggregate; and the presence or absence in the sample of the second misfolded protein aggregate.

In some embodiments, the kit may include a PMCA apparatus. The PMCA apparatus may include one or more of: a multiwall microtitre plate; a microfluidic plate; a shaking apparatus; a spectrometer; and an incubator. The apparatus may be included either as one or more of the individual plates or apparatuses, as a combination device, and the like. For example, a shaking microplate reader may be used to perform cycles of incubation and shaking and automatically measure the ThT fluorescence emission during the course of an experiment (e.g., FLUOstar OPTIMA, BMG LABTECH Inc., Cary, N.C.).

The antibody specific for the conformation of the first misfolded protein aggregate may correspond to one of: Alzheimer's disease (AD), Parkinson's Disease (PD), Progressive Supranuclear Palsy (PSP), FrontoTemporal Dementia (FTD), Corticobasal degeneration (CBD), Mild cognitive impairment (MCI), Argyrophilic grain disease (AgD) Traumatic Brain Injury (TBI), Chronic Traumatic Encephalopathy (CTE), and Dementia Pugilistica (DP). The instructions may include determining, according to a binding assay using the antibody specific for the conformation of the first misfolded protein aggregate, the presence or absence in the subject of one of AD, PD, PSP, FTD, CBD, MCI, AgD, TBI, CTE, and DP.

EXAMPLES

Example 1: Preparation of Synthetic Aβ Oligomers

Aβ1-42 was synthesized using solid-phase N-tert-butyloxycarbonyl chemistry at the W. Keck Facility at Yale University and purified by reverse-phase HPLC. The final product was lyophilized and characterized by amino acid analysis and mass spectrometry. To prepare stock solutions free of aggregated, misfolded Aβ protein, aggregates were dissolved high pH and filtration through 30 kDa cut-off filters to remove remaining aggregates. To prepare different types of aggregates, solutions of seed-free Aβ1-42 (10 µM) were incubated for different times at 25° C. in 0.1 M Tris-HCl, pH 7.4 with agitation. This preparation contained a mixture of Aβ monomers as well as fibrils, protofibrils and soluble, misfolded Aβ protein in distinct proportions depending on the incubation time. The degree of aggregation was characterized by ThT fluorescence emission, electron microscopy after negative staining, dot blot studies with the A11 conformational antibody and western blot after gel electrophoresis using the 4G8 anti-Aβ antibody.

A mixture of Aβ oligomers of different sizes were generated during the process of fibril formation. Specifically, soluble, misfolded Aβ protein was prepared by incubation of monomeric synthetic Aβ1-42 (10 µM) at 25° C. with stirring. After 5 h of incubation, an abundance of soluble, misfolded Aβ protein, globular in appearance, was observed by electron microscopy after negative staining, with only a small amount of protofibrils and fibrils observed. At 10 h there are mostly protofibrils and at 24 h, a large amount of long fibrils are observed. FIG. 1A shows electron micrographs taken at 1 h, 5 h, 10 h, and 24 h of incubation.

Figures 1B, 7A:
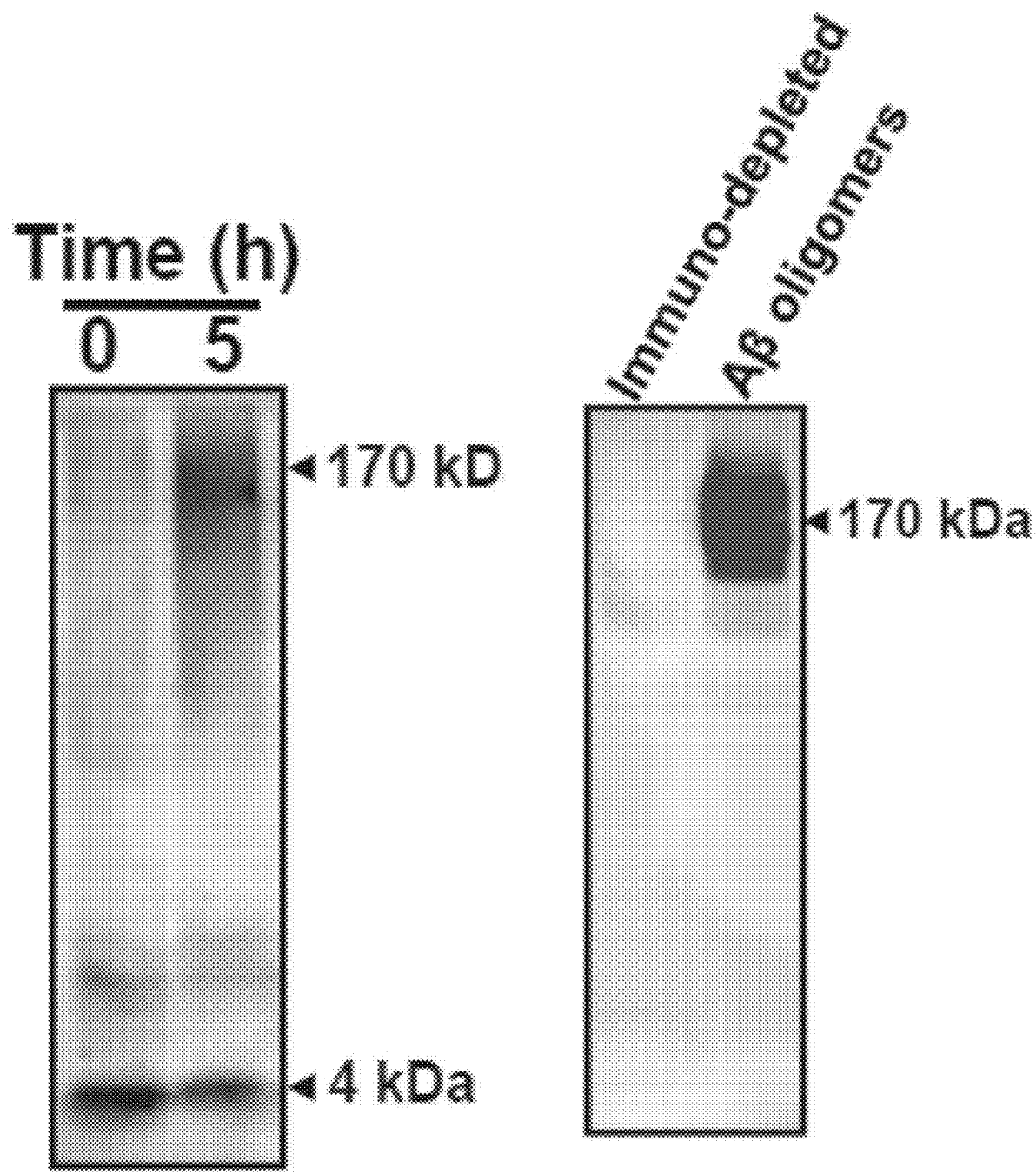
FIG. 1B is a western blot of soluble oligomeric Aβ protein aggregates.
FIG. 7A is a western blot showing results of immunodepletion using synthetically prepared Aβ oligomers spiked into human CSF.

The soluble, misfolded Aβ protein aggregates tested positive using A11 anti-oligomer specific antibody according to the method of Kayed, et al. "Common structure of soluble amyloid oligomers implies common mechanism of pathogenesis," Science 2003, 300, 486-489. After further incubation at 10 h and 24 h, protofibrillar and fibrillar structures were observed. The size of the aggregates was determined by filtration through filters of defined pore size and western blotting after SDS-PAGE separation. Soluble, misfolded Aβ protein formed by incubation for 5 h was retained in filters of 30 kDa cut-off and passed through 1000 kDa cutoff filters. FIG. 1B is a western blot of soluble, misfolded Aβ protein aggregates. Electrophoretic separation of this soluble, misfolded Aβ protein showed that the majority of the material migrated as ~170 kDa SDS-resistant aggregates, with a minor band at 17 kDa.

Example 2: Aβ-PMCA Detects Synthetic Aβ Oligomers

Figure 2A:
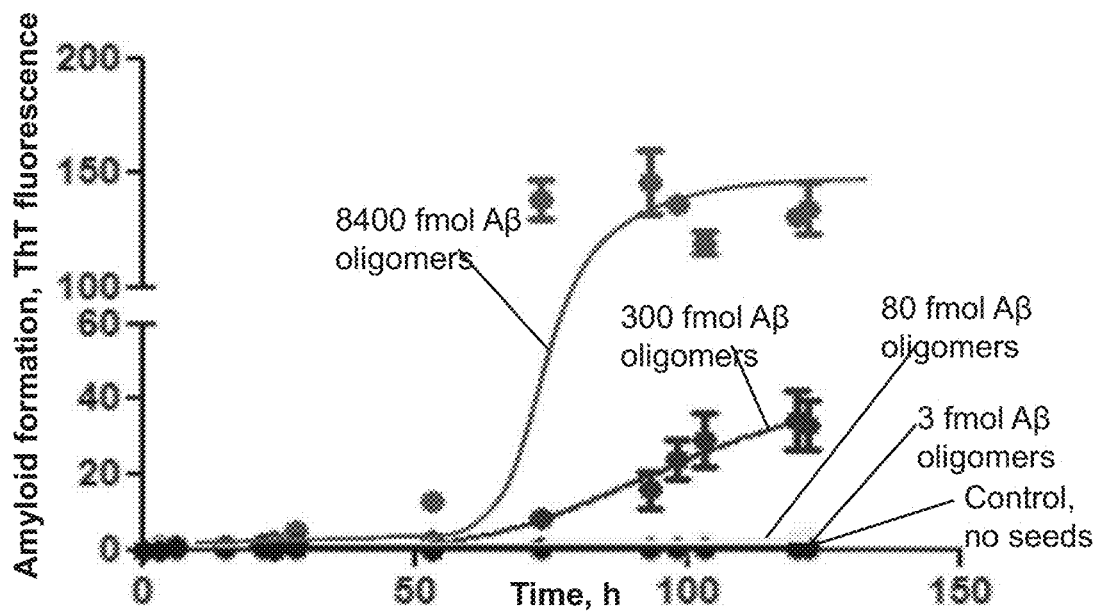
FIG. 2A is a graph showing non-amplified amyloid formation measured by ThT fluorescence as a function of time seeded by various concentrations of synthetic soluble oligomeric Aβ protein of EXAMPLE 1.

EXAMPLE 2A. Seeding of Aβ aggregation was studied by incubating a solution of seed-free Aβ1-42 in the presence of Thioflavin T with or without different quantities of synthetic soluble, misfolded Aβ protein (Control (no oligomer); or 3, 80, 300, and 8400 femtomolar in synthetic soluble, misfolded Aβ protein). Aβ-PMCA general procedure: Solutions of 2 µM aggregate-free Aβ1-42 in 0.1 M Tris-HCl pH 7.4 (200 µL total volume) were placed in opaque 96-wells plates and incubated alone or in the presence of synthetic Aβ aggregates (prepared by incubation over 5 h as described in EXAMPLE 1) or 40 µL of CSF aliquots. Samples were incubated in the presence of 5 µM Thioflavin T (ThT) and subjected to cyclic agitation (1 min at 500 rpm followed by 29 min without shaking) using an Eppendorf thermomixer, at a constant temperature of 22° C. At various time points, ThT fluorescence was measured in the plates at 485 nm after excitation at 435 nm using a plate spectrofluorometer. FIG. 2A is a graph of amyloid formation (without cyclic amplification) versus time as measured by Thioflavin T fluorescence, using the indicated femtomolar concentration of synthetic soluble, misfolded Aβ protein seeds. The peptide concentration, temperature and pH of the buffer were monitored to control the extent of the lag phase and reproducibility among experiments. Under these conditions, no spontaneous Aβ aggregation was detected during the time in which the experiment was performed (125 h). Aggregation of monomeric Aβ1-42 protein was observed in the presence of 0.3 to 8.4 fmol of the synthetic soluble, misfolded Aβ protein of EXAMPLE 1.

Figure 2B:
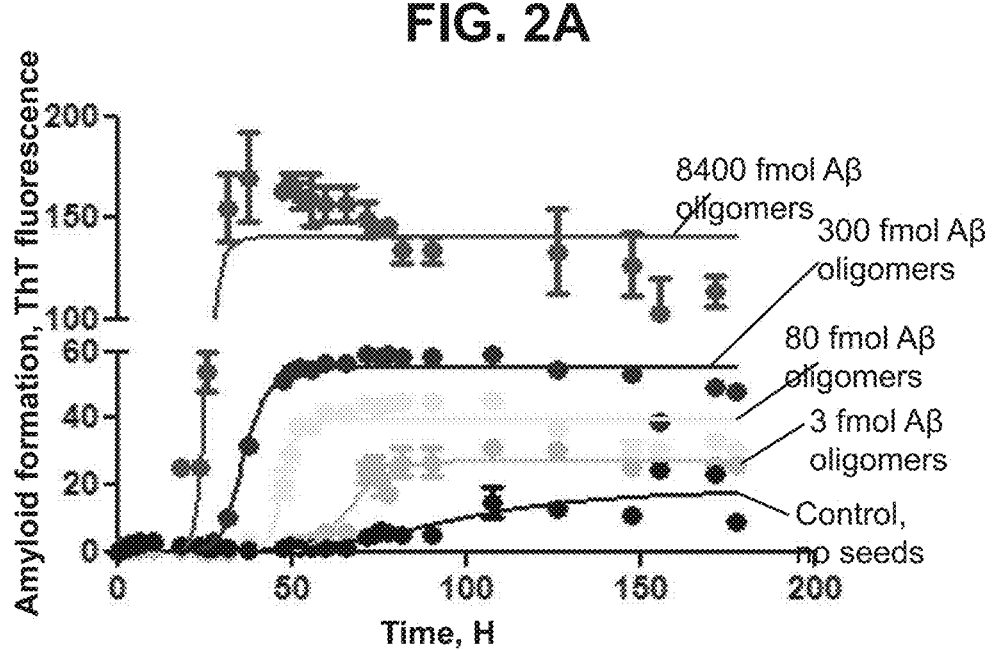
FIG. 2B is a graph showing amplification cycle-accelerated amyloid formation measured by ThT fluorescence as a function of time seeded by various concentrations of synthetic soluble oligomeric Aβ protein of EXAMPLE 1.

EXAMPLE 2B: Amplification cycles, combining phases of incubation and physical disruption were employed. The same samples as in FIG. 2A were incubated with cyclic agitation (1 min stirring at 500 rpm followed by 29 min without shaking). Aggregation was measured over time by the thioflavin T (ThT) binding to amyloid fibrils using a plate spectrofluorometer (excitation: 435; emission: 485 nm). Graphs show the mean and standard error of 3 replicates. The concentration of Aβ oligomers was estimated assuming an average molecular weight of 170 kDa. FIG. 2B is a graph showing amplification cycle-accelerated amyloid formation measured by ThT fluorescence as a function of time for various concentrations of the synthetic soluble, misfolded Aβ protein of EXAMPLE 1. Under these conditions, the aggregation of monomeric Aβ1-42 protein induced by 8400, 300, 80 and 3 fmol of the synthetic soluble, misfolded Aβ protein was clearly faster and more easily distinguished from that observed in the absence of the synthetic soluble, misfolded Aβ protein. This result indicates the detection limit, under these conditions, is 3 fmol of soluble, misfolded Aβ protein or less in a given sample.

Example 3: Aβ-PMCA Detects Misfolded Aβ in the Cerebrospinal Fluid of AD Patients Aliquots of CSF were obtained from 50 AD patients, 39 cognitively normal individuals affected by non-degenerative neurological diseases (NND), and 37 patients affected by non-AD neurodegenerative diseases including other forms of dementia (NAND). Test CSF samples were obtained from 50 patients with the diagnosis of probable AD as defined by the DSM-IV and the NINCDS-ADRA guidelines (McKhann et al., 1984) and determined using a variety of tests, including routine medical examination, neurological evaluation, neuropsychological assessment, magnetic resonance imaging and measurements of CSF levels of Aβ1-42, total Tau and phospho-Tau. The mean age of AD patients at the time of sample collection was 71.0±8.1 years (range 49-84). Control CSF samples were obtained from 39 patients affected by non-degenerative neurological diseases (NND), including 12 cases of normal pressure hydrocephalus, 7 patients with peripheral neuropathy, 7 with diverse forms of brain tumor, 2 with ICTUS, 1 with severe cephalgia, 3 with encephalitis, 1 with hypertension and 6 with unclear diagnosis. The mean age at which CSF samples were taken from this group of patients was 64.6±14.7 years (range 31-83). Control CSF samples were also taken from 37 individuals affected by non-AD neurodegenerative diseases (NAND), including 10 cases of fronto-temporal dementia (5 behavioral and 5 language variants), 6 patients with Parkinson's disease (including 4 associated with dementia and 1 with motor neuron disease), 6 with progressive supranuclear palsy, 6 with spinocerebellar ataxia (1 associated with dementia), 4 with amyotrophic lateral sclerosis, 2 with Huntington's disease, 1 with MELAS, 1 with Lewy body dementia, and 1 with vascular dementia. The mean age at sample collection for this group was 63.8±11.1 years (range 41-80). CSF samples were collected in polypropylene tubes following lumbar puncture at the L4/L5 or L3/L4 interspace with atraumatic needles after one night fasting. The samples were centrifuged at 3,000 g for 3 min at 4° C., aliquoted and stored at –80° C. until analysis. CSF cell counts, glucose and protein concentration were determined. Albumin was measured by rate nephelometry. To evaluate the integrity of the blood brain barrier and the intrathecal IgG production, the albumin quotient (CSF albumin/serum albumin)×$10^3$ and the IgG index (CSF albumin/serum albumin)/(CSF IgG/serum IgG) were calculated. The study was conducted according to the provisions of the Helsinki Declaration and was approved by the Ethics Committee.

Figure 3A:
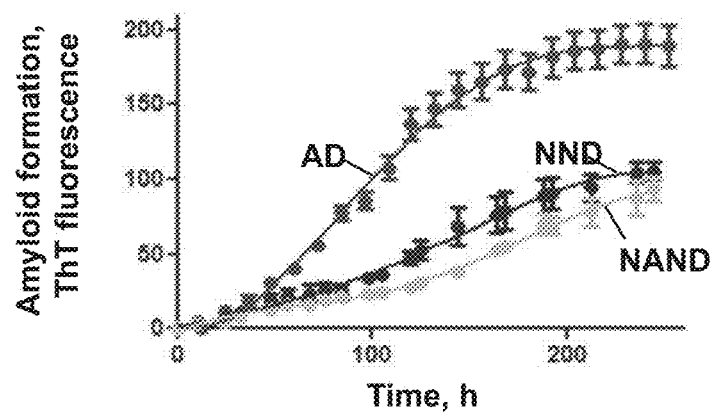
FIG. 3A is a graph of amyloid formation versus time, measured as a function of ThT fluorescence labeling, showing the average kinetics of Aβ aggregation seeded by CSF from 5 representative samples from the AD, NND, and NAND groups.

The experiments as well as the initial part of the analysis were conducted blind. FIG. 3A is a graph of amyloid formation versus time, measured as a function of ThT fluorescence labeling, showing the average kinetics of Aβ aggregation of 5 representative samples from the AD, NND, and NAND groups.

The results indicate that CSF from AD patients significantly accelerates Aβ aggregation as compared to control CSF ($P<0.001$). The significance of the differences in Aβ aggregation kinetics in the presence of human CSF samples was analyzed by one-way ANOVA, followed by the Tukey's multiple comparison post-test. The level of significance was set at $P<0.05$. The differences between AD and samples from the other two groups were highly significant with $P<0.001$ (***).

Figure 3B:
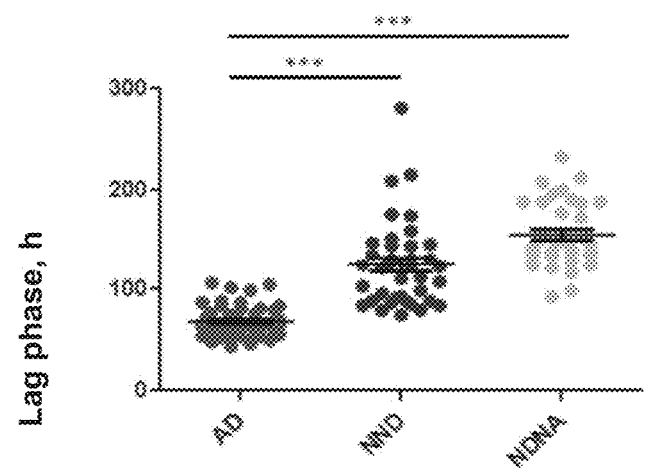
FIG. 3B is a graph of the lag phase time in h for Aβ aggregation in the presence of samples from the AD, NND, and NAND groups.

FIG. 3B is a graph of the lag phase time in h for samples from the AD, NND, and NAND groups. To determine the effect of individual samples on Aβ aggregation, the lag phase was estimated, defined as the time to ThT fluorescence larger than 40 arbitrary units after subtraction of a control buffer sample. This value was selected considering that it corresponds to ~5 times the reading of the control buffer sample.

Figure 3C:
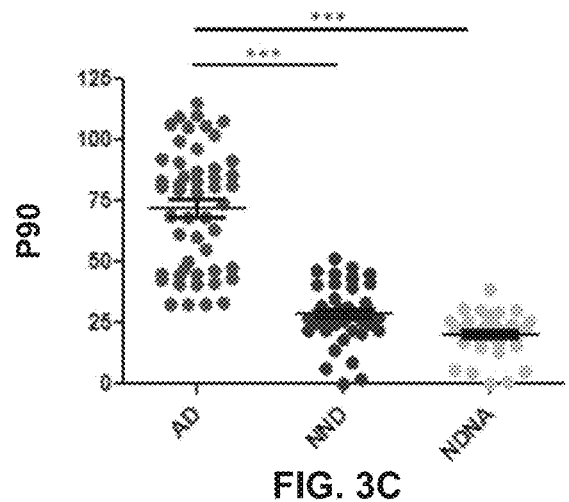
FIG. 3C is a graph showing the extent of amyloid formation obtained after 180 Aβ-PMCA cycles, i.e. 90 h of incubation (P90) in the presence of CSF samples from AD, NND and NAND patients.

FIG. 3C is a graph showing the extent of amyloid formation obtained after 180 Aβ-PMCA cycles, i.e. 90 h of incubation (P90). Comparison of the lag phase and P90 among the experimental groups reveals a significant difference between AD and control samples from individuals with non-degenerative neurological diseases or with non-AD neurodegenerative diseases. Further, no correlation was detected between the aggregation parameters and the age of the AD patients, which indicates that the levels of the marker corresponds to aggregated Aβ protein in patient CSF, and not patient age.

FIG. 5, Table 1 shows estimations of the sensitivity, specificity and predictive value of the Aβ-PMCA test, calculated using the lag phase numbers.

Figure 6:
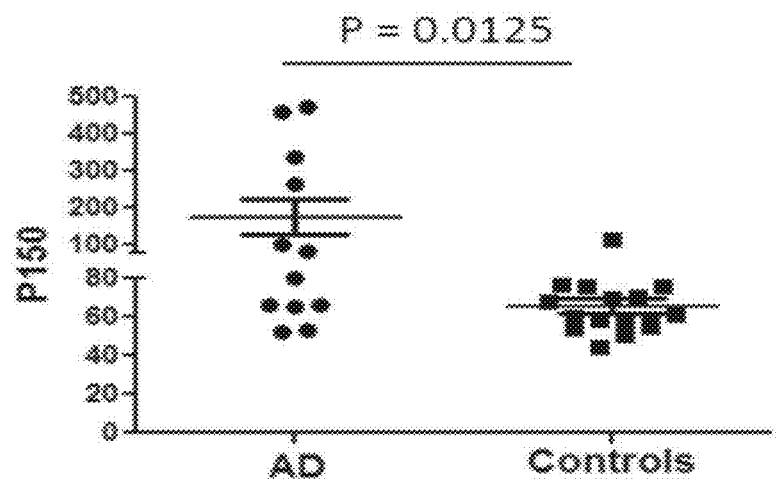
FIG. 6 is a graph of the lag phase time in h for samples obtained after 300 Aβ-PMCA cycles, i.e. 150 h of incubation (P90) in the presence of CSF samples from AD and control patients.

To study reproducibility, an experiment similar to the one shown in FIGS. 3A-C was independently done with different samples, reagents and a new batch of Aβ peptide as substrate for Aβ-PMCA. The extent of amyloid formation obtained after 300 Aβ-PMCA cycles, i.e. 150 h of incubation (P150), was measured in each patient. The control group includes both people affected by other neurodegenerative diseases and non-neurologically sick patients. Data for each sample represent the average of duplicate tubes. Statistical differences were analyzed by student-t test. FIG. 6 is a graph of the lag phase time in h for samples obtained after 300 Aβ-PMCA cycles, i.e. 150 h of incubation (P90).

During the course of the study an entire set of CSF samples coming from a fourth location did not aggregate at all, even after spiking with large concentrations of synthetic oligomers. It is expected that reagent contamination during sample collection interfered with the assay.

The differences in aggregation kinetics between different samples were evaluated by the estimation of various different kinetic parameters, including the lag phase, A50, and P90. Lag phase is defined as the time required to reach a ThT fluorescence higher than 5 times the background value of the buffer alone. The A50 corresponds to the time to reach 50% of maximum aggregation. P90 corresponds to the extent of aggregation (measured as ThT fluorescence) at 90 h. Sensitivity, specificity and predictive value were determined using this data, with cutoff thresholds determined by Receiver Operating Characteristics (ROC) curve analysis, using MedCalc software (MedCalc Software, Ostend, Belgium).

Example 4: Determination of Threshold Values of Misfolded for Aβ-PMCA Detection of AD in CSF In support of FIG. 5, TABLE 1, sensitivity, specificity and predictive value were determined using the lag phase data, with cutoff thresholds determined by Receiver Operating Characteristics (ROC) curve analysis, using the MedCalc software (version 12.2.1.0, MedCalc, Belgium). As shown in FIG. 5, TABLE 1, a 90.0% sensitivity and 84.2% specificity was estimated for the control group consisting of age-matched individuals with non-degenerative neurological diseases. By contrast, for the clinically more relevant differentiation of AD from other neurodegenerative diseases including other forms of dementia, 100% sensitivity and 94.6% specificity was estimated. This ability of Aβ-PMCA to distinguish AD from other forms of neurodegenerative diseases is clinically significant. The overall sensitivity and specificity considering all control individuals was 90% and 92%, respectively.

To evaluate the performance of the Aβ-PMCA test to distinguish AD patients from controls, the true positive rate (sensitivity) was plotted as a function of the false positive rate (specificity) for different cut-off points. For this analysis the lag phase values for AD vs NAND (FIG. 4A), AD vs NND (FIG. 4B) and AD vs All control samples (FIG. 4C) was used. The performance of the test, estimated as the area under the curve was 0.996±0.0033, 0.95±0.020 and 0.97±0.011 for the comparison of AD with NAND, NND and all controls, respectively. Statistical analysis was done using the MedCalc ROC curve analysis software (version 12.2.1.0) and the result indicated that the test can distinguish AD from the controls with a P<0.0001. To estimate the most reliable cut-off point for the different set of group comparisons, sensitivity (blue line) and specificity (red line) were plotted for each cut-off value (FIG. 4D). The graph shows the curve and the 95% confidence intervals for the AD vs all control samples (including NAND and NND groups). These cut-off values were used to estimate sensitivity, specificity and predictive value in FIG. 5, Table 1.

Example 5: Aβ-Oligomer Immunodepletion Removes Aβ Seeds in Human Cerebrospinal Fluid and Confirms Aβ-PMCA Detects Soluble Misfolded Aβ Protein in AD CSF Immunodepletion experiments were performed to confirm that Aβ-PMCA detects a seeding activity associated to soluble, misfolded Aβ protein present in CSF. The methodology for efficient immunodepletion of soluble, misfolded Aβ protein was first optimized by using synthetically prepared soluble, misfolded Aβ protein. Immunodepletion was performed by incubation with dynabeads conjugated with a mixture of antibodies recognizing specifically the sequence of Aβ (4G8) and conformational (A11) antibodies. FIG. 7A is a western blot showing results of immunodepletion using synthetically prepared Aβ oligomers spiked into human CSF. Soluble, misfolded Aβ protein was efficiently removed by this immunodepletion.

Figure 7B:
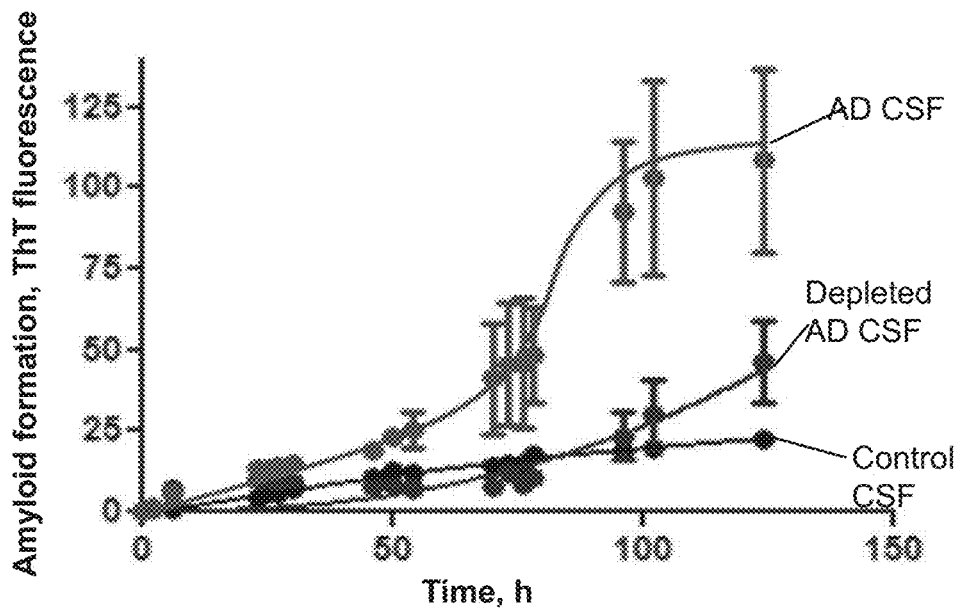
FIG. 7B is a graph showing the kinetics of Aβ aggregation seeded by control and immunodepleted CSF samples.
Figure 7C:
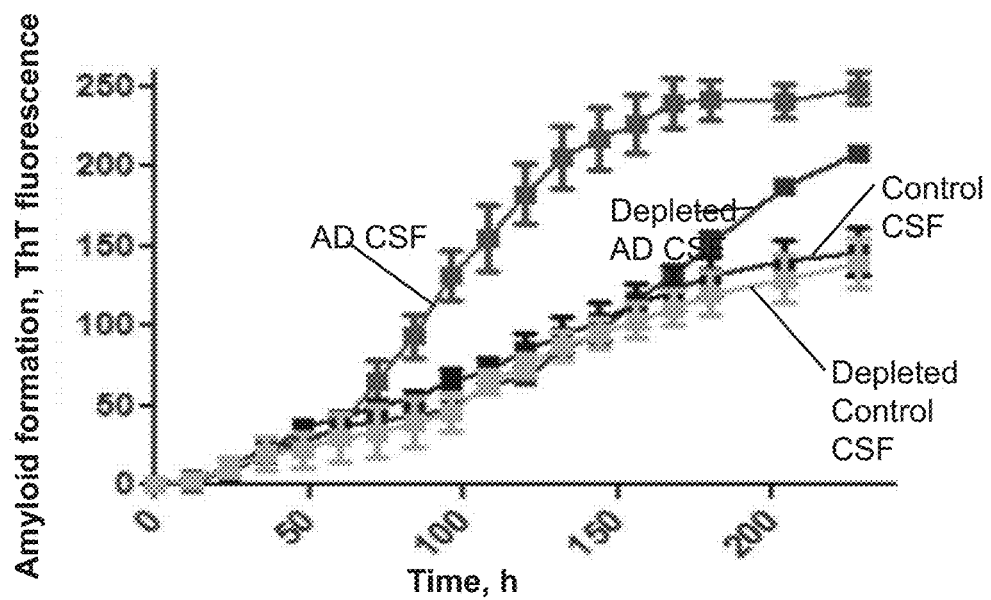
FIG. 7C is a graph showing the kinetics of Aβ aggregation seeded by control and immunodepleted CSF samples, depleted only with the A11 conformational antibody.

FIGS. 7A and 7B are graphs of amyloid formation versus time as measured by Thioflavin T fluorescence, demonstrating that seeding activity in AD CSF is removed by soluble, misfolded Aβ protein immuno-depletion. Samples of AD CSF before or after immunodepletion with 4G8 and A11 antibodies were used to seed Aβ aggregation in the Aβ-PMCA assay. Immunodepletion was applied to 3 AD CSF. FIG. 7B is a graph showing the kinetics of control and immunodepleted CSF samples. FIG. 7B shows that for immunodepleted AD CSF, the kinetics of Aβ aggregation in the Aβ-PMCA reaction was comparable to that observed in control CSF samples, and both were significantly different from the aggregation observed with AD CSF prior to immunodepletion. FIG. 7C is a graph showing the kinetics of control and immunodepleted CSF samples, depleted only with the A11 conformational antibody and aggregation monitored by Aβ-PMCA assay. FIG. 7C shows similar results, obtained using AD CSF immunodepleted using the A11 conformational antibody, which specifically recognizes, misfolded AO. These results confirm that Aβ-PMCA detects soluble, misfolded protein in AD CSF.

Example 6: Solid Phase Immuno Capturing

FIGS. 8A and 8B are schematic representations of two solid phase methods used to capture soluble, misfolded Aβ protein from complex samples such as blood plasma. Strategy 1 employed ELISA plates pre-coated with specific antibodies bound to a solid phase on the ELISA plate. After washing the plates, the Aβ-PMCA reaction was carried out in the same plates. Strategy 2 used magnetic beads as the solid phase coated with specific antibodies. This approach provided concentration of the samples.

Example 7: Specificity of Immuno Capturing

Figure 9:
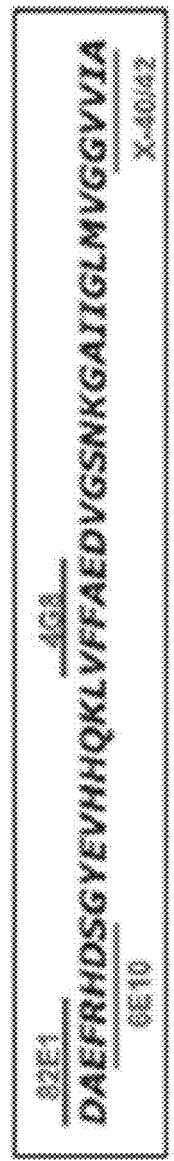
FIG. 9, Table 2 shows the ability of specific antibodies to capture the Aβ oligomers.

FIG. 9 shows Table 2, demonstrating the ability of specific antibodies to capture the Aβ oligomers. The top panel shows a schematic representation of the epitope recognition site on the Aβ protein of the diverse sequence antibodies used in this study. Table 2 in FIG. 9 demonstrates the efficiency of different sequence or conformational antibodies to capture Aβ oligomers. The capacity to capture oligomers was measured by spiking synthetic Aβ oligomers in healthy human blood plasma and detection by Aβ-PMCA. The symbols indicate that the detection limits using the different antibodies were: <12 fmol (+++); between 10-100 fmol (++); >1 pmol (+) and not significantly higher than without capturing reagent (−).

Example 8: Detection of Aβ Oligomers Spiked in Human Plasma

Figure 10:
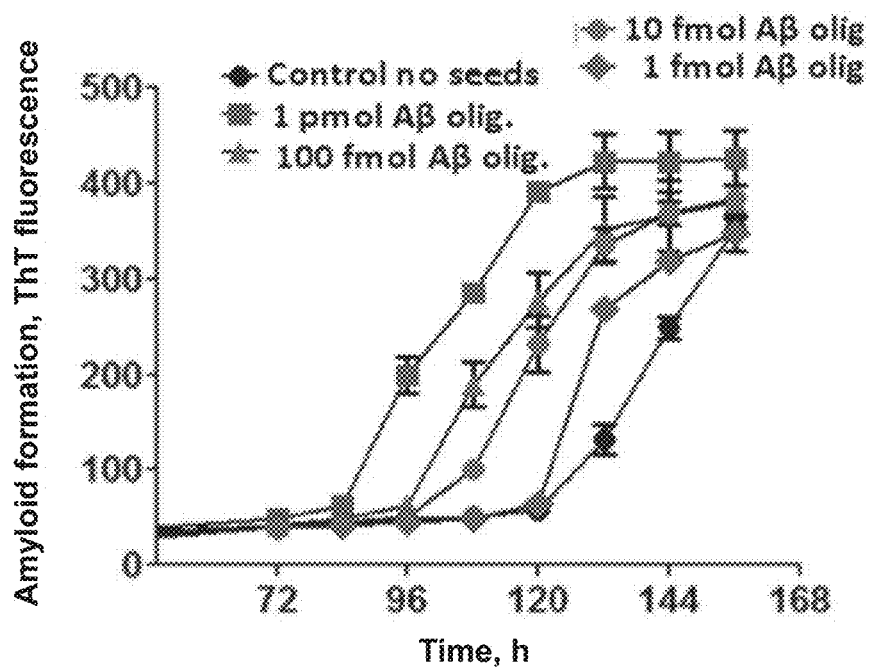
FIG. 10 is a graph of amyloid formation versus time showing the acceleration of Aβ aggregation by the presence of different quantities of synthetic oligomers spiked in human plasma.

FIG. 10 is a graph of amyloid formation versus time as measured by Thioflavin T fluorescence showing detection of soluble, misfolded Aβ protein spiked in human plasma. ELISA plates pre-coated with protein G were coated with an anti-conformational antibody (16ADV from Acumen). Thereafter, plates were incubated with human blood plasma (100 μl) as such (control) or spiked with different concentrations of synthetic soluble, misfolded Aβ protein. After incubation, plates were subjected to Aβ-PMCA (29 min incubation and 30 s shaking) in the presence of Aβ40 monomer (2 μM) and ThT (5 μM). Amyloid formation was measured by Thioflavin fluorescence. FIG. 10 is representative of several experiments done with 3 different antibodies which worked similarly.

Figure 11:
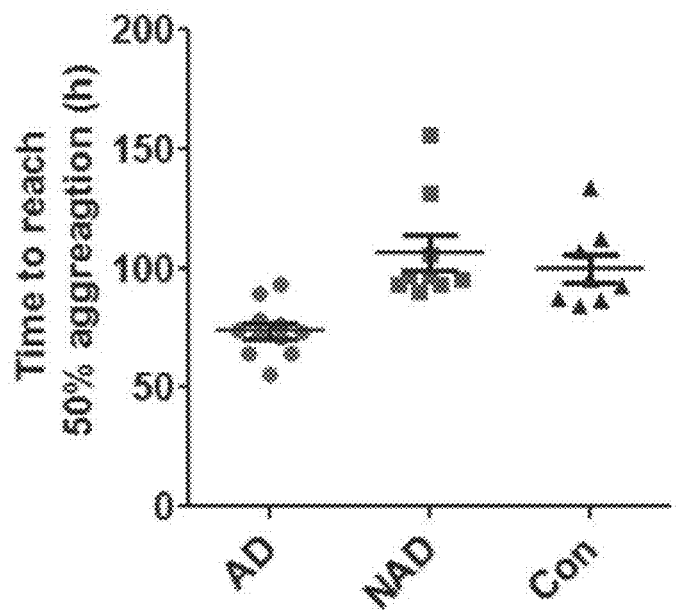
FIG. 11 is a graph showing time to reach 50% aggregation in an Aβ-PMCA assay in the presence of plasma samples from AD patients and controls.

Example 9: Capturing of Soluble Misfolded Aβ from AD Patient Samples Vs Controls FIG. 11 is a graph showing time to reach 50% aggregation in an Aβ-PMCA assay in plasma samples from AD patients and controls. Blood plasma samples from patients affected by AD, non-AD neurodegenerative diseases (NAD), and healthy controls were incubated with anti-Aβ antibody (82E1) coated beads. Aβ-PMCA was carried out as described in EXAMPLE 2. The time needed to reach 50% aggregation was recorded in individual patients in each group. Differences were analyzed by one-way ANOVA followed by the Tukey's post-hoc test. ROC analysis of this data showed a 82% sensitivity and 100% specificity for correctly identifying AD patients from controls.

Figure 12:
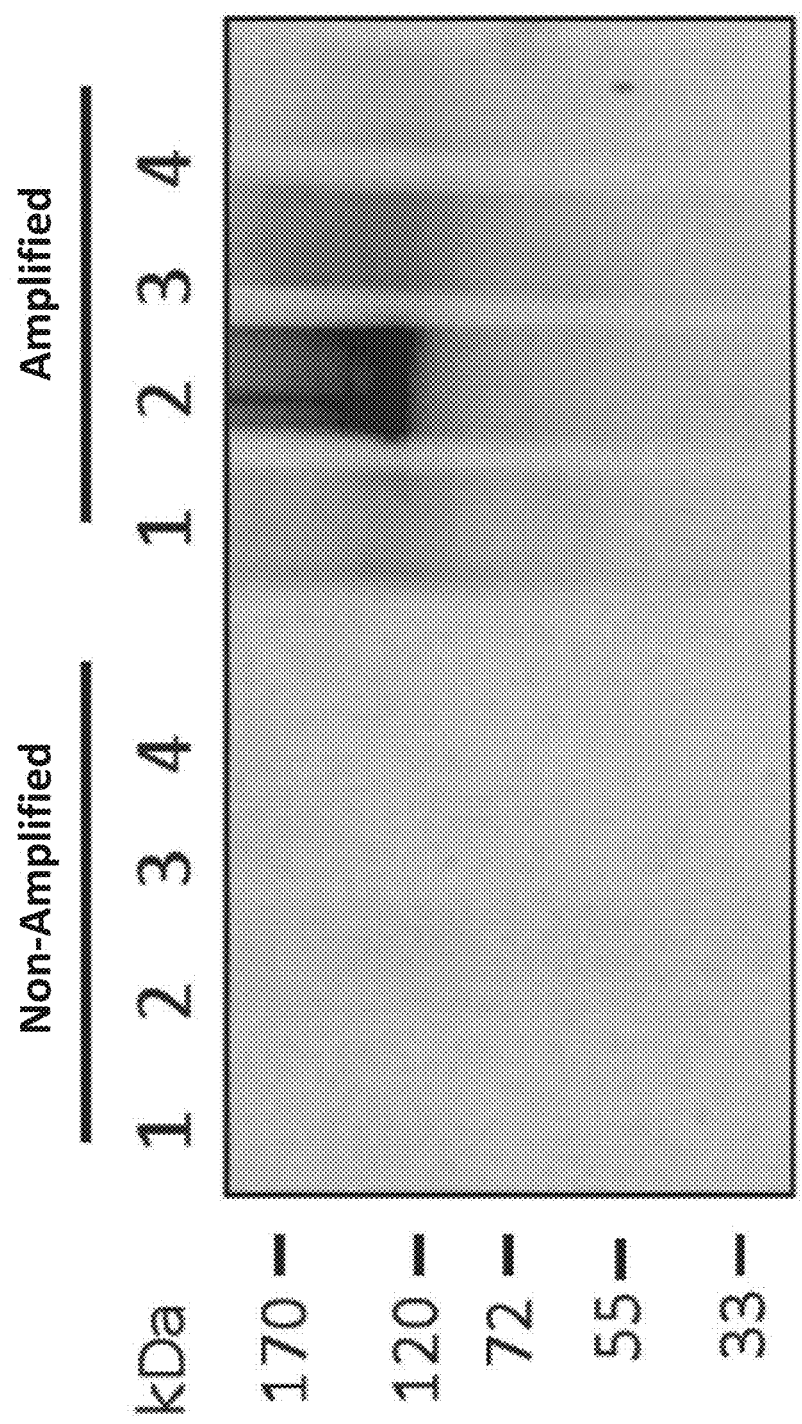
FIG. 12 is a western blot showing the results of amplification of Aβ aggregation by cycles of incubation/sonication in the presence of distinct quantities of synthetic Aβ oligomers monitored by Western blot after protease digestion.

Example 10: Sonication and Shaking are Effective with Various Detection Methods FIG. 12 is a western blot showing the results of amplification of Aβ aggregation by using sonication instead of shaking as a mean to fragment aggregates. The experiment was done in the presence of distinct quantities of synthetic Aβ oligomers. Samples of 10 μg/ml of seed-free monomeric Aβ1-42 were incubated alone (lane 1) or with 300 (lane 2), 30 (lane 3) and 3 (lane 4) fmols of, misfolded Aβ. Samples were either frozen without amplification (non-amplified) or subjected to 96 PMCA cycles (amplified), each including 30 min incubation followed by 20 sec sonication. Aggregated Aβ was detected by western blot using anti-Aβ antibody after treatment of the samples with proteinase K (PK). In our experiments, it was observed that detection using thioflavin T fluorescence was not compatible with sonication, but works very well with shaking as a physical disruption method. FIG. 12 shows that using a different detection method for the Aβ aggregates, in this case Western Blotting, sonication works as well as shaking.

Example 11: Production of Monomeric Aβ as PMCA Substrate

Seed-free monomeric Aβ was obtained by size exclusion chromatography. Briefly, an aliquot of a 1 mg/mL peptide solution prepared in dimethylsulfoxide was fractionated using a Superdex 75 column eluted at 0.5 mL/min with 10 mM sodium phosphate at pH 7.5. Peaks will be detected by UV absorbance at 220 nm. The peak corresponding to 4-10 kDa molecular weight containing monomer/dimmers of Aβ was collected and concentration determined by amino acid analysis. Samples were stored lyophilized at −80° C.

Example 12: Production and Purification of Aβ

*E. coli* cells harboring pET28 GroES-Ub-Aβ42 plasmid were grown in Luria broth (LB) at 37° C., and expression was induced with 0.4 mM IPTG. After 4 h, cells were harvested and lysed in a lysis buffer (20 mM Tris-Cl, pH 8.0, 10 mM NaCl, 0.1 mM PMSF, 0.1 mM EDTA and 1 mM β-mercaptoethanol) and centrifuged at 18,000 rpm for 30 min. Inclusion bodies were re-suspended in a resuspension buffer (50 mM Tris-Cl, pH 8.0, 150 mM NaCl, and 1 mM DTT) containing 6 M urea. Insoluble protein was removed by centrifugation at 18,000 rpm for 30 min. The supernatant containing GroES-Ub-Aβ42 fusion protein will be collected. To cleave off Aβ42 from fusion protein, the fusion protein was diluted 2-fold with resuspension buffer and treated with recombinant de-ubiquinating enzyme (Usp2cc) 1:100 enzyme to substrate molar ratio at 37° C. for 2 h. After that, samples was loaded on a C18 column (25 mm×250 mm, Grace Vydac, USA). Aβ42 was purified with a solvent system buffer 1 (30 mM ammonium acetate, pH 10, 2% acetonitrile) and buffer 2 (70% acetonitrile) at a flow rate 10 ml/min using a 20-40% linear gradient of buffer 2 over 35 min. Purified Aβ42 was lyophilized and stored at −80° C., until use.

Example 13: Detection of αS Seeds by PD-PMCA

Figure 13A:
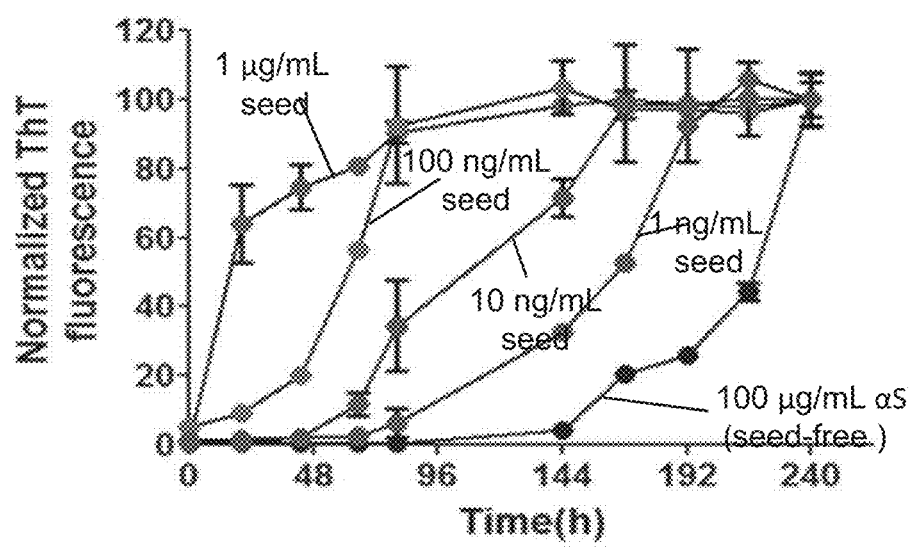
FIG. 13A is a graph of Thioflavin T fluorescence versus time showing the detection of αS seeds by PD-PMCA.

EXAMPLE 13A: Seeding of αS aggregation was studied by incubating a solution of seed-free αS in the presence of Thioflavin T with or without different quantities of synthetic soluble oligomeric αS protein: Control (no αS oligomer); or 1 ng/mL, 10 ng/mL, 100 ng/mL, and 1 μg/mL of the synthetic soluble oligomeric αS protein seed. αS-PMCA general procedure: Solutions of 100 μg/mL αS seed-free αS in PBS, pH 7.4 (200 μL total volume) were placed in opaque 96-wells plates and incubated alone or in the presence of the indicated concentrations of synthetic αS aggregates or 40 μL of CSF aliquots. Samples were incubated in the presence of 5 μM Thioflavin T (ThT) and subjected to cyclic agitation (1 min at 500 rpm followed by 29 min without shaking) using an Eppendorf thermomixer, at a constant temperature of 22° C. At various time points, ThT fluorescence was measured in the plates at 485 nm after excitation at 435 nm using a plate spectrofluorometer. FIG. 13A is a graph of Thioflavin T fluorescence as a function of time, showing the detection of αS seeds by PD-PMCA, using the indicated concentration of synthetic soluble oligomeric αS protein seeds. The peptide concentration, temperature and pH of the buffer were monitored to control the extent of the lag phase and reproducibility among experiments. Aggregation of monomeric αS protein was observed in the presence of 1 ng/mL, 10 ng/mL, 100 ng/mL, and 1 µg/mL αS of the synthetic soluble oligomeric αS protein seed.

Figure 13B:
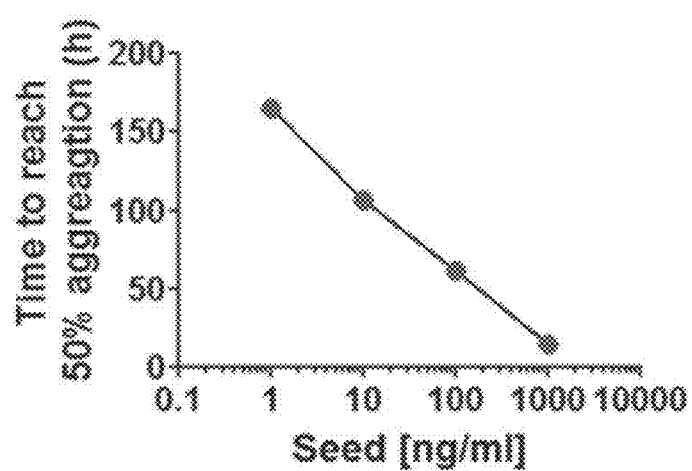
FIG. 13B is a graph of time to reach 50% aggregation plotted as a function of the indicated amounts αS seeds.

EXAMPLE 13B: The time to reach 50% aggregation as a function of amounts of αS seeds added was determined using the samples in EXAMPLE 1A. FIG. 13B is a graph showing time to reach 50% aggregation plotted as a function of amounts of αS seeds added.

Example 14: αS-PMCA Detects Oligomeric αS in the Cerebrospinal Fluid of PD Patients Detection of seeding activity in human CSF samples from controls and PD patients was performed by PD-PMCA. Purified seed free alpha-synuclein (100 µg/mL) in PBS, pH 7.4 was allowed to aggregate at 37° C. with shaking at 500 rpm in the presence of CSF from human patients with confirmed PD, AD or non-neurodegenerative neurological diseases (NND). The extend of aggregation was monitored by Thioflavin fluorescence at 485 nm after excitation at 435 nm using a plate spectrofluorometer.

Aliquots of CSF were obtained from PD patients, cognitively normal individuals affected by non-degenerative neurological diseases (NND), and patients affected by Alzheimer's disease (AD). Test CSF samples were obtained from patients with the diagnosis of probable PD as defined by the DSM-IV and determined using a variety of tests, including routine medical examination, neurological evaluation, neuropsychological assessment, and magnetic resonance imaging. CSF samples were collected in polypropylene tubes following lumbar puncture at the L4/L5 or L3/L4 interspace with atraumatic needles after one night fasting. The samples were centrifuged at 3,000 g for 3 min at 4° C., aliquoted and stored at −80° C. until analysis. CSF cell counts, glucose and protein concentration were determined. Albumin was measured by rate nephelometry. To evaluate the integrity of the blood brain barrier and the intrathecal IgG production, the albumin quotient (CSF albumin/serum albumin)×$10^3$ and the IgG index (CSF albumin/serum albumin)/(CSF IgG/serum IgG) were calculated. The study was conducted according to the provisions of the Helsinki Declaration and was approved by the Ethics Committee.

Figure 14:
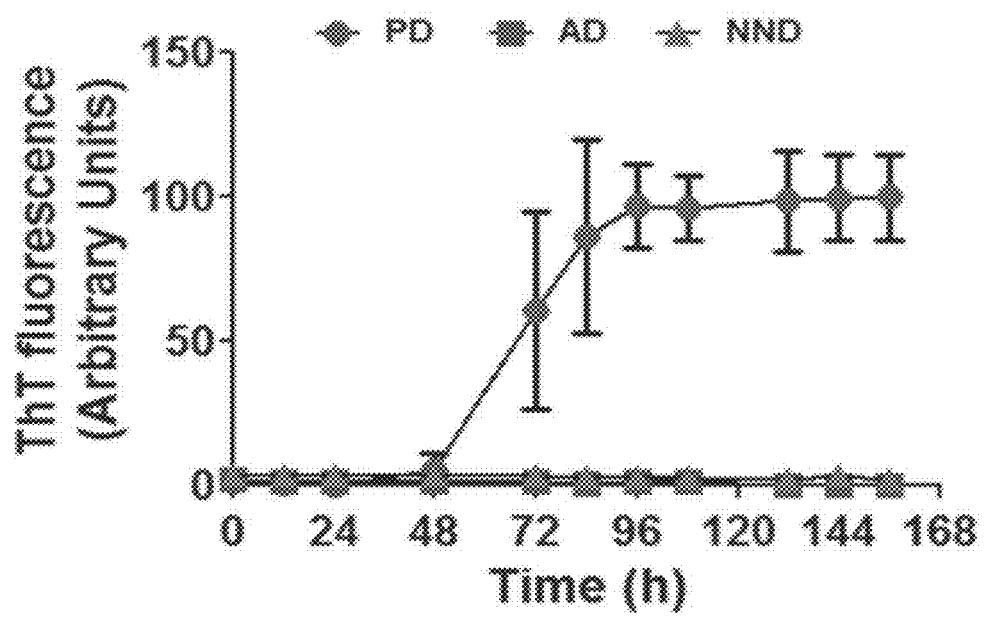
FIG. 14 shows detection of αS seeds in CSF samples from human PD patients by PD-PMCA, versus controls with Alzheimer's disease (AD) or a non-neurodegenerative disease (NND).

The experiments as well as the initial part of the analysis were conducted blind. FIG. 14 is a graph of αS oligomerization versus time, measured as a function of ThT fluorescence labeling, showing the average kinetics of αS aggregation of representative samples from the PD, AD, and NND groups.

The results indicate that CSF from PD patients significantly accelerates αS aggregation as compared to control CSF ($P<0.001$). The significance of the differences in αS aggregation kinetics in the presence of human CSF samples was analyzed by one-way ANOVA, followed by the Tukey's multiple comparison post-test. The level of significance was set at $P<0.05$. The differences between PD and samples from the other two groups were highly significant with $P<0.001$ (***).

Example 15: Specificity of Immuno Capturing

FIG. 15 shows Table 3, demonstrating the ability of different sequence or conformational antibodies to capture αS oligomers. The capacity to capture oligomers was measured by spiking synthetic αS oligomers in healthy human blood plasma and detection by αS-PMCA. The first column shows various antibodies tested and corresponding commercial sources. The second column lists the epitope recognition site on the αS protein of the diverse sequence antibodies used in this study. The third column indicates the observed ability of specific antibodies to capture the αS oligomers. The symbols indicate that the detection limits using the different antibodies were: <12 fmol (+++); between 10-100 fmol (++); >1 pmol (+) and not significantly higher than without capturing reagent (−). Alpha/beta-synuclein antibody N-19 (N-terminal epitope) and alpha-synuclein antibody C-20-R (C-terminal epitope) showed the best results; and alpha-synuclein antibody 211 (epitope: amino acids 121-125) showed very good results; alpha-synuclein antibody 204 (epitope: fragment 1-130) showed good results; and 16 ADV Mouse IgG1 (conformational epitope) showed no result.

Example 16: Solid Phase Immuno Capturing

Figure 16A:
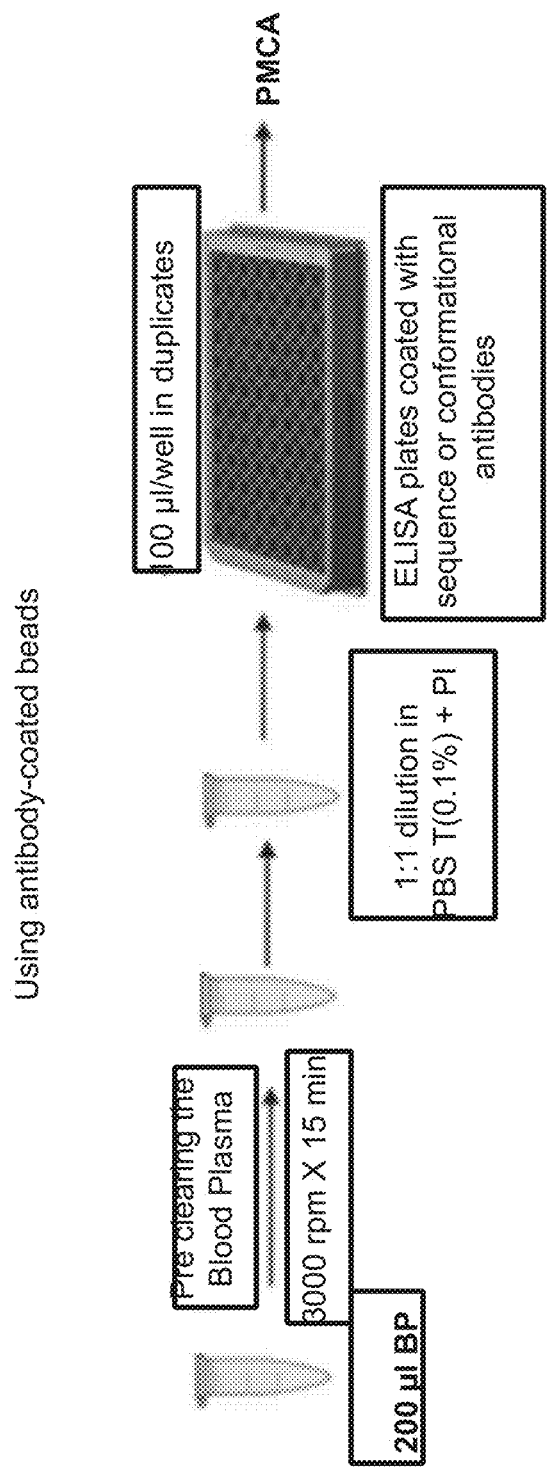
FIG. 16A is a schematic representation of an ELISA solid phase method employed to capture αS oligomers.
Figure 16B:
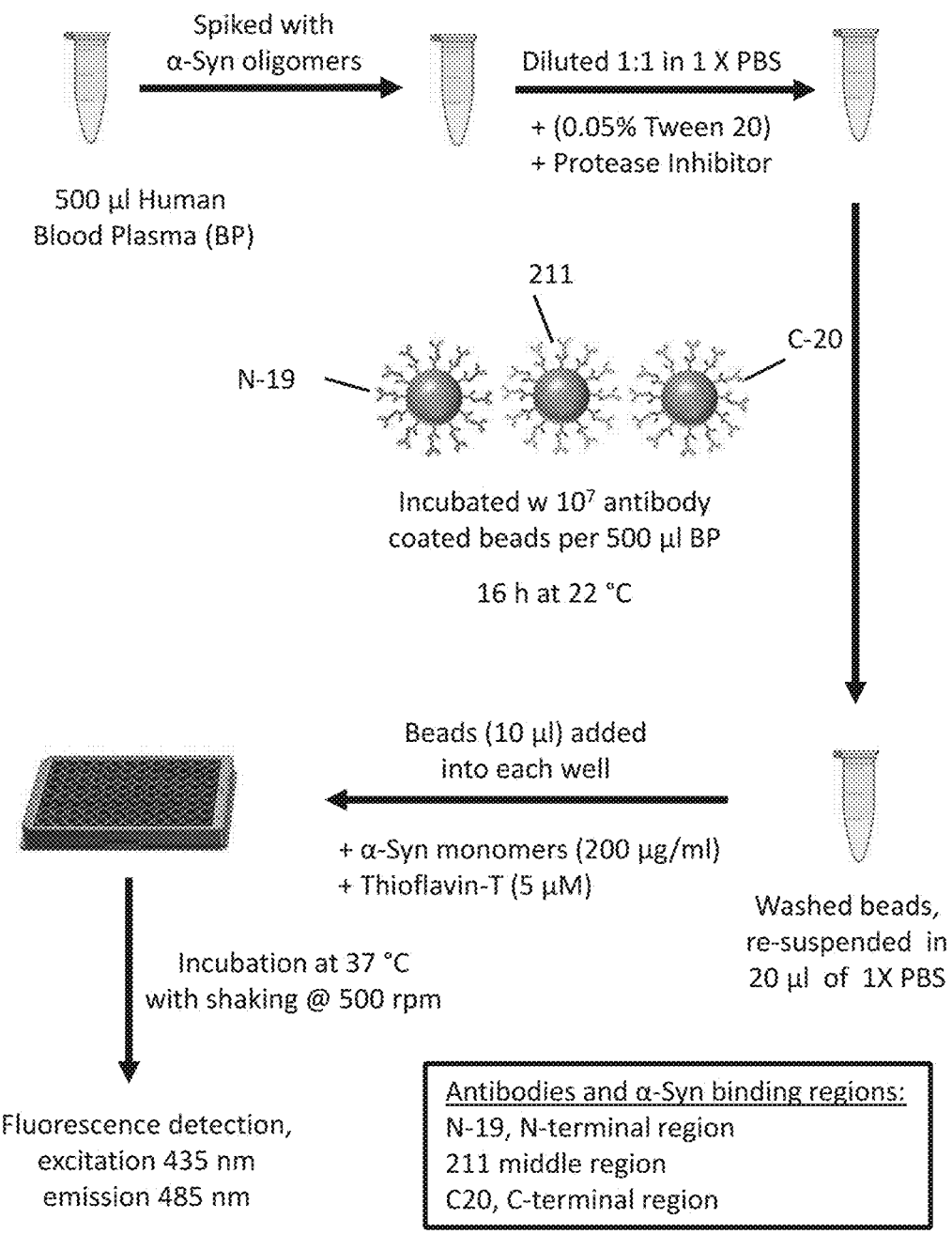
FIG. 16B is a schematic representation of a magnetic bead solid phase method employed to capture αS oligomers.

FIGS. 16A and 16B are schematic representations of two solid phase methods used to capture soluble, misfolded αS protein from complex samples such as blood plasma. Strategy 1 employed ELISA plates pre-coated with specific antibodies bound to a solid phase on the ELISA plate. After washing the plates, the αS-PMCA reaction was carried out in the same plates. Strategy 2 used magnetic beads as the solid phase coated with specific antibodies. This approach provided concentration of the samples.

Figure 17A:
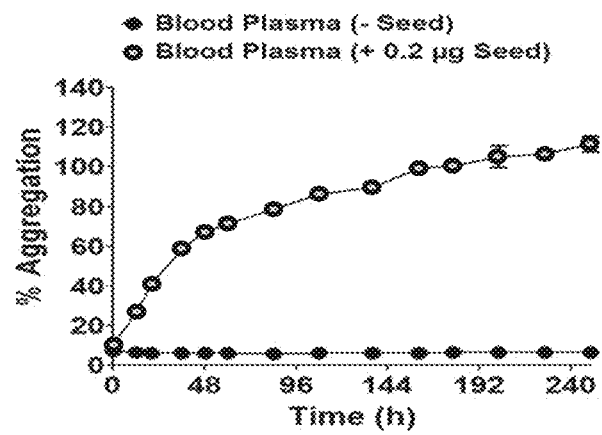
FIGS. 17A, 17B, and 17C are a series of graphs that show the results of immunoprecipitation/aggregation of α-Synuclein oligomers from human blood plasma using three different α-Synuclein antibodies.
Figure 17B:
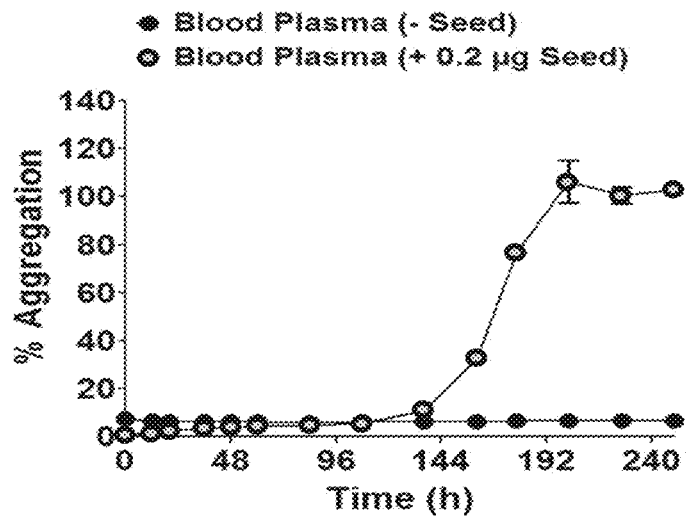
Figure 17C:
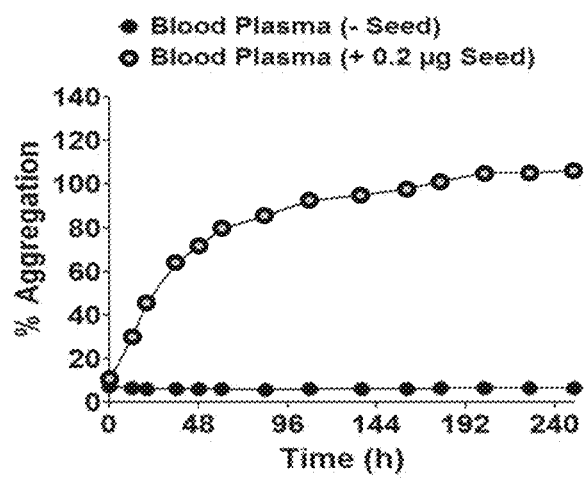

Example 17: αS-PMCA for the Detection of α-Synuclein Oligomers Spiked in Human Blood Plasma Immunoprecipitation of α-Synuclein oligomers from human blood plasma was performed by anti-α-Synuclein antibody-coated beads (Dynabeads) and a seeding aggregation assay using α-Synuclein monomers as seeding substrate along with thioflavin-T for detection. The anti-α-Synuclein coated beads ($1 \times 10^7$ beads) were incubated with human blood plasma (500 µL) with α-Synuclein seeds (+0.2 µg Seed) and without α-Synuclein seeds (−Seed). After immunoprecipitation, the beads were re-suspended in 20 µL of reaction buffer (1×PBS), and 10 µL of beads were added to each well of a 96-well plate. The aggregation assay was performed by adding α-Synuclein monomers (200 µg/mL) and thioflavin-T (5 µM). The increase in florescence was monitored by a fluorimeter using an excitation of 435 nm and emission of 485 nm. FIG. 17A illustrates immunoprecipitation/aggregation results with N-19 antibody in blood plasmas with and without seed. FIG. 17B illustrates immunoprecipitation/aggregation results with 211 antibody in blood plasmas with and without seed. FIG. 17C illustrates immunoprecipitation/aggregation results with C-20 antibody in blood plasmas with and without seed.

Figure 18A:
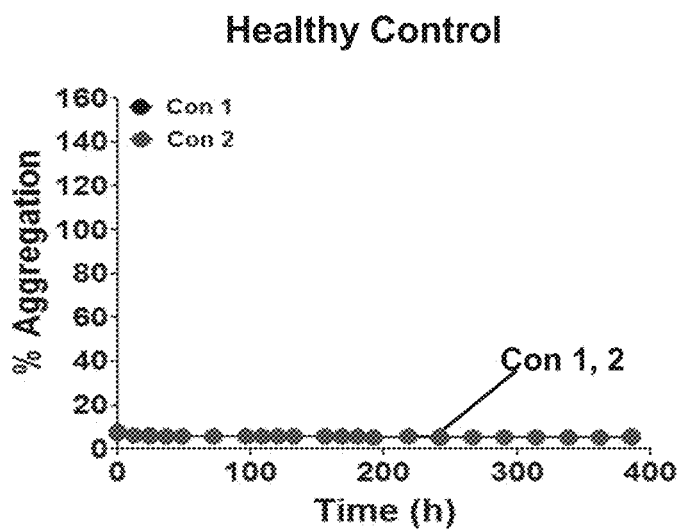
FIGS. 18A, 18B, and 18C are a series of graphs that show the results of detection for αS seeds in CSF samples.
Figure 18B:
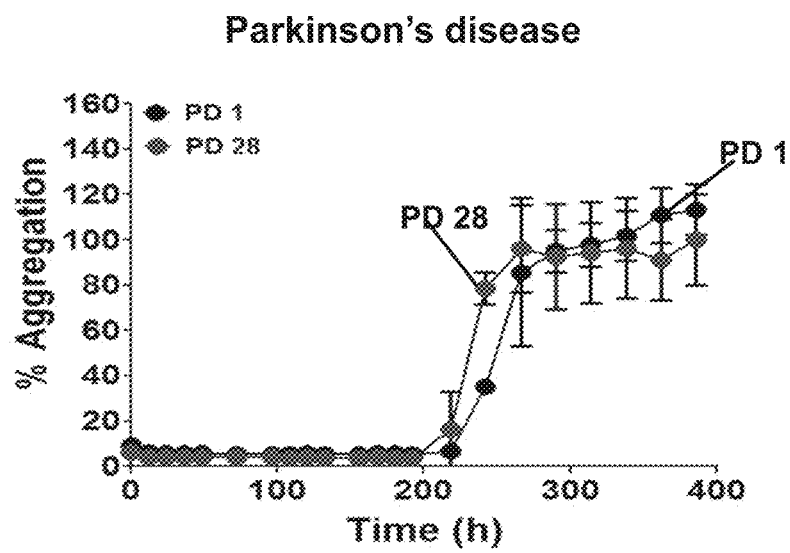
Figure 18C:
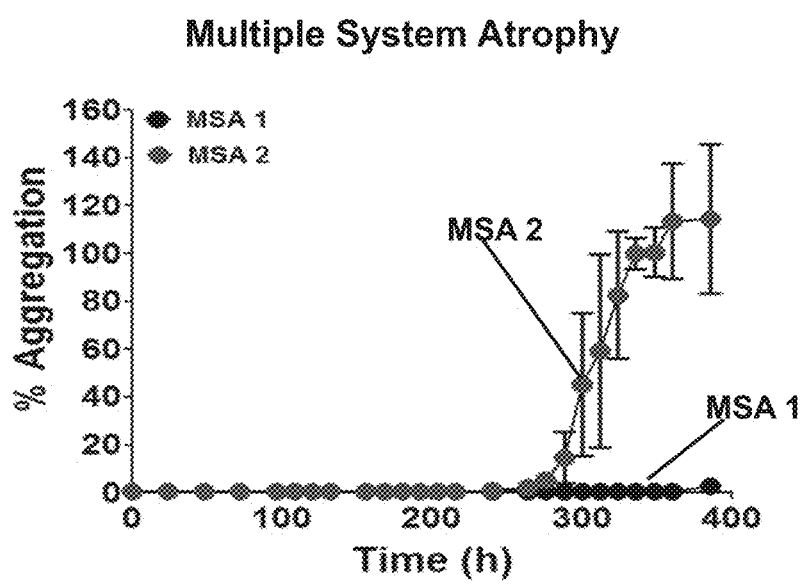

Example 18: αS-PMCA Detects Oligomeric αS in the Cerebrospinal Fluid of Patients Affected by PD and Multiple System Atrophy with High Sensitivity and Specificity To study the efficiency of αS-PMCA for biochemical diagnosis of PD and related α-synucleinopathies, such as multiple system atrophy (MSA), tests were performed on CSF from many patients affected by these diseases as well as controls affected by other diseases. FIGS. 18A, 18B, and 18C show detection of seeding activity in human CSF samples from controls and patients affected by PD and MSA, respectively, using αS-PMCA. Purified seed free alpha-synuclein (100 µg/mL) in buffer MES, pH 6.0 was allowed to aggregate at 37° C. with shaking at 500 rpm in the presence of CSF from human patients and controls. The extent of aggregation was monitored by Thioflavin T fluorescence at 485 nm after excitation at 435 nm using a plate spectrofluorometer.

Test CSF samples were obtained from patients with the diagnosis of probable PD and MSA as defined by the DSM-IV and determined using a variety of tests, including routine medical examination, neurological evaluation, neuropsychological assessment, and magnetic resonance imaging. CSF samples were collected in polypropylene tubes following lumbar puncture at the L4/L5 or L3/L4 interspace with atraumatic needles after one night fasting. The samples were centrifuged at 3,000 g for 3 min at 4° C., aliquoted and stored at −80° C. until analysis. CSF cell counts, glucose and protein concentration were determined. Albumin was measured by rate nephelometry. The study was conducted according to the provisions of the Helsinki Declaration and was approved by the Ethics Committee.

The experiments as well as the initial part of the analysis were conducted blind. FIGS. 18A, 18B, and 18C are graphs of αS aggregation versus time, measured as a function of ThT fluorescence labeling, showing the average kinetics of αS aggregation, respectively, for controls and two representative samples from the PD and MSA groups.

The results indicate that CSF from PD patients significantly accelerates αS aggregation as compared to control CSF (P<0.001). The significance of the differences in αS aggregation kinetics in the presence of human CSF samples was analyzed by one-way ANOVA, followed by the Tukey's multiple comparison post-test. The level of significance was set at P<0.05. The differences between PD and samples from the other two groups were highly significant with P<0.001 (***).

The outcome of the overall set of 29 PD or MSA samples and 41 controls was that 26 of the 29 PD or MSA samples were positive, whereas 3 of the 41 control samples were positive, which corresponded to a 90% sensitivity and 93% specificity.

Example 19: Synthesis of Full-Length 4R Tau Protein and Seeds

Figure 19:
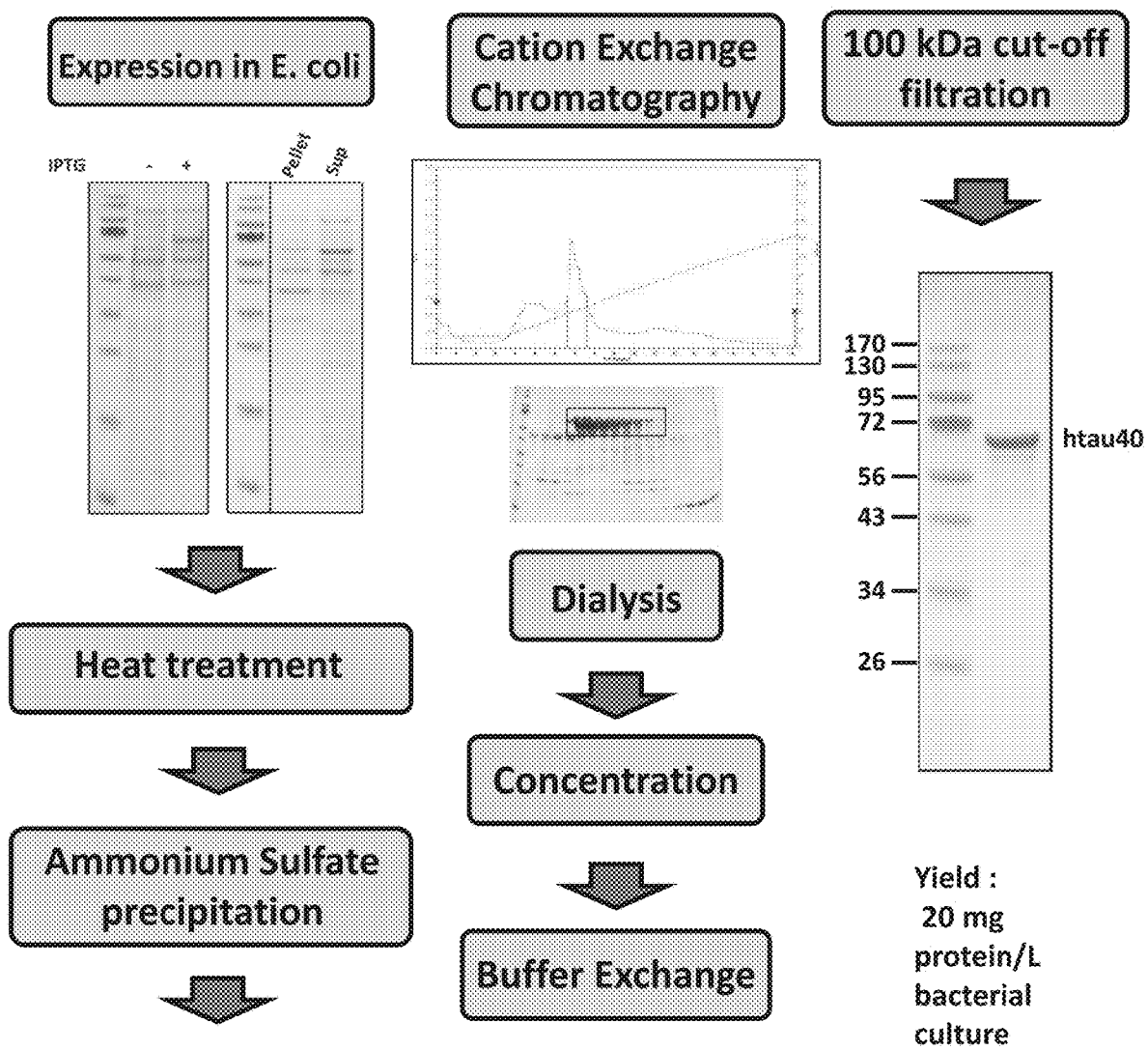
FIG. 19 is a flow chart showing the preparation and purification of recombinant full-length 4R tau protein.

FIG. 19 is a flow chart showing the preparation and purification of recombinant full-length 4R tau protein. A gene for hTau40 was transfected into *E. coli* and incubated under standard conditions to express the hTau40. After a period of growth, the *E. coli* cells were pelted, lysed, heat treated, and precipitated with ammonium sulfate to produce a crude product. The crude product was subjected to cation exchange chromatography, dialysis, then concentrated and the buffer exchanged. Cut-off filtration at a mass of 100 kDa was employed to further purify the hTau40. The yield of the purified hTau 40 was 20 mg/L of bacterial culture. Full-length 4R Tau seeds were then prepared by incubating hTau 40 monomer with 12.5 μM heparin in 10 mM HEPES pH 7.4, 100 mM NaCl for 3 days at 37° C. using cyclic agitation (1 min shaking at 500 rpm followed by 29 min without shaking).

Example 20A: Tau PMCA

Figure 20A:
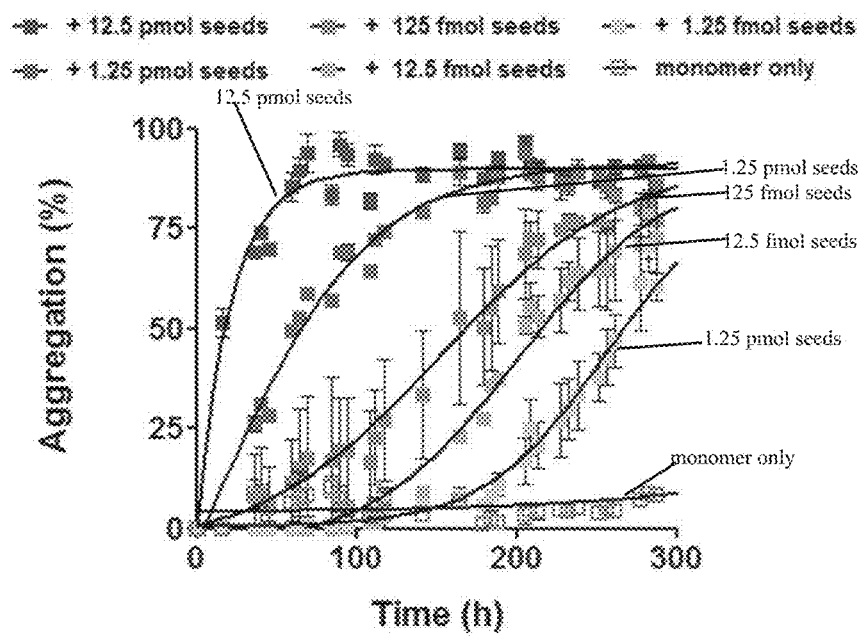
FIG. 20A is a graph of aggregation in % according to ThT fluorescence for various initial amounts of tau seeds and a control. The values in FIG. 20A are the mean of two replicates, with the error bars indicating standard deviation.
Figure 20B:
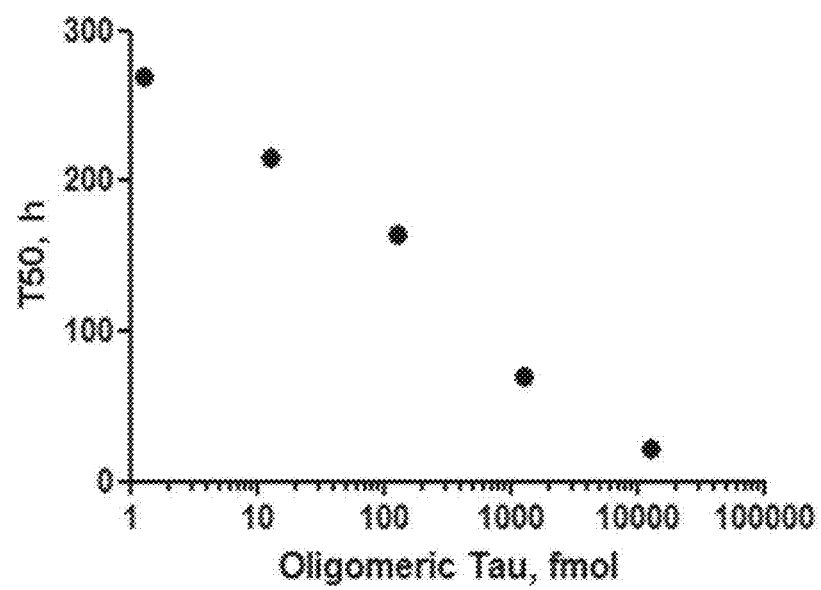
FIG. 20B is a graph of $T_{50}$, the time to 50% aggregation as measured by ThT fluorescence versus the log of the amount of oligomeric tau seeds in fmol.

A Tau-PMCA assay was performed on 96 well plates using 12.5 μM Tau monomer, 1.25 μM heparin, 5 μM Thioflavin T, using cyclic agitation (1 min shaking at 500 rpm followed by 29 min without shaking). Seeds were added to the wells in amounts of 12.5 pmol, 1.25 pmol, 125 fmol, 12.5 fmol, and 1.25 fmol. Controls were performed without seeds. Aggregation was followed over time by ThT fluorescence using a plate spectrofluorometer (excitation: 435; emission: 485). FIG. 20A is a graph of aggregation in % for the various initial amounts of seeds and the control. The values in FIG. 20A are the mean of two replicates, with the error bars indicating standard deviation. FIG. 20B is a graph of $T_{50}$, the time to 50% aggregation as measured by ThT fluorescence versus the log of the amount of oligomeric tau seeds in fmol.

Example 20B: Tau PMCA

For optimization of the tau-PMCA assay, full-length human Tau40 that includes four imperfect tandem microtubule binding repeats (4R). Tau oligomers were generated by incubation of full-length Tau (50 μM) in the presence of heparin (12.5 μM) for 3 days at 37° C. Seeds were characterized by ability to seed tau aggregation, binding to thioflavin T, western blot and electron microscopy. The preformed aggregates were used to nucleate and induce the aggregation of Tau. For the assay, seed-free monomeric tau (15 μM) in 10 mM HEPES pH 7.4, 100 mM NaCl containing 3 μM of heparin in the absence or the presence of different quantities of synthetic seeds was subjected to cycles of tau-PMCA by incubating at 20° C. for 29.5 min followed by shaking for 30 sec at 500 rpm. Under these conditions, Tau was only observed to aggregate in the presence of preformed seeds and the kinetic of aggregation was dependent on the amount of seeds added. Importantly, the PMCA signal was observed to be directly proportional to the amount of seeds added to the reaction. This assay corresponded to a detection threshold of 0.125 pg of oligomeric tau. This detection threshold corresponds to ~2 atto-mol, based on the molecular weight of the tau monomer, or 0.15 atto-mol, based on the molecular weight of a 12-mer oligomer as a proxy for average oligomer size.

Example 20C: Tau PMCA

Figure 20C:
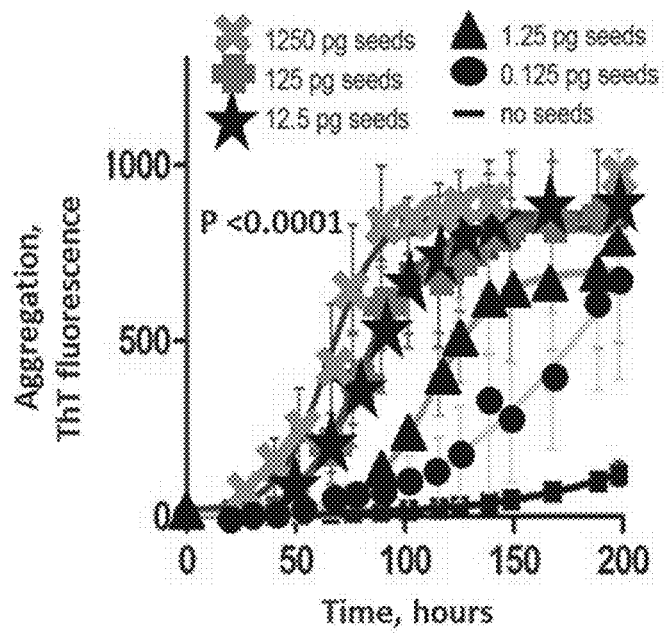
FIG. 20C is a graph of aggregation followed over time by ThT fluorescence.
Figure 20D:
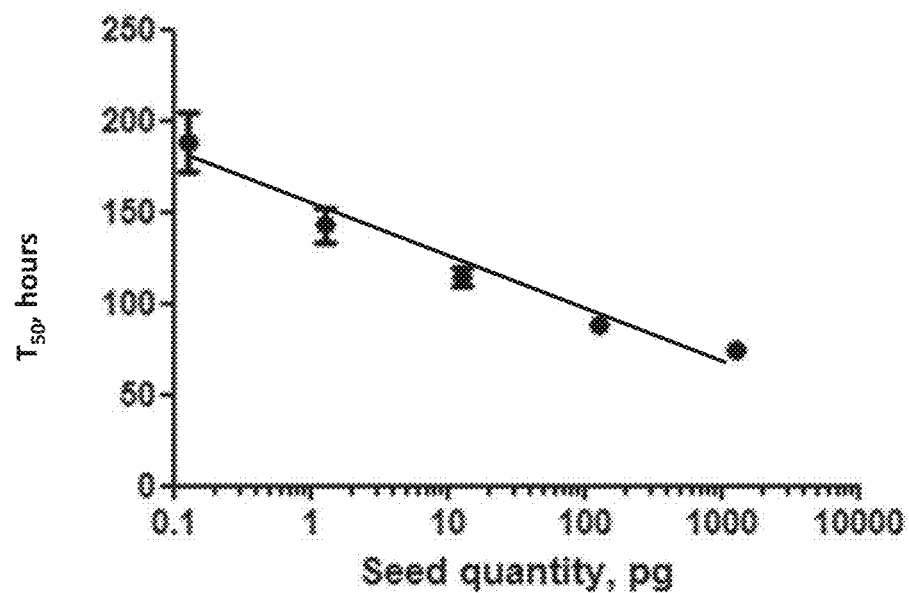
FIG. 20D is a graph of the relationship between the quantity of tau oligomers and the Tau-PMCA signal (time to reach 50% aggregation).

A further Tau-PMCA assay was performed using full-length Tau seeds prepared by incubating Tau monomer with 12.5 μM heparin in 10 mM HEPES pH 7.4, 100 mM NaCl for 3 days at 37° C. with shaking. The assay was performed on 96 well plates using 12.5 μM Tau monomer, 1.25 μM heparin, and 5 μM Thioflavin T, using cyclic agitation (1 min shaking at 500 rpm followed by 29 min without shaking). FIG. 20C is a graph of aggregation followed over time by ThT fluorescence using a plate spectrofluorometer (excitation: 435; emission: 485). FIG. 20C shows the mean and SD of two replicates. FIG. 20D is a graph of the relationship between the quantity of tau oligomers and the Tau-PMCA signal (time to reach 50% aggregation).

Example 20D: Tau PMCA is Reproducible

A large scale experiment was conducted to evaluate the robustness and reproducibility of the tau-PMCA assay to analyze the performance at four different times (0, 14, 28 and 30 days) with or without freezing/thawing. Two different set of synthetic seeds and five different concentrations of synthetic seeds (1250, 125, 12.5, 1.25 and 0.125 pg of seeds) were employed, spiked either in buffer or control CSF. Each sample was run in triplicate. The experiment encompassed several steps, including the large-scale expression and purification of tau in quantities needed to perform all experiments, quality control of the material produced, generation and characterization of synthetic tau oligomeric seeds and the tau-PMCA experiments to investigate assay precision and reproducibility in buffer and in the biological matrix (CSF). In total the experiment employed 32 different conditions (2 different seeds×4 time points x: 2 manners of dilution (freezing or not freezing)×2 different matrices (buffer or CSF)). Since all conditions were tested with five different concentrations of oligomeric seeds and each was done in triplicate, the entire experiment involved 480 wells. The protein concentration, buffer and PMCA conditions were the same as EXAMPLE 20B. From the 32 conditions tested only one gave results that were slightly significantly different from the others, indicating high precision and reproducibility. FIGS. 20E-20L are a series of graphs that display the aggregation results based on ThT fluorescence of 8 of the conditions tested, including 4 different time points (0, 7, 14 and 30 days) with samples subjected to freezing and thawing or not and in the presence of buffer or CSF, and two different seed preparations (FIGS. 20E-20H and FIGS. 20I-20L). FIGS. 20E-20L demonstrate that the results obtained are very similar between the triplicates, different time points, and distinct seeds. Data correspond to average±standard error of triplicate samples. Tau substrate in the absence of seeds was not observed to aggregate under any condition within the time in which experiments were done.

To analyze the reproducibility of the assay, Tso values (time to reach 50% aggregation) for the experiments in the presence of 1250 pg of Tau seeds. The Tso values for the experiments done at different days, with one of two seed preparations A or B and using fresh or frozen seeds did not show any statistically significant difference and an average Tso of 71.5±1.8 h was obtained. Similar non-significant differences were observed for the studies done in the presence of all the other seed concentrations or for the experiments done in buffer. FIG. 20M is a table of Tso values showing reproducibility across 16 different conditions. All values were analyzed by one way ANOVA, followed by Tukey multiple comparison test.

Example 20E: Tau PMCA is Specific

Figure 20N:
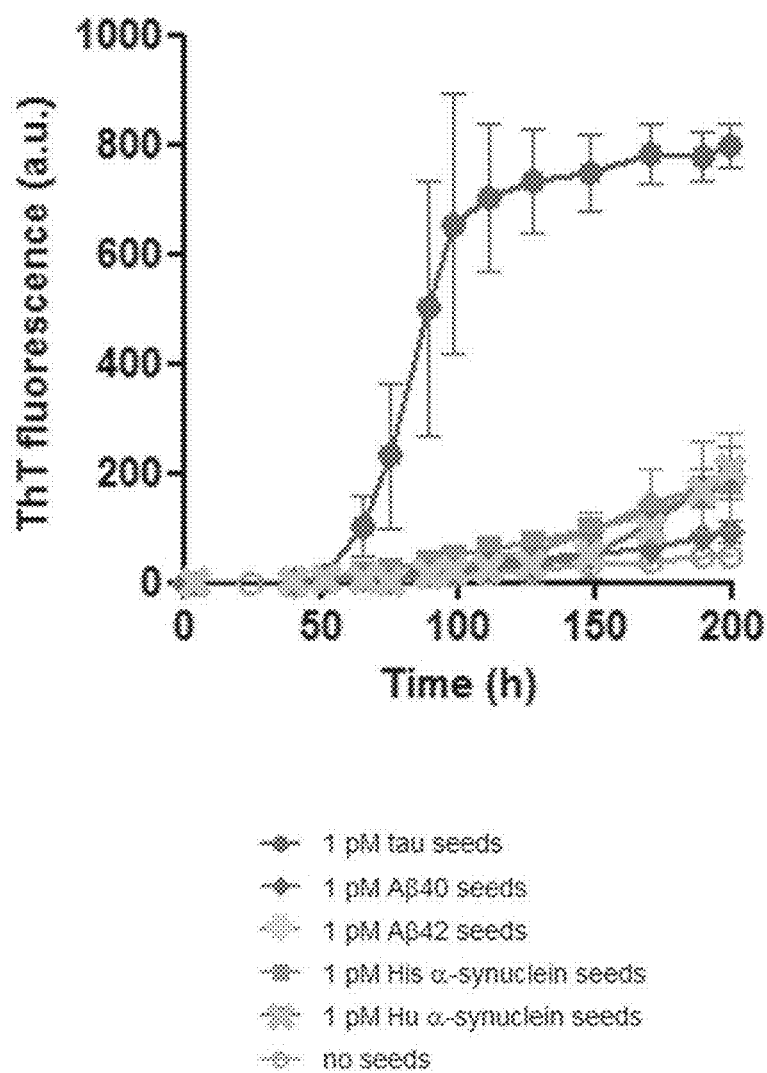
FIG. 20N is a graph of ThT fluorescence vs time for the tau assay seeded with 1 pm of tau, Aβ40, AB42, His αSyn, Hu αSyn, and a control with no seeds.

The tau PMCA assay was investigated for specificity, particularly for the ability to detect aggregates composed of other amyloidogenic proteins. Aβ and αSyn oligomeric species were prepared and used to cross-seed monomeric tau. FIG. 20N is a graph of ThT fluorescence vs time for the tau assay seeded with 1 pm of tau, Aβ40, AB42, His αSyn, Hu αSyn, and no seeds. FIG. 20N shows that no significant signal was detectable in the presence of Aβ or αSyn seeds and no signal was detected before about 100 h, even when the concentration of these particles was relatively high (equivalent to 2 ng of tau seeds). These Aβ are αSyn seeds are very efficient in inducing aggregation in the respective Aβ- or αSyn-PMCA assays described in preceding EXAMPLES. These results indicate that under the conditions and concentrations used there is no cross-seeding between other protein aggregates and that tau-PMCA is specific for detecting tau oligomers.

Example 21A: Tau PMCA Detects Tau in Human CSF

Figure 21A:
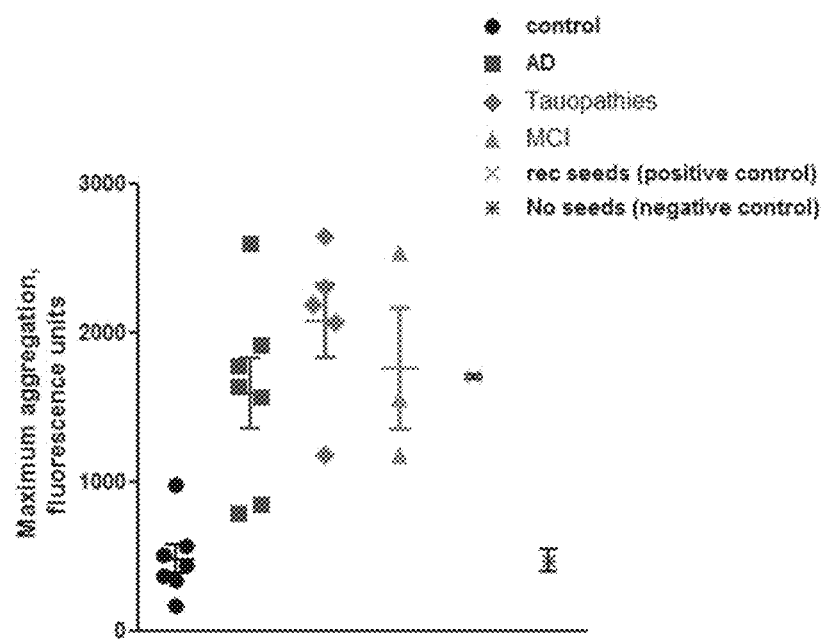
FIG. 21A is a graph showing ThT fluorescence at 447 h of incubation for patients with AD, patients with MCI, patients with other tauopathies, positive controls using samples of healthy CSF spiked with synthetic Tau oligomers (12.5 fmol), negative controls of samples of healthy CSF without Tau seeds; and control patients with other neurological diseases.

Human CSF samples from AD patients (7 cases), 5 other Tauopathies (1FTD, 2PSP, 2CBD), people affected by mild cognitive impairment (MCI) and controls affected by other neurological diseases (7 samples) were analyzed by Tau-PMCA. FIG. 21A is a graph showing ThT fluorescence at 447 h of incubation, in which most samples have reached the maximum fluorescence. Positive controls used samples of healthy CSF spiked with synthetic Tau oligomers (12.5 fmol). Negative controls correspond to samples of healthy CSF without Tau seeds. FIG. 21A shows that patients with AD, other tauopathies, and MCI showed Tau aggregation significantly above the negative control and consistent with the positive control. 6 of the 7 control patients with other neurological diseases were consistent with the negative control. One control patients in the other neurological disease group showed maximum fluorescence consistent with a tauopathy. This may indicate an undiagnosed tauopathy in that patient, or alternatively, inadvertent contamination.

Example 21B: Tau PMCA Detects Tau in Human CSF

Figure 21B:
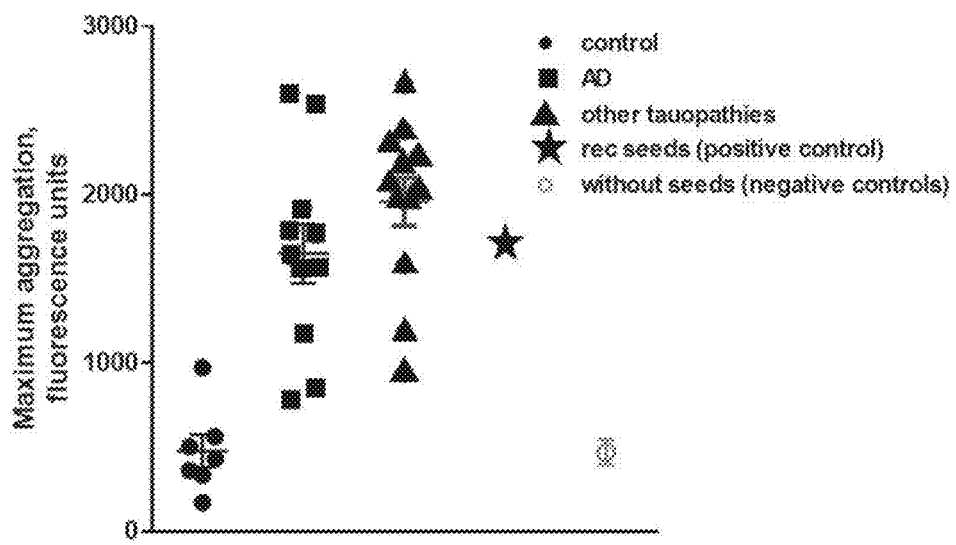
FIG. 21B shows fluorescence signals for samples from patients with AD or other tauopathies for tau-PMCA comparable to that observed in samples containing recombinant tau oligomers.

Human CSF samples from 11 patients affected by AD, 11 from other tauopathies (4 PSP, 1 FTD, 5 CBD and 1 CTE) and 7 controls affected from unrelated neurological disorders were examined. Positive controls were prepared by spiking CSF with 20 ng of recombinant tau oligomers. Negative controls were healthy CSF without tau seeds. FIG. 21B is a graph of fluorescence signals for samples from patients with AD or other tauopathies for tau-PMCA comparable to that observed in samples containing recombinant tau oligomers. Consequently, samples from patients with AD or other tauopathies were able to accelerate tau aggregation. Conversely, 6 out of 7 of the controls produced a low signal in tau-PMCA, with values equivalent to those observed in CSF without seeds. Despite the small sample size, the differences between controls and patients were statistically significant. These positive results indicate that tau-PMCA is capable of detecting tau aggregates in CSF of patients. FIG. 21B shows the maximum ThT fluorescence, expressed as arbitrary units. Differences were analyzed by one-way ANOVA followed by the Tukey's multiple comparison post-test. **$P<0.01$.

Example 22: Tau PMCA Detects Tau in Human CSF

Figure 22:
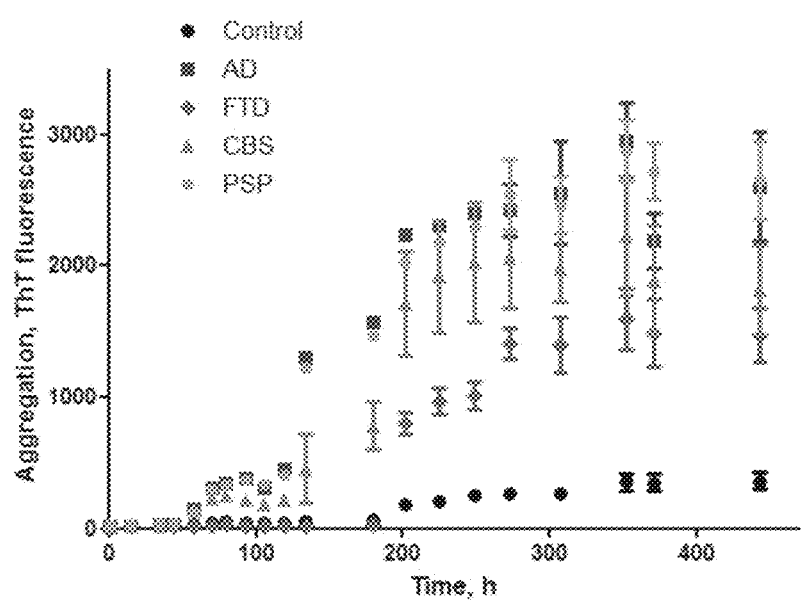
FIG. 22 is a graph showing aggregation % based on ThT versus time for patients affected by AD, FTD (frontotemporal dementia), CBD (corticobasal degeneration), and PSP (progressive supranuclear palsy), versus representative CSF samples from a control.

The performance of Tau-PMCA assay was examined in the presence of representative CSF samples from a control, and patients affected by AD, FTD (frontotemporal dementia), CBD (corticobasal degeneration), and PSP (progressive supranuclear palsy). The Tau-PMCA assay was performed on 96 well plates using 12.5 µM Tau monomer, 1.25 µM heparin, 5 µM Thioflavin T, using cyclic agitation (1 min shaking at 500 rpm followed by 29 min without shaking). Aggregation was followed over time by ThT fluorescence using a plate spectrofluorometer (excitation: 435; emission: 485). FIG. 22 is a graph showing aggregation % based on ThT versus time. The various tauopathies differed in $T_{50}$, amplification rate, and amplification extent. For example, the $T_{50}$ of PSP and AD samples was about the same at 150 h, while the PSP sample appeared to have a shorter lag phase, a lower amplification rate, and a lower extent of amplification compared to AD. CBD appeared to have a $T_{50}$ of about 175 h, with a lower amplification rate, and a lower extent of amplification compared to both AD and PSP. FTD appeared to have a $T_{50}$ of about 210 h, with a higher amplification rate, and a lower extent of amplification compared to each of AD, PSP, and CBD. The control CSF sample had a similar $T_{50}$ and amplification rate compared to FTD, with a far lower extent of amplification. The amplification in the control CSF sample may be due to spontaneous (seed-free) amplification, inadvertent contamination, or an undiagnosed tauopathy with somewhat similar kinetics to FTD.

Discussion

The present tau-PMCA may provide various advantages over other methods. For example, embodiments of the present invention are capable of detecting the critical tau misfolding molecular pathogenic event directly, by contrast with known indirect measures such as non-pathogenic biomarkers, measurement of the total pool of tau, of which only a small fraction forms the synapto-toxic oligomeric aggregates, or measurement of variously phosphorylated species of tau. Embodiments of the present specifically detect the misfolded tau oligomers that exhibit a key pathological feature of the disease, of seeding tau misfolding and thus spreading the damage in the brain during the disease. In addition, all the other methodologies detect the material present in the sample, PMCA detect the conversion of the protein we add to the reaction seeded by minute amounts of oligomeric seeds in the sample following the same principle that happens in the diseased brain.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. To the extent that the term "substantially" is used in the specification or the claims, it is intended to mean that the identified components have the relation or qualities indicated with degree of error as would be acceptable in the subject industry.

As used in the specification and the claims, the singular forms "a," "an," and "the" include the plural unless the singular is expressly specified. For example, reference to "a compound" may include a mixture of two or more compounds, as well as a single compound.

As used herein, the term "about" in conjunction with a number is intended to include ±10% of the number. In other words, "about 10" may mean from 9 to 11.

As used herein, the terms "optional" and "optionally" mean that the subsequently described circumstance may or may not occur, so that the description includes instances where the circumstance occurs and instances where it does not.

In addition, where features or aspects of the disclosure are described in terms of Markush groups, those skilled in the art will recognize that the disclosure is also thereby described in terms of any individual member or subgroup of members of the Markush group. As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, and the like. As a non-limiting example, each range discussed herein can be readily broken down into a lower third, middle third and upper third, and the like. As will also be understood by one skilled in the art all language such as "up to," "at least," "greater than," "less than," include the number recited and refer to ranges which can be subsequently broken down into sub-ranges as discussed above. Finally, as will be understood by one skilled in the art, a range includes each individual member. For example, a group having 1-3 cells refers to groups having 1, 2, or 3 cells. Similarly, a group having 1-5 cells refers to groups having 1, 2, 3, 4, or 5 cells, and so forth. While various aspects and embodiments have been disclosed herein, other aspects and embodiments will be apparent to those skilled in the art.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The various aspects and embodiments disclosed herein are for purposes of illustration and are not intended to be limiting, with the true scope and spirit being indicated by the following claims.

The invention claimed is:

1. A method for detecting the presence of tau aggregates in a human cerebrospinal fluid (CSF) sample, the method comprising:
   (A) providing the human CSF sample;
   (B) providing a first pre-incubation mixture that is free of tau seeds, the first pre-incubation mixture comprising:
      (1) a monomeric 4R tau protein having a concentration of about 12.5 µM;
      (2) heparin having a concentration of about 1.25 µM;
      (3) a buffer composition comprising about 10 mM HEPES and having a pH of about 7.4;
      (4) a salt composition comprising NaCl in a concentration of about 100 mM; and
      (5) Thioflavin T (ThT) in a concentration of about 5 µM,
   (C) combining the human CSF and the first pre-incubation mixture in a first well of a reaction vessel to form a first incubation mixture;
   (D) incubating the first incubation mixture at a temperature of about 37° C. with intermittent cyclic agitation cycles comprising about 1 minute of shaking at about 500 revolutions per minute followed by about 29 minutes without shaking to form a first incubated mixture;
   (E) illuminating the first incubated mixture with an excitation wavelength of about 435 nanometers and an emission wavelength of about 485 nanometers; and
   (F) determining a level of fluorescence during incubation, wherein an increase in the level of fluorescence of the first incubated mixture at maximum fluorescence of at least two times the standard deviation of the fluorescence of the first incubated mixture at maximum fluorescence compared to the level of fluorescence of the first incubated mixture at any time point up to about 50 hours of incubation with intermittent agitation cycles indicates the presence of tau aggregates in the human CSF sample.

2. The method of claim 1, further comprising:
(A) providing a CSF sample that is free of tau seeds as a negative control sample;
(B) providing a second pre-incubation mixture that is free of tau seeds, the second pre-incubation mixture comprising:
  (1) a monomeric 4R tau protein having a concentration of about 12.5 µM;
  (2) heparin having a concentration of about 1.25 µM;
  (3) a buffer composition comprising about 10 mM HEPES and having a pH of about 7.4;
  (4) a salt composition comprising NaCl in a concentration of about 100 mM; and
  (5) Thioflavin T (ThT) in a concentration of about 5 µM,
(C) combining the negative control sample and the second pre-incubation mixture in a second well of the reaction vessel to form a second incubation mixture;
(D) incubating the second incubation mixture at a temperature of about 37° C. with intermittent cyclic agitation cycles comprising about 1 minute of shaking at about 500 revolutions per minute followed by about 29 minutes without shaking to form a second incubated mixture;
(E) illuminating the second incubated mixture with an excitation wavelength of about 435 nanometers and an emission wavelength of about 485 nanometers; and
(F) determining a level of fluorescence during incubation of the second incubated mixture and comparing the level of maximum fluorescence of the first incubated mixture with the level of maximum fluorescence of the second incubated mixture, wherein an increase in the level of fluorescence of the first incubated mixture at maximum fluorescence of at least two times the standard deviation of the fluorescence of the first incubated mixture at maximum fluorescence compared to the level of fluorescence of the second incubated mixture after at least about 200 hours of incubation with intermittent agitation cycles indicates the presence of tau aggregate in the human CSF sample.

3. The method of claim 1, wherein the presence of the tau aggregates is indicative of a tauopathy, the method further comprising characterizing an identity of the tauopathy by analyzing the fluorescence kinetic parameters thereof for a signature of at least one of: Alzheimer's disease, progressive supranuclear palsy, frontotemporal Dementia, corticobasal degeneration, and chronic traumatic encephalopathy.

4. The method of claim 3, the analyzing comprising comparing one or more of: lag phase, T50, amplification rate, and amplification extent to one or more corresponding predetermined corresponding kinetic parameters that are characteristic of the identity of the tauopathy to determine a similarity or difference effective to characterize the identity of the tauopathy.

5. A method for the preparation of tau aggregates, the method comprising:
(A) providing human cerebrospinal fluid (CSF);
(B) providing a pre-incubation mixture that is free of tau seeds, the pre-incubation mixture comprising:
  (1) a monomeric 4R tau protein having a concentration of about 12.5 µM;
  (2) heparin having a concentration of about 1.25 µM;
  (3) a buffer composition comprising about 10 mM HEPES and having a pH of about 7.4; and
  (4) a salt composition comprising NaCl in a concentration of about 100 mM;
(C) combining the human CSF and the pre-incubation mixture to form an incubation mixture;
(D) incubating the incubation mixture at a temperature of about 37° C. with intermittent cyclic agitation cycles comprising about 1 minute of shaking at about 500 revolutions per minute followed by about 29 minutes without shaking to form an incubated mixture comprising the tau aggregates.

6. The tau aggregates prepared according to the method of claim 5.

7. The method of claim 5, further comprising detecting the tau aggregates, the detecting comprising:
(A) illuminating the incubated mixture with an excitation wavelength of about 435 nanometers and an emission wavelength of about 485 nanometers; and
(B) determining a level of fluorescence during incubation, wherein an increase in the level of fluorescence of the incubated mixture at maximum fluorescence of at least two times the standard deviation of the fluorescence of the incubated mixture at maximum fluorescence compared to the level of fluorescence of the incubation mixture at any time point up to about 50 hours of incubation with intermittent agitation cycles indicates the presence of tau aggregates in the human CSF sample.

8. The method of claim 5, further comprising characterizing the tau aggregates via contacting the tau aggregate with a proteinase selected from the group consisting of proteinase K, trypsin, and chymotrypsin.

* * * * *